US009014457B2

(12) United States Patent
Moss et al.

(10) Patent No.: US 9,014,457 B2
(45) Date of Patent: Apr. 21, 2015

(54) QUANTIFYING CELL DEATH

(75) Inventors: Stephen Moss, London (GB); Maria Francesca Cordeiro, London (GB); Steven Dakin, London (GB)

(73) Assignee: UCL Business PLC, London (GB)

( * ) Notice: Subject to any disclaimer, the term of this patent is extended or adjusted under 35 U.S.C. 154(b) by 165 days.

(21) Appl. No.: 13/505,334

(22) PCT Filed: Nov. 5, 2010

(86) PCT No.: PCT/GB2010/002040
§ 371 (c)(1),
(2), (4) Date: Jun. 5, 2012

(87) PCT Pub. No.: WO2011/055121
PCT Pub. Date: May 12, 2011

(65) Prior Publication Data
US 2012/0243769 A1 Sep. 27, 2012

(30) Foreign Application Priority Data

Nov. 6, 2009 (GB) .................................. 0919520.7

(51) Int. Cl.
*G06K 9/00* (2006.01)
*A61K 49/00* (2006.01)

(52) U.S. Cl.
CPC ......... *A61K 49/0004* (2013.01); *A61K 49/0032* (2013.01); *A61K 49/0056* (2013.01)

(58) Field of Classification Search
None
See application file for complete search history.

(56) References Cited

U.S. PATENT DOCUMENTS

2006/0134001 A1\* 6/2006 Frangioni ...................... 424/9.6
2008/0188573 A1 8/2008 Wei et al.

FOREIGN PATENT DOCUMENTS

WO 2009077750 A1 6/2009

OTHER PUBLICATIONS

ISA/EPO, International Search Report for corresponding international application No. PCT/GB2010/002040, mailed Aug. 3, 2011.

\* cited by examiner

*Primary Examiner* — Aaron W Carter
*Assistant Examiner* — Siamak Harandi
(74) *Attorney, Agent, or Firm* — Stites & Harbison PLLC; Mandy Wilson Decker

(57) ABSTRACT

The invention relates to methods of diagnosis, particularly methods of staging and diagnosing neurodegenerative diseases using images of cell death in the eye.

18 Claims, 16 Drawing Sheets

Original image     Averaged image     Standard deviation of spots compared to background Original image     Averaged image     Standard deviation of spots compared to background

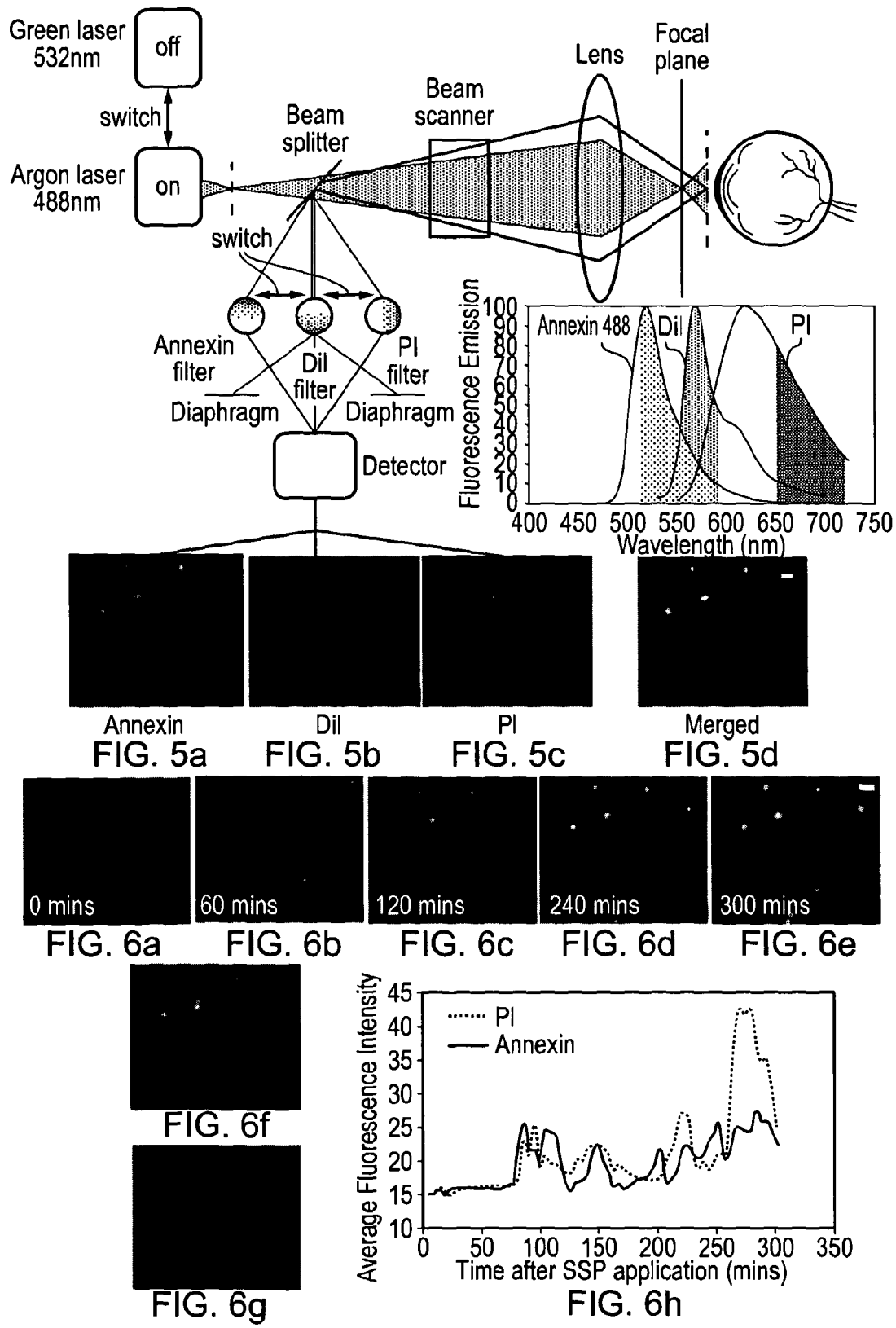

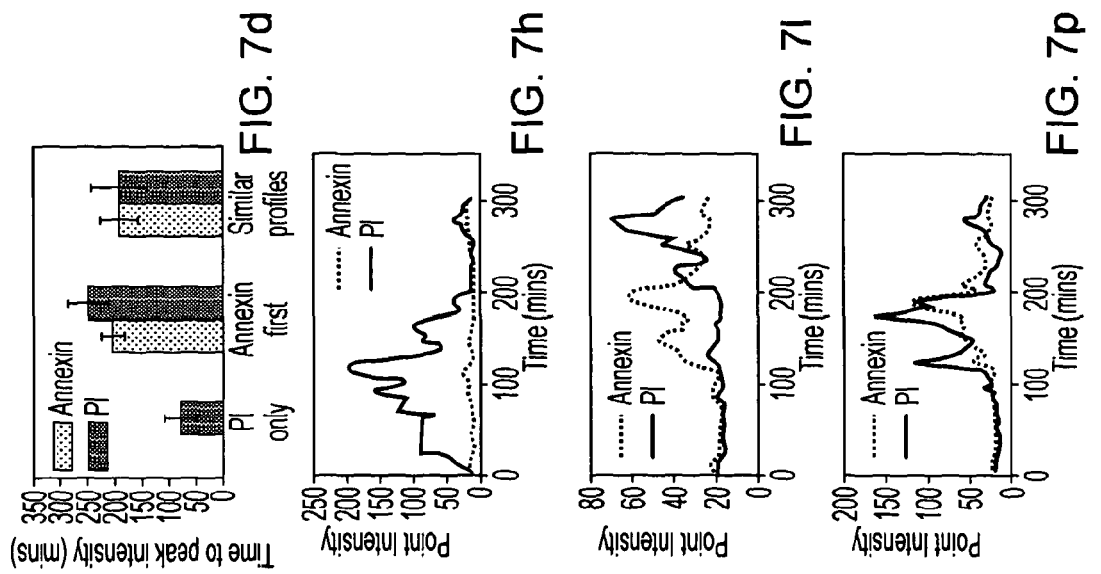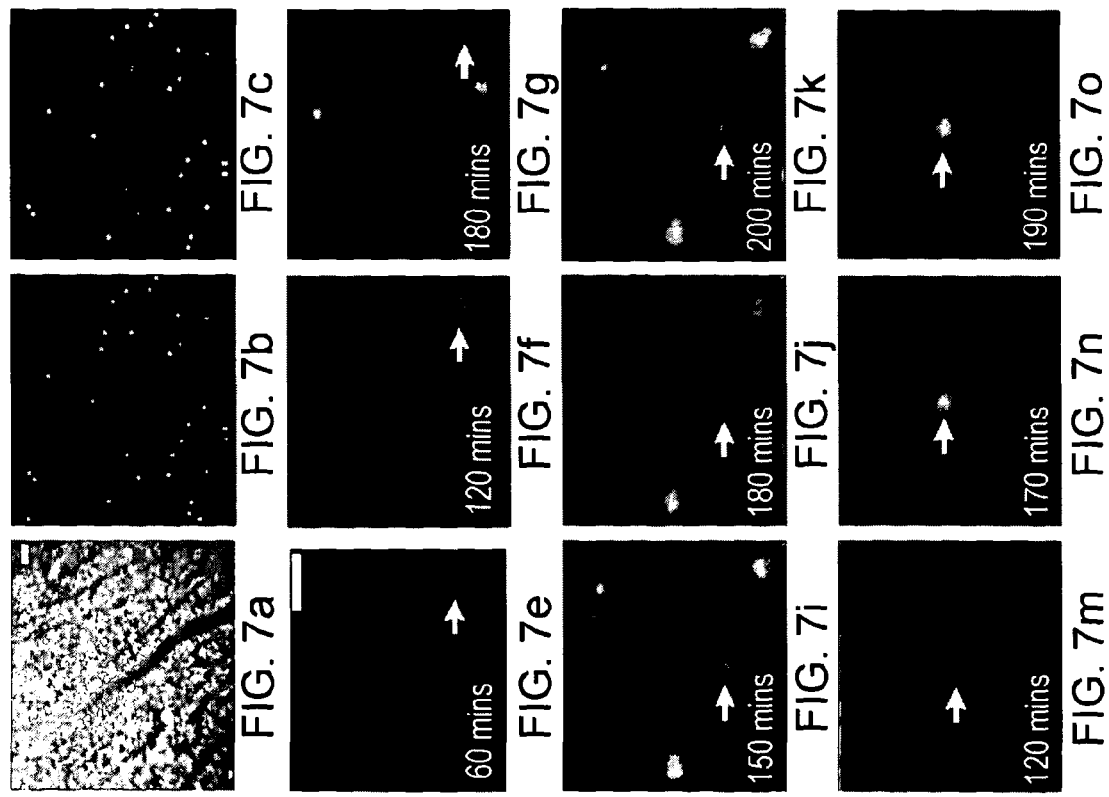

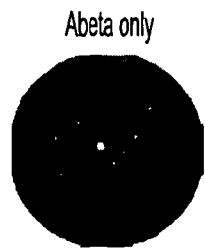
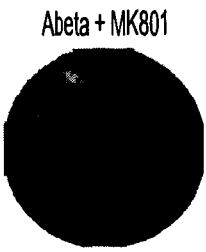
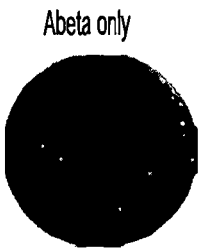
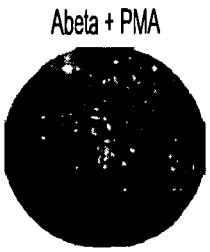
FIG. 8a    FIG. 8b    FIG. 8f    FIG. 8g
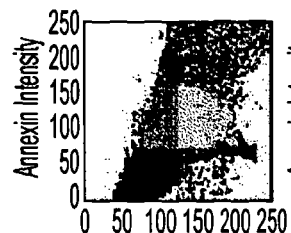
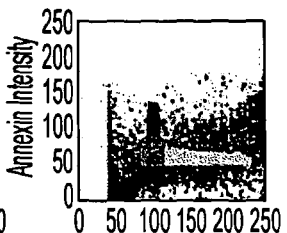
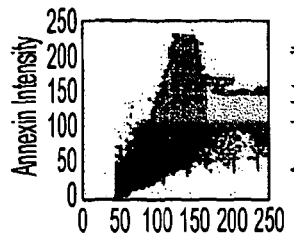
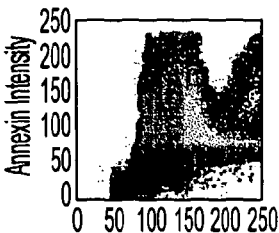
FIG. 8c    FIG. 8d    FIG. 8h    FIG. 8i
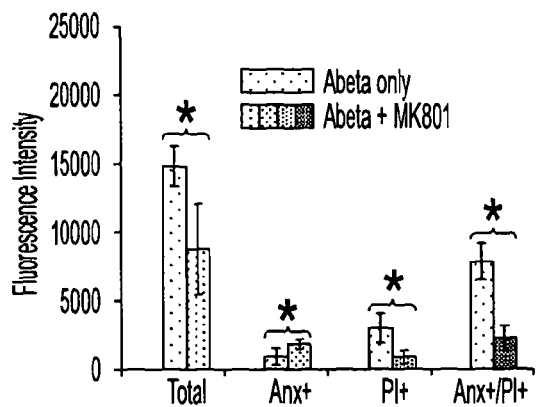
FIG. 8e
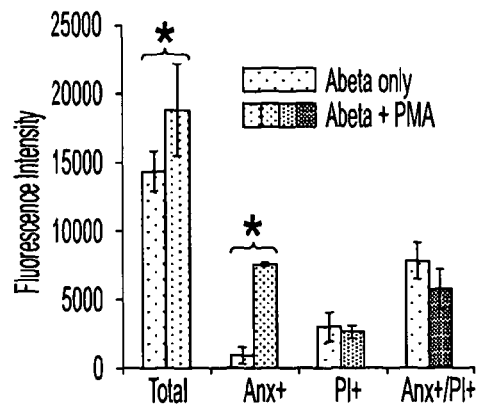
FIG. 8j
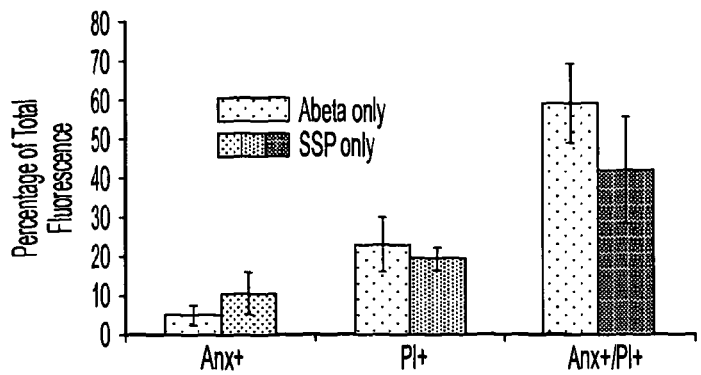
FIG. 8k

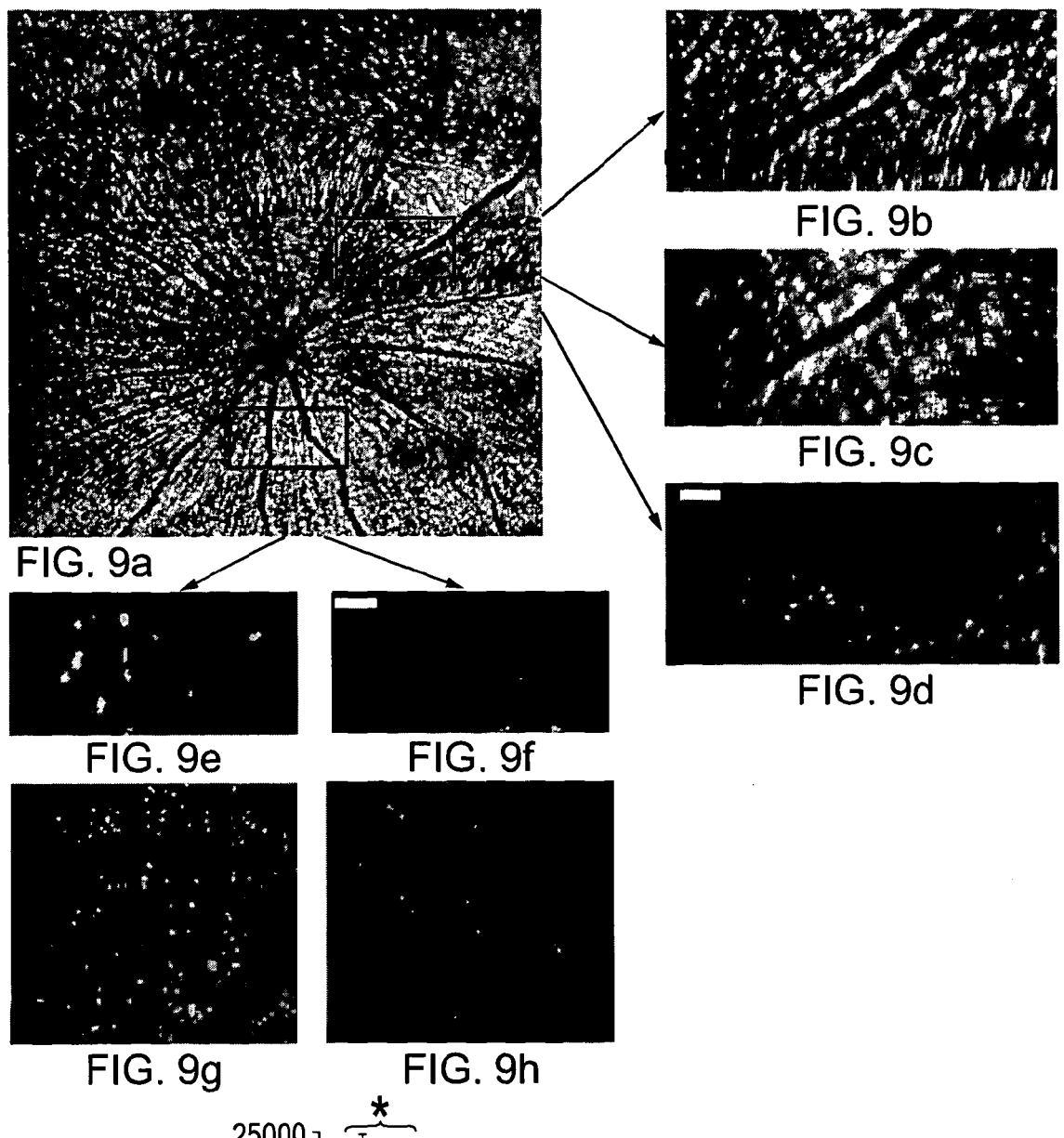
FIG. 9a
FIG. 9b
FIG. 9c
FIG. 9d
FIG. 9e
FIG. 9f
FIG. 9g
FIG. 9h
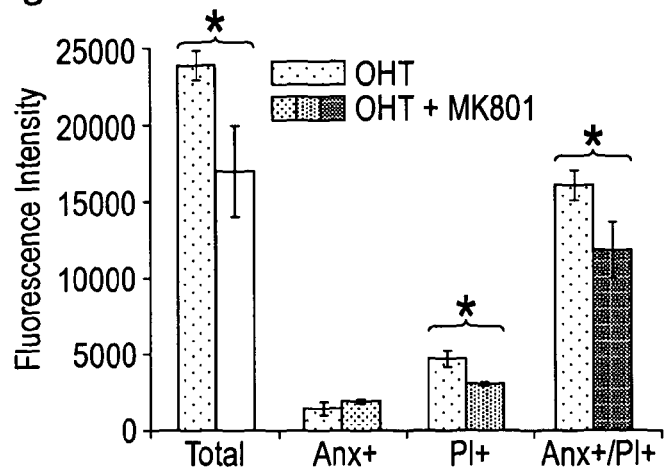
FIG. 9i

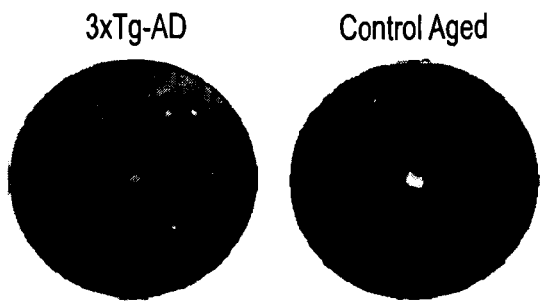
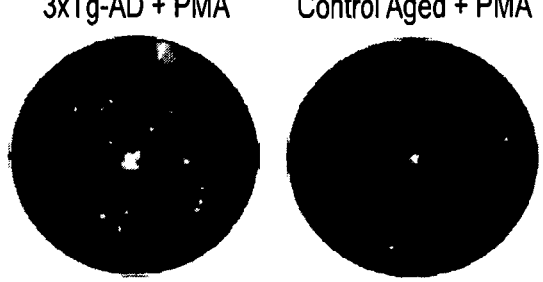
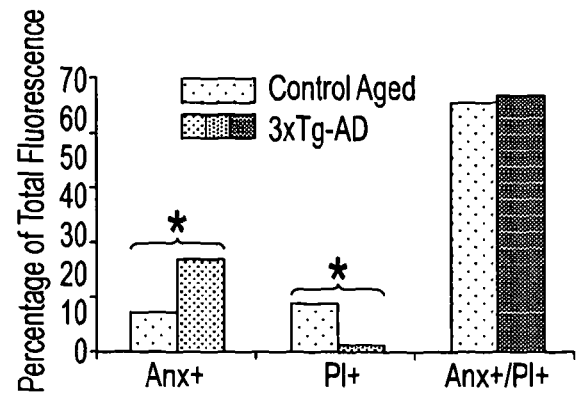
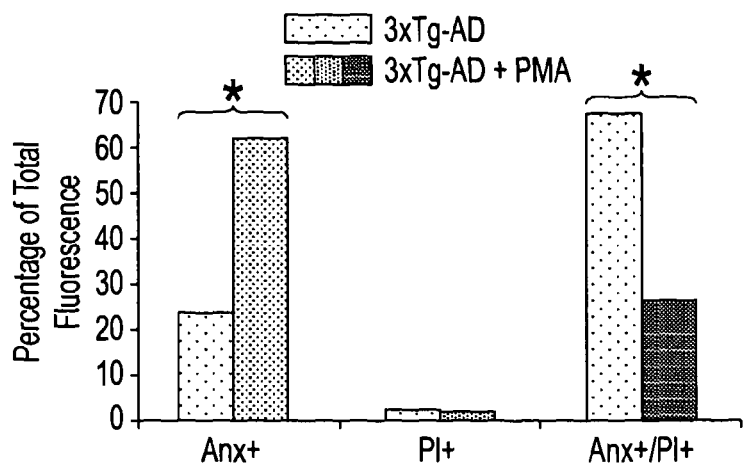
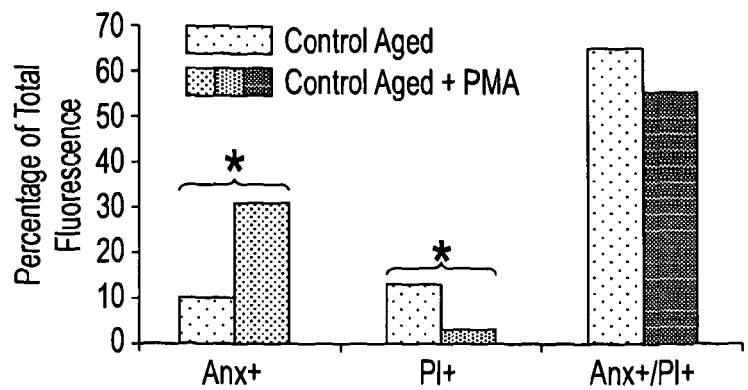

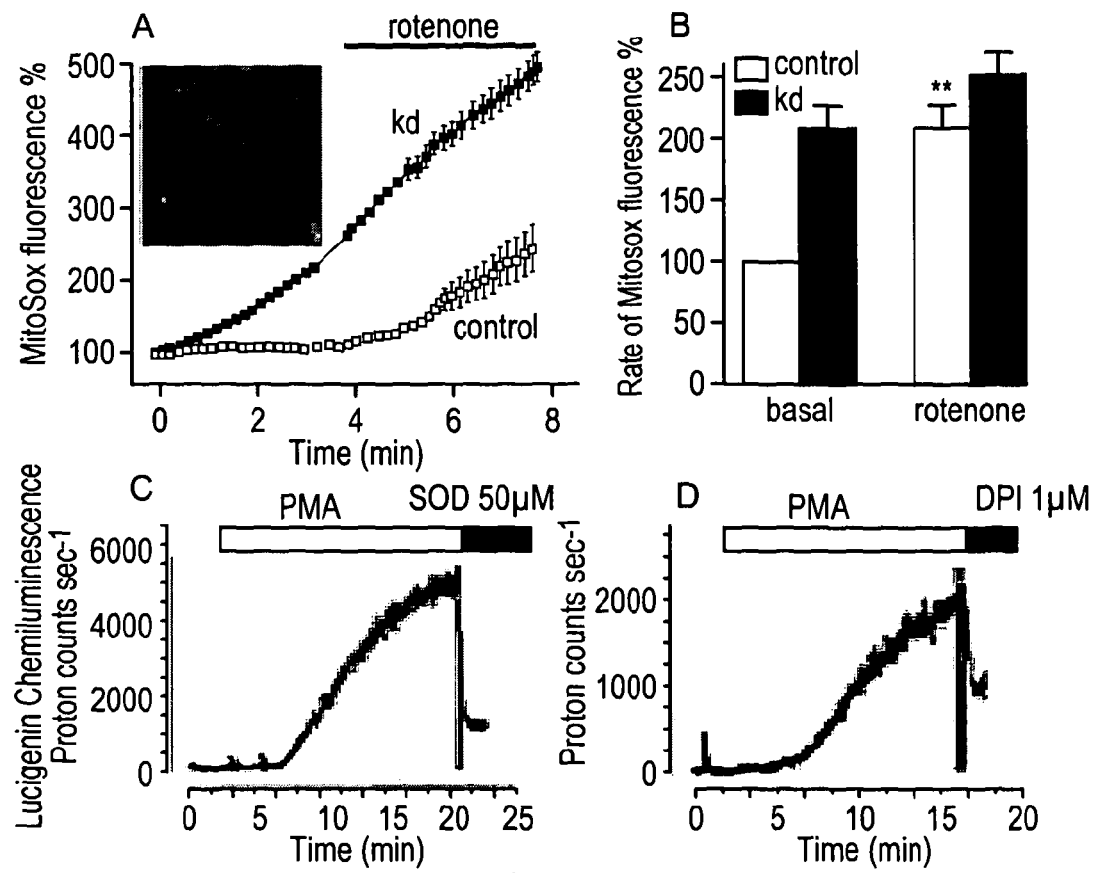
FIG. 12a
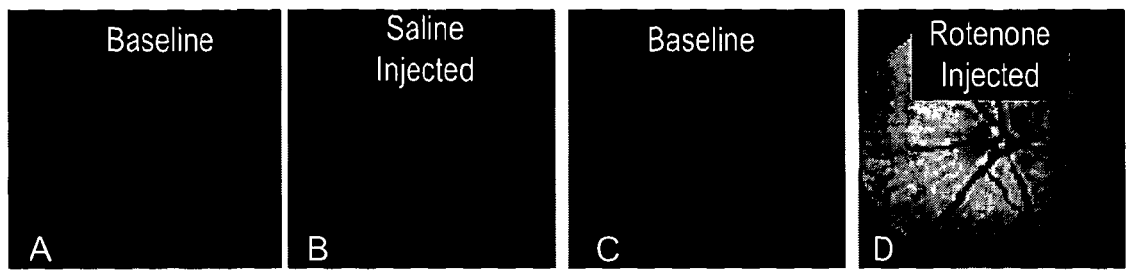
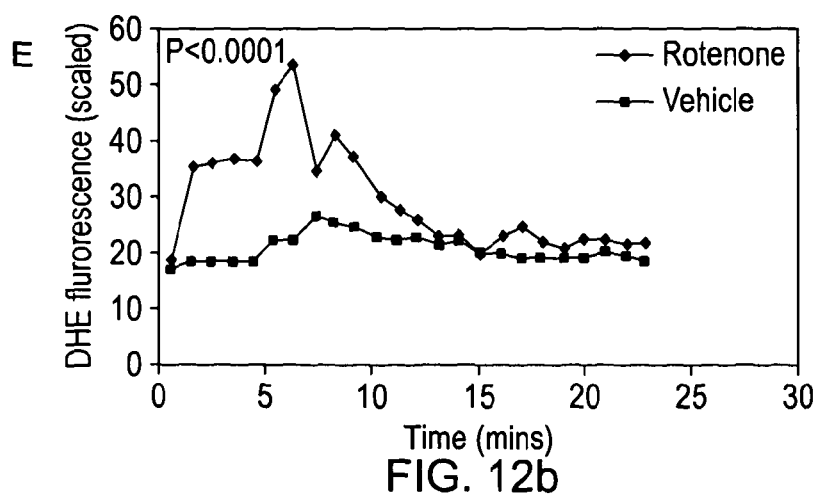
FIG. 12b

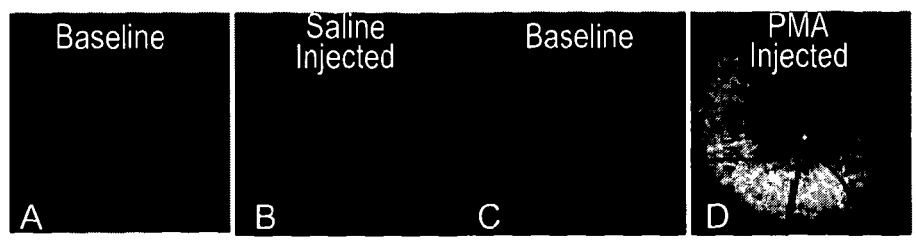
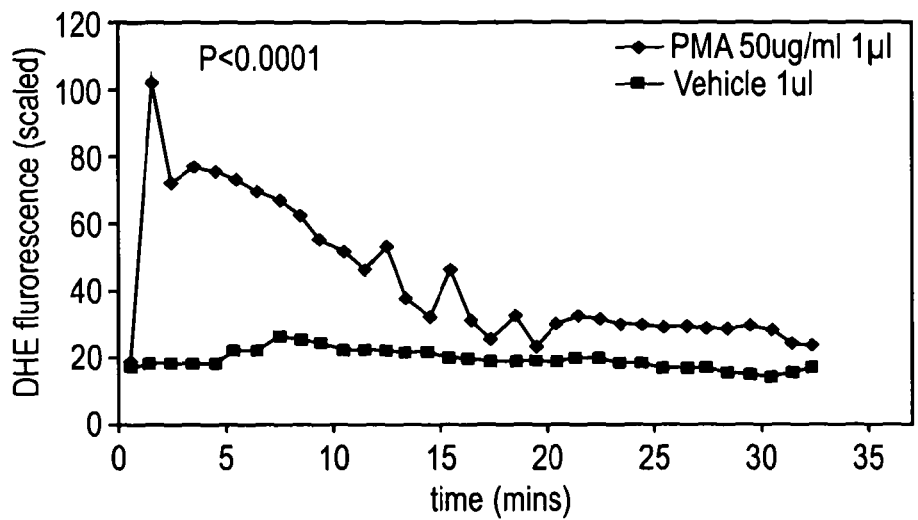
FIG. 12c
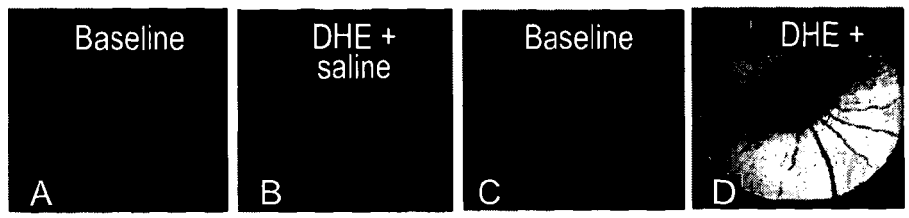
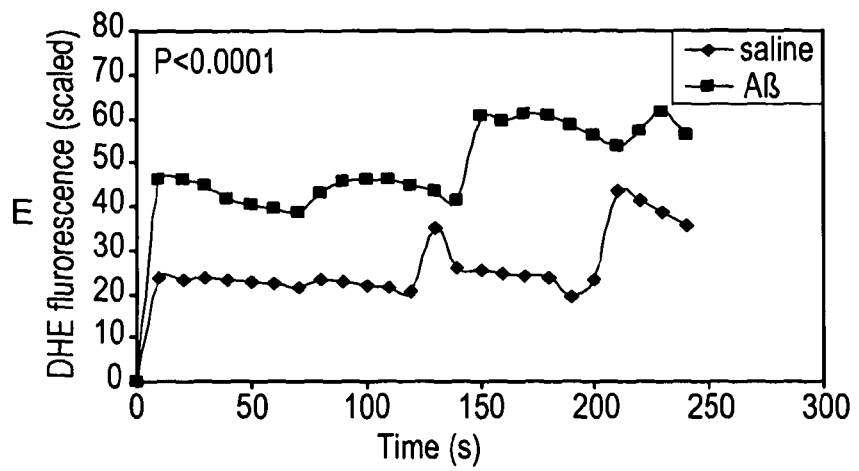
FIG. 12d

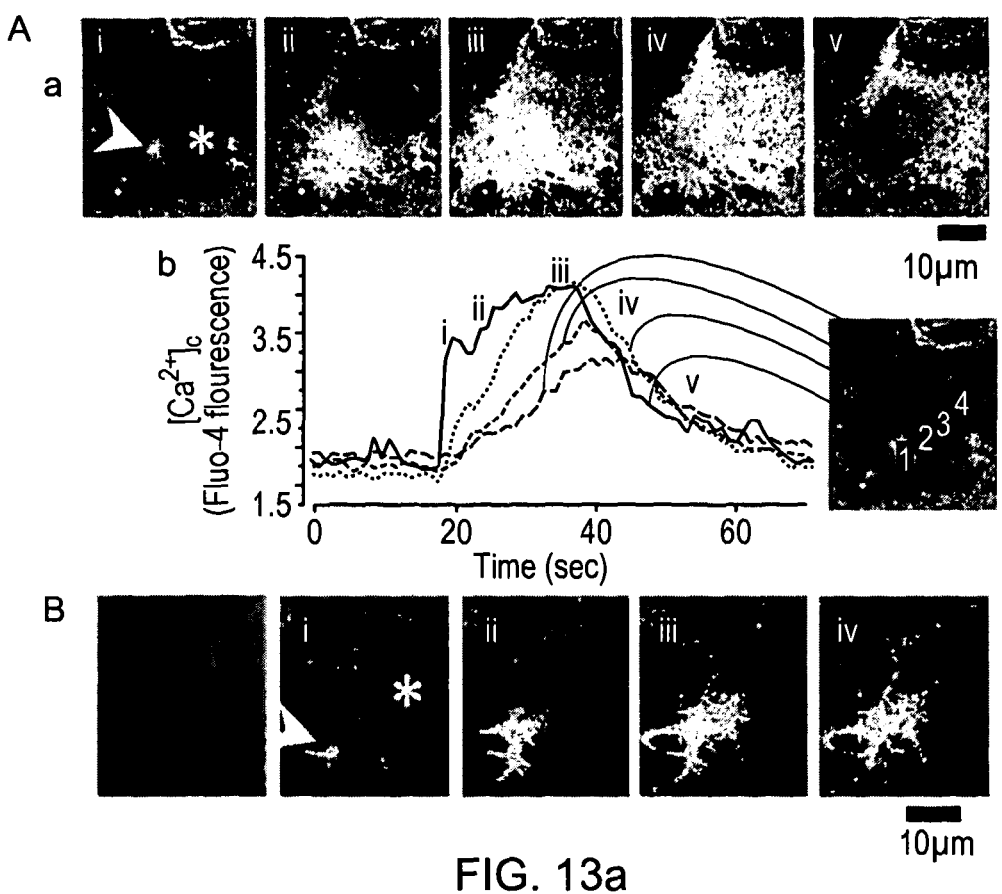
FIG. 13a
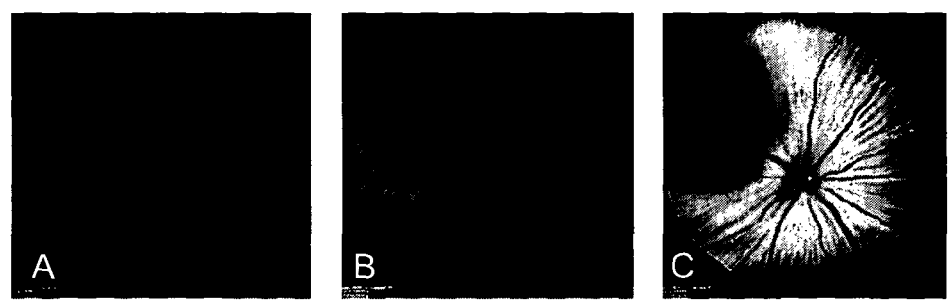
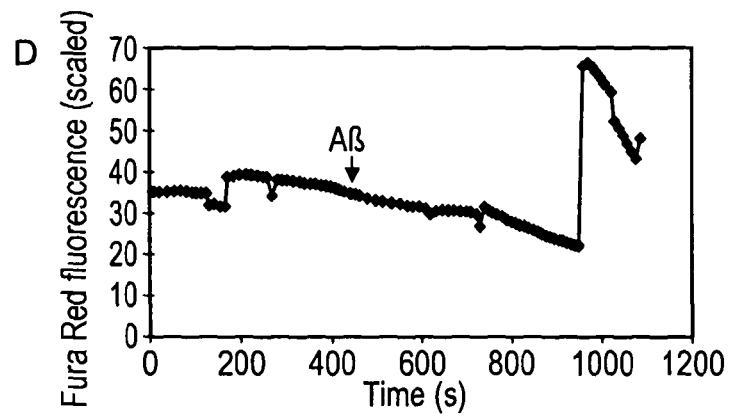
FIG. 13b

QUANTIFYING CELL DEATH

FIELD OF THE INVENTION

The invention relates to methods of diagnosis, particularly using images of cell death in the eye.

BACKGROUND OF THE INVENTION

Cell death and neuronal loss are the key pathological drivers of neurodegeneration in conditions such as Alzheimer's (AD), Parkinson's, Huntington's and glaucoma. AD is the commonest single form of dementia predicted to increase from affecting 4 to 12 million Americans over the next 20 years. Glaucoma is the major cause of irreversible blindness throughout the world, affecting 2% of people over 40. The condition has a significant morbidity due to its silent and progressive nature, often resulting in a delay in diagnosis and treatment.

Live cell imaging has been widely used to investigate neuronal dysfunction in cultured cells in vitro, which together with fluorescent multiple-labelling permits visualisation of different cell activities and distinct molecular localization patterns. Although in vivo imaging of the two major forms of cells death, namely apoptosis and necrosis, using radioligands have emerged in recent years (Saint-Hubert et al., 2009), until now, investigation of the progression and dynamics of the distinct phases of neurodegenerative disease at the cellular level has only depended on histological or in vitro analyses (Huerta et al., 2007).

Imaging the different phases of nerve cell death in vivo would significantly advance our ability to understand the disease and its natural history, with direct applications to the patient. It would allow investigation of the time course of events in relation to different modulators, and also provide insight into the spatial patterns of cell death over periods of days, weeks or longer. Furthermore, given the emergence of mechanistic commonalties between different neurodegenerative diseases, such as AD and glaucoma (Guo et al., 2009; Guo et al., 2007) an appreciation of the spatio-temporal dynamics of cell death in one disease could enhance our understanding of other diseases, both in terms of the molecular pathophysiology and potential therapeutic avenues. In particular, the possibility of blocking apoptotic cascade at early stages to rescue injured cells (Allen et al., 1997) makes the ability to differentiate between apoptosis and necrosis, as well as between different stages of apoptosis, particularly desirable.

SUMMARY OF THE INVENTION

The first aspect of the present invention is a method of determining the stage of a disease, especially a neurodegenerative disease, said method generating an image of apoptosing cells in a subject's eye, the subject having been administered a labelled apoptotic marker, and counting the number of apoptosing cells.

The method may also comprise administering the labelled apoptotic marker to the subject. The marker may be administered in any appropriate way, particularly via intravenous injection or topically.

The inventors have surprisingly found that number of apoptosing cells may be used to provide an indication of the stage of disease. Experiments based on animal model have shown that cell death is a dynamic process which closely correlates to disease stages. Therefore, the number of apoptosing cells can be used to identify time point in these diseases.

It is particularly preferred to be able to monitor progression of disease by comparing specific cells over time. Accordingly, the method may further comprise the step of comparing the image with an image of the subject's eye previously obtained. The method may comprise comparing the number of apoptosing cells or comparing specific cells in one image with the same cells in an earlier image. In the latter case, the cells may be apoptosing in one image but not the other, reflecting either the progression of disease or the efficacy of treatment given.

The change in the number of apoptosing cells can give a clinician information about the progression of disease. An increase in the number of apoptosing cells may indicate disease progression. Equally, as disease reaches its later stages, a fall in the number of apoptosing cells may be seen. The skilled clinician is able to differentiate the stages according to the number of cells seen in one image or using a comparison with one or more further images.

When comparing specific cells, it is advantageous to be able precisely overlay one image over another. The method may comprise this step, with one, two or three or more additional images.

The disease is preferably an ocular neurodegenerative disease. The term "ocular neurodegenerative diseases" is well-known to those skilled in the art and refers to diseases caused by gradual and progressive loss of ocular neurons. They include, but are not limited to glaucoma and diabetic retinopathy.

The term "apoptotic marker" refers to a marker that allows cells undergoing apoptosis to be distinguished from live cells. Additionally, the marker preferably should be able to distinguish apoptosing cells from neurotic cells. For example it may be a compound or molecule that specifically binds to apoptotic cells but not to live cells or necrotic cells, or one or more compounds or molecules that specifically bind to live cells and necrotic cells but not apoptotic cells. Apoptotic markers include, for example the annexin family of proteins. Annexins are proteins that bind reversibly to cellular membranes in the presence of cations. Annexins useful in the invention may be natural or may be recombinant. The protein may be whole or maybe a functional fragment, that is to say a fragment or portion of an annexin that binds specifically to the same molecules as the whole protein. Also, functional derivatives of such proteins may be used. A variety of annexins are available, such as those described in US Patent Application Publication No. 2006/0134001A. A preferred annexin is Annexin 5, which is well known in the art. Other annexins that may be used as apoptotic markers include Annexins 11, 2 and 6. Other apoptotic markers are known in the art including for example C2A domain of synaptotagmin-I, duramycin, non-peptide based isatin sulfonamide analogs, such as WC-II-89, and ApoSense, such as NST-732, DDC and ML-10 (Saint-Hubert et al., 2009).

Alternatively the marker may be a molecule or compound released or expressed by a cell during apoptosis or during necrosis but not released or expressed by live cells or a molecule or compound released or expressed by a living cell but not during one or both of apoptosis or necrosis. Other indications of cell activity can also be used to identify apoptotic or necrotic cells. For example, changes in mitochondrial function may be observed, reactive oxygen species (ROS) may be used as markers, as may calcium ions.

The apoptotic marker is labelled, preferably with a visible label. In particular, the label is preferably a wavelength-optimised label. The term 'wavelength-optimised label' refers to a fluorescent substance, that is a substance that emits light in response to excitation, and which has been selected for use due to increased signal-to-noise ratio and thereby improved image resolution and sensitivity while adhering to light exposure safety standard to avoid phototoxic effects. Optimised wavelengths include infrared and near-infrared wavelengths. Such labels are well known in the art and include dyes such as IRDye700, IRDye800, D-776 and D-781. Also included are fluorescent substances formed by conjugating such dyes to other molecules such as proteins and nucleic acids. It is preferred that optimised wavelengths cause little or no inflammation on administration. A preferred wavelength-optimised label is D-776, as this has been found to cause little or no inflammation in the eye, whereas other dyes can cause inflammation. Optimised dyes also preferably demonstrate a close correlation between the level of fluorescence that may be detected histologically and that which may be detected in vivo. It is particularly preferred that there is a substantial correlation, especially a 1:1 correlation between the histological and in vivo fluorescence.

The labelled apoptotic marker may be prepared using standard techniques for conjugating a wavelength-optimised label to a marker compound. Such labels may be obtained from well known sources such as Dyomics. Appropriate techniques for conjugating the label to the marker are known in the art and may be provided by the manufacturer of the label.

In order to generate an image of apoptosing cells, the labelled marker is administered to the subject, by, for example, intravenous injection or by topical administration. The area of the subject to be imaged, the eye, is placed within the detection field of a medical imaging device. Emission wavelengths from the labelled marker are then imaged and an image constructed so that a map of areas of cell death is provided. Generation of the image may be repeated to allow apoptosis to be monitored over a period of time. It may be monitored in real time. It is particularly preferred to monitor apoptosis of retinal cells, especially retinal nerve cells. Retinal nerve cells include retinal ganglion cells (RGC), bipolar, amacrine, horizontal and photoreceptor cells.

In one embodiment of the present invention, an 'averaged' image is acquired from the original image using a software specifically developed for autofluorescence imaging (von Ruckmann et al., 1995; Wade & Fitzke, 1998) and a standard deviation of spots compared to background is created. In order to eliminate background noise, spots with an area above a certain threshold, are counted as "cells" and those with an area below the threshold indicate noise. The number of apoptosing cells obtained is known as the DARC count.

The second aspect of the present invention is a method of diagnosing a disease generating an image of apoptosing cells in a subject's eye, the a labelled apoptotic marker having been administered to the subject, and analysing the pattern of distribution of apoptosing cells.

The method may also comprise administering a labelled apoptotic marker to the subject, especially intravenously or topically.

Preferably the disease is a neurodegenerative disease, especially an ocular neurodegenerative disease, especially glaucoma.

The inventors have found that it is possible to identify disease by the distribution of apoptosing cells. In particular, by preparing a density map showing distribution of apoptosing cells the distribution of cell death can be demonstrated. From that map, it is possible to differentiate between different neurodegenerative diseases which have distinct patterns of apoptotic activity.

The terms 'ocular neurodegenerative diseases', 'apoptotic marker' and 'label' are as described above.

The method used to generate the retinal image of apoptosing cells is as described above. Once an image of apoptosing cells of the eye is obtained, a density map of these cells can be constructed using a standard software. Again, it may be useful to overlay one map with one or more other maps generated at an earlier time and the method may include this step or the step of comparing the map with one or more previously generated maps.

In one embodiment the method relates to distinguishing between glaucoma and other diseases.

The third aspect of the invention provides a method of staging disease by monitoring activity or cell death comprising generating an image of cell activity or call death in a subject's eye, a first labelled marker and a second labelled having been administered to the a subject, wherein the first and second markers are markers of different phases of apoptosis, or of two of cell activity, apoptosis and necrosis, and wherein the labels are different, and assessing the stage of disease by studying the co-localisation markers.

In particular, the invention provides a method of differentiating between different phases of cell death comprising generating an image of cell death in a subject's eye, a first labelled cell death marker and a second labelled cell death marker, wherein the first and second markers are markers of different phases of apoptosis, or of apoptosis and necrosis, and wherein the labels are different, having been administered to the a subject, and assessing the magnitude of different phases of cell death by studying the co-localisation markers, The method may also comprise administering a first labelled cell death marker and a second labelled cell death marker to the subject.

Preferably the two markers are markers for necrosis and apoptosis. Preferably the labels are wavelength optimised labels.

The method according to the third aspect of the invention can also be used for quantifying the different phases of cell death.

The term 'cell death' refers to any process including, for example, death of a cell by apoptosis and necrosis.

The terms 'apoptotic marker' and 'label' are as described above.

The term 'necrotic marker' refers to a marker that allows cells undergoing necrosis to be distinguished from live cells and those undergoing apoptosis. For example it may be a compound or molecule that specifically binds to necrotic cells but not to live cells or apoptosis cells, or one or more compounds or molecules that specifically bind to live cells and apoptotic cells but not necrotic cells. Necrotic markers include, for example propidium iodide (PI), an intercalating agent that binds to nucleic acid with little or no sequence preference. Other necrotic markers are known in the art including pyrophosphate, antimyosin, glucarate, hypericin and its derivatives, such as hypericin monocarboxylic acid and pamoic acid, such as bis-hydrazide-bis-DTPA pamoic acid. 99mTc-pyrophosphate, 111In-antimyosin, and 99mTc-glucarate have been used in particular.

The labelled necrotic marker may be administered locally or systemically in a similar way to the labelled apoptotic marker mentioned above.

The method used to generate the retinal image of apoptotic cells and necrotic cells is as described above. In one embodiment of the present invention, co-localisation of apoptotic cells and necrotic cells is studied by generating co-localisation scatter plots and colour thresholds using ImageJ software with the Intensity Correlation Analysis plugin. When colour and raw scatter plots of the apoptotic and necrotic marker fluorescence intensity are constructed, data can be analysed by the adoption of thresholds set automatically by the plugin, thereby enabling separation of the different phases of cell death according to whether they were apoptotic marker positive, i.e. early apoptosis, apoptotic and necrotic markers double positive, i.e. late apoptosis, and necrotic marker positive, i.e. necrosis. Fluorescence intensity counts derived from raw scatter plots are used to quantify each phase of cell death. Again, the co-localisation of the necrotic and apoptotic cells can be compared with those at an earlier stage by comparing the image with a previously generated image, particularly by overlaying the two or more images, as with previously described methods.

It may be useful to distinguish between the stages of apoptosis and between necrosis and apoptosis in order to determine the stage of disease, the stage of apoptosis and which treatment regime should be followed.

It is particularly useful to be able to stage or diagnose disease, as it allows a particular treatment course to be selected and, optionally, monitored. Accordingly, the method optionally includes administering to the subject a treatment for glaucoma or another neurodegenerative disease.

Glaucoma treatments are well known in the art. Examples of glaucoma treatments are provided in the detailed description. Other treatments may be appropriate and could be selected by the skilled clinician without difficulty.

In particular when apoptosis is identified as being in the early stage, it may be useful to treat with any neuroprotective drug that modulates nerve cell death.

The invention also provides the use of a neuroprotective agent or other appropriate agent in the treatment of glaucoma or neurodegenerative disease, wherein the treatment is for a subject in which the disease has been staged or diagnosed using the method of the invention.

BRIEF DETAILED DESCRIPTION OF THE DRAWINGS

The invention will now be described in detail, by way of example only, with reference to figures, in which.

Figure 1:
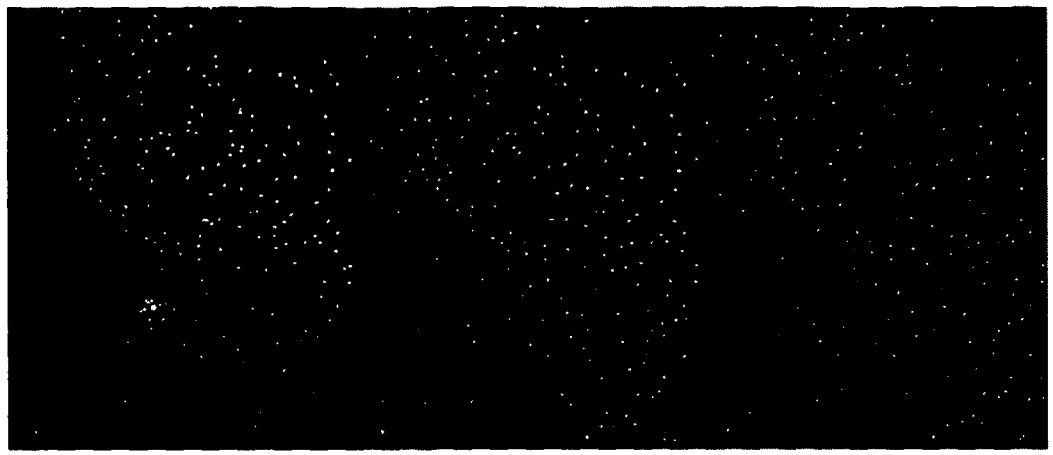
FIG. 1 shows an original DARC retinal image, an averaged image obtained using software for autofluorescence imaging and the resulting standard deviation of the spots.

FIG. 5 shows detection of fluorescent-labelled cells using confocal scanning laser ophthalmoscopy (cSLO). Simultaneous detection of multiple markers was achieved by customizing the cSLO as follows: for identification of annexin 488, an Argon laser wavelength of 488 nm, and a solid state photodetector with a 521 nm cut-off filter and a 550 nm cut-on filter was employed; for DiI, a diode-pumped crystal green laser with a wavelength of 532 nm was used with 550 nm cut-off and 600 nm cut-on filters; the same laser was used for PI visualization but with a 650 nm cut-off. The inset graph shows the emission spectra of cellular marker fluorochromes used in study. Alexa Fluor 488-labelled annexin V (green; Annexin 488), DiI (blue; 1,1'-dioctadecyl-3,3,3',3'-tetramethylindocarbocyanine perchlorate) and Propidium iodide (red; PI) have excitation/emission maxima of 495/519, 550/570 and 532/649 nm respectively. (a-d) Monochrome images from each retinal area were acquired using the appropriate laser set-up and colourised. Three-color images were produced by combining each of the grayscale images from the cLSO into the green (a, annexin 488), blue (b, DiI) and red channels (c, PI) of an RGB color image, and merged to form the image shown in (d) (scale bar 100 µm).

FIG. 6 shows time-lapse video analysis of changes in cell markers in vivo. (a-g) Stills taken from video sequence (supplementary video 1) in an SSP-treated rat eye with labelled Retinal Ganglion Cells (RGCs; DiI, blue) and intravitreal annexin V (green) and propidium iodide (PI, red), reveal a random distribution and appearance of annexin V and PI stained cells, but demonstrate the clear increase in PI staining over time. (DI, blue; annexin V, green; propidium iodide, red; time points and scale bar 100 µm as indicated). (f-g) Average fluorescence intensity projections of video sequence using ImageJ RGB Zprojector plugin with annexin/PI (f) and all three channels (g). (h) Temporal analysis of the average annexin (green) and PI (red) intensities taken from each image sequence histogram, demonstrates that the profiles of annexin and PI change significantly over time with a marked increase in late PI staining.

FIG. 7 shows different patterns and phases of cell death in vivo. (a-b) Random sample (n=30) of single cells selected according to whether they were DiI positive (white spots, DiI retrogradely labelled retinal ganglion cells, a) and stained either with annexin V-488, PI or both during time lapse video (light blue spots, b). (c-p) Three patterns of fluorescent labelling were identified: "PI only" (red spots, c, and representative cell arrowed in e-g video stills with corresponding signal intensity profile in h), "Annexin first" (annexin V-positive and subsequently PI-positive, green spots c, i-I), "Similar profiles" (positive labelling for both dyes at the same time, yellow spots, c, m-p). The mean times to peak intensity (d) revealed that the appearance of the "PI only" cells was significantly quicker than either the "annexin first" or "similar profiles" cells. Intensity profiles of annexin V and PI changed significantly over time (h,l,p). These results provide evidence that neuronal cells in vivo display considerable heterogeneity with regard to the kinetics of necrotic and apoptotic cell death, and also the relative timing of phosphatidylserine exposure (early phase) and nuclear condensation (late phase). Time points and scale bar 100 µm as indicated.

FIG. 8 shows analysis of cell death phases in a mouse model of Abeta-induced RGC death. (a-b) Wide-angle retinal images showing the Abeta-treated right eye (a) and Abeta+ MK801 treated left eye (b) of a single mouse. MK801 reduces the number of annexin V (green) and PI (red) positive cells 72 hours after intravitreal Abeta (25-35) application. To assess the magnitude of late apoptosis the inventors studied the co-localization of PI and annexin V using Image) software with the Intensity Correlation Analysis plugin. (c-d) Scatter plots show the distribution of annexin and PI fluorescence intensity in the eyes shown in a and b, Abeta alone (c) and Abeta+MK801 (d). (e) Thresholds were set automatically by the plugin for each analysis (colour overlay in C and D), and quantification of each cell death phase was performed from generated data (e). MK801 treatment reduced the overall levels of cell death (blue, Total), mostly by reducing the number of cells in late phase apoptosis (yellow, Anx+/PI+) and necrosis (red, PI+). (f-g) Wide-angle retinal images showing the Abeta-treated right eye (f) and Abeta+PMA-treated left eye (g) of a single mouse. (h-i) PMA increased the level of annexin V (green) and PI (red) positivity as shown in the corresponding scatter plots. (j) Quantification of all treated animals shows that PMA significantly (p<0.05) increases the overall levels of cell death (blue, Total), most of this being due to a significant (p<0.05) increase in the number of cells in the early phase of apoptosis (green, Anx+). (k)

Comparison of cell phases in all Abeta and SSP models using co-localization scatter plot analysis. At the previously established time points of maximal apoptosis (Abeta=72 h and SSP=2 h), both models show a similar trend with no significant difference in the magnitude of any phase of cell death. However, both models show significantly more RGCs in the phases of late apoptosis (p>0.05, yellow, Anx+/PI+) and necrosis (p>0.05, red, PI+) than early apoptosis (green, Anx+). Error bars 95% confidence intervals, *p<0.05.

FIG. 9 shows natural history of cell death in chronic ocular hypertensive (OHT) model of neurodegeneration. (a-f) Cells were retrogradely labeled using DiI (A), and analysed at intervals over 8 weeks. The higher magnification image (green box in (a)) taken at time zero (b) shows the normal density of RGCs, with little change at 3 weeks (c). However, there was marked RGC drop-out 8 weeks after surgical-induction of elevated IOP (d). When the data were analysed with respect to the identification of apoptosis in these same cells, it was clear that those RGCs that were annexin V positive at 3 weeks (e) were no longer identifiable at 8 weeks (f), confirming that cells originally classified as undergoing apoptosis had degenerated five weeks later. (g) Only a small proportion of RGCs were identified in early phase apoptosis (annexin V only) compared to late phase apoptosis (both annexin V and PI staining) at 3 weeks. (h) MK801 treatment of animals at the time of surgery significantly reduced the number both of apoptotic and necrotic cells 3 weeks after treatment. (i) Quantitative analysis of the co-localization data for PI and annexin V confirmed that significantly more cells were in late phase apoptosis (p>0.05, yellow, Anx+/PI+) than necrosis (red, PI+). Treatment with MK801 led to a significant reduction (p<0.05) in the number of dying cells (Total), mostly due to a significant decrease in the levels of necrosis (p>0.05, red, PI+) and late apoptotic (p>0.05, yellow, Anx+/PI+) cell death. Scale bar 100 µm as indicated, error bars represent 95% confidence intervals, *p<0.05.

FIG. 10 shows retinal cell death in the Alzheimer Triple Transgenic model. (a-b) Representative wide-angle retinal images of 14-month Alzheimer Triple Transgenic (3× Tg-AD, a) mouse acquired 2 hours after intravitreal PI (red) and annexin (green), compared to (b), an 18 month, PS1KI control mouse. (c) Quantitation of co-localization scatter plot data showing significantly more RGCs in the early phase of apoptosis (p<0.05, green, Anx+) and relatively fewer necrotic cells (p<0.05, red, PI+) in the 3× Tg-AD compared to control. (d-e) Retinal images of eyes of a 14 month 3× Tg-AD animal (d) and a control aged animal (e) acquired 2 hours after PMA was administered at the same time as intravitreal annexin (green) and PI (red). (f-g) Quantification of the data generated by co-localization scatter plot analysis showed that PMA treatment significantly increased early apoptosis (p<0.05, green, Anx+) and decreased late apoptosis (p<0.05, yellow, Anx+/PI+) in the 3× Tg-AD model (g). PMA also increased the level of early apoptosis in the aged control animals (p<0.05, green, Anx+), although not to the same extent (30.3% in aged control as opposed to 61.4% in 3× Tg-AD). *p<0.05

FIG. 11 shows that changes in mitochondrial function can identified in retinal cells. This can be used as a marker in the present invention.

Figure 11A:
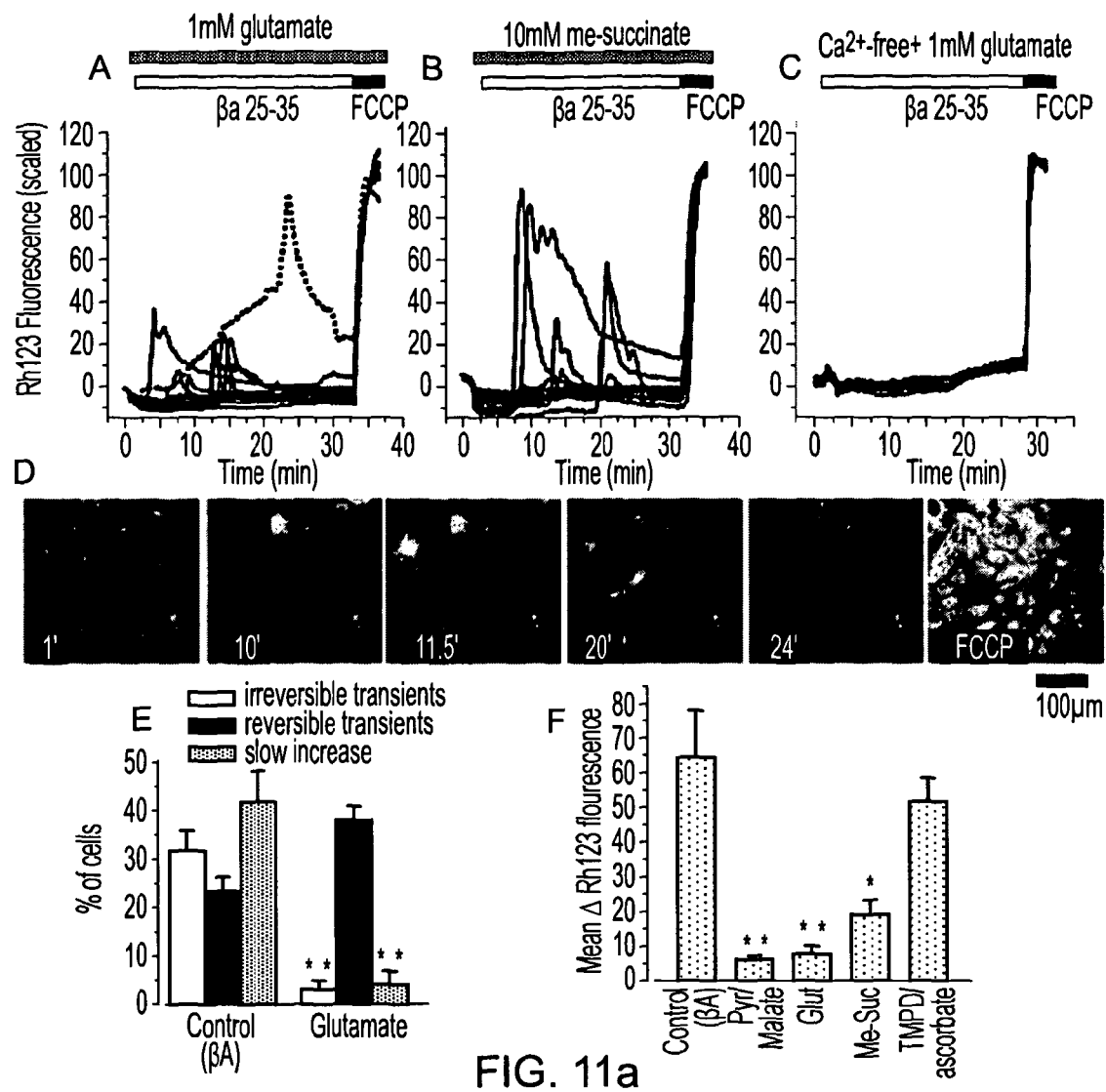

FIG. 11A. Live cell imaging of changes in mitochondrial depolarization (Abramov A Y et al. J Neurosci 24:565-75., 2004). Changes in Rho123 signal were measured in a culture of cortical astrocytes in response to Aβ 25-35 (50M) in the presence of 1 mM glutamate (A), 10 mM methyl-succinate (B), and 1 mM glutamate in a Ca 2-free saline with the addition of 500M EGTA (C). In the presence of either glutamate or methyl succinate, fast reversible transient mitochondrial depolarizations were still seen, but the slow progressive mitochondrial depolarization was abolished almost completely; compare with the day-matched control trace shown in A as a dashed line. In the presence of glutamate and the absence of external Ca2+ the entire response was abolished. In D are shown a series of images extracted from a time sequence showing changes in mitochondrial potential in response to Aβ in the presence of methyl succinate. Note that the Rh123 signal in some cells becomes transiently very bright but then is restored and shows a further increase with FCCP in the final image. The final image with FCCP shows the first image acquired immediately after application of FCCP, because the signal continued to get even brighter with a saturation of the display at this range. The time of each image in the sequence is indicated (minutes). An analysis of the effect of glutamate on different components of the response is shown in E, and the measurements of the mean increase in Rh123 fluorescence at 30 min in response to A in the presence of glutamate, methyl succinate, and TMPD/ascorbate are shown in F. *p0.01; **p0.001

Figure 11B:
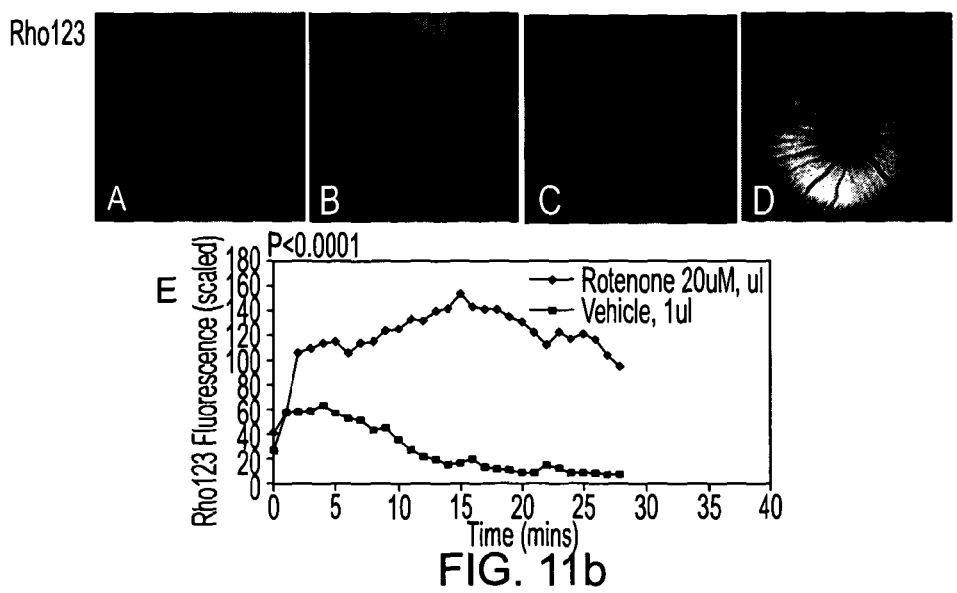

FIG. 11B. Early investigations show the effects of intravitreal rotenone on mitochondrial membrane potential (MMP) in a mouse eye in vivo. Intravitreal administration of Rotenone (20 uM, 1 ul) resulted in stronger Rho123 fluorescent signals in the retina (D), compared to control eye (B) and baseline (A, C). Statistical analysis showed that rotenone induced significant mitochondrial membrane depolarization compared to vehicle control (E).

Figure 11C:
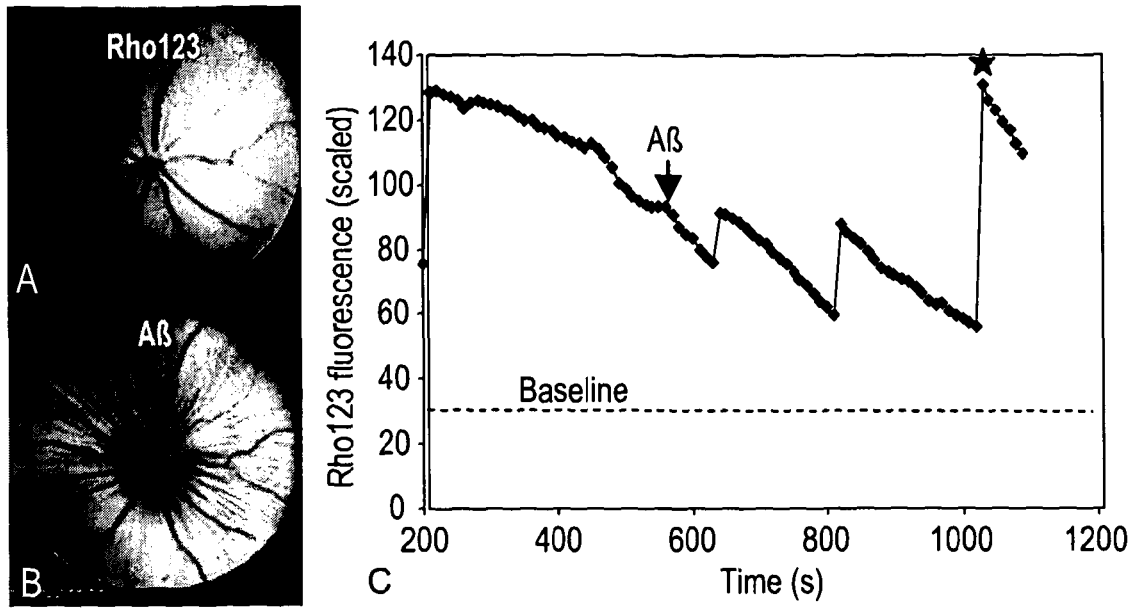
Figure 11D:
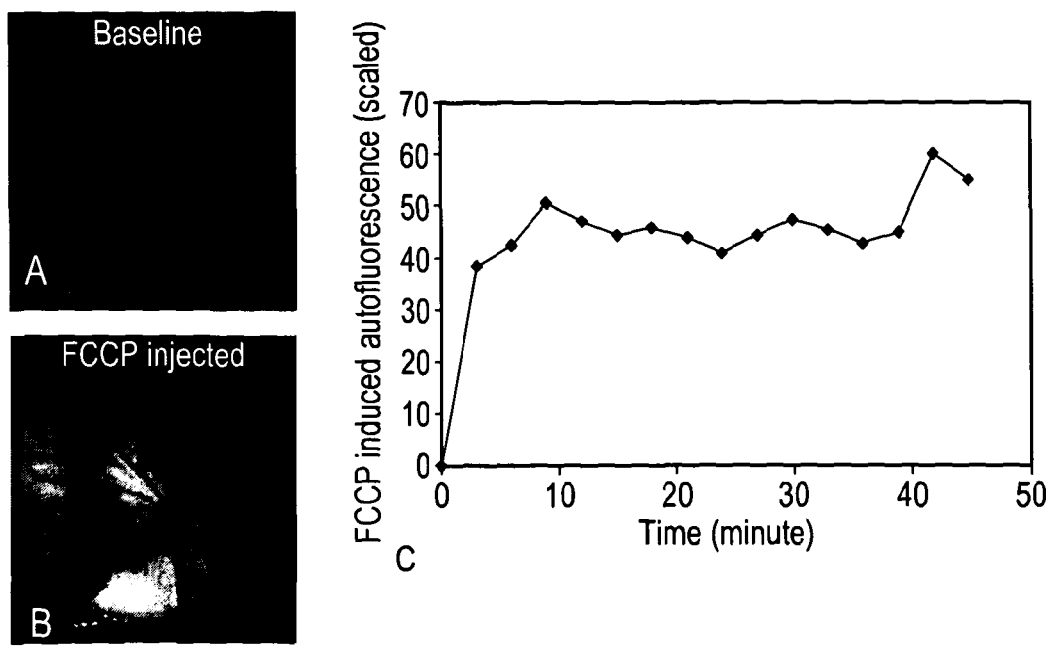

FIG. 11C. Using the same analysis, we looked at the effects of Aβ25-35 on MMP in vivo in a mouse eye. Rho123 is a fluorescent probe, used to detect the changes in mitochondrial fluorescent density. Administration of Aβ25-35 (as shown C 'star') showed a strong fluorescent signal at the level of the RGCL (B). Quantitative analysis showed that Aβ administration resulted in a significant loss of the MMP in the retina with a few minutes delay, compared to baseline (A) (C, p<0.01). The dashed line in C represents baseline fluorescence before Rho123 was injected FIG. 11D. Detection of FCCP-induced retinal metabolic changes in vivo in a mouse eye. Intravitreal administration of FCCP (Carbonylcyanide-p-trifluoromethoxy-phenylhydrazone), a potent mitchondria uncoupler, causes an increase in real time autofluorescence in vivo in the retina of mice suggesting that changes in ocular cell metabolic activity such as NADH and FAD can be visualised FIG. 12 shows that changes in ROS function can identified in retinal cells. This can be used as a marker in the present invention.

FIG. 12A. Rotenone (A, B) and PMA (C, D) induced ROS production in vitro (Wood-Kaczmar A et al, PLoS ONE 3:e2455, 2008) Rotenone, a mitochondrial complex I Inhibitor, caused a significant increase of ROS production in control cells, and this increase was even greater in PINK1 knockdown (kd) cells measured by MitoSox fluorescence (A, B). (PINK1 is a genetic factor, playing a neuroprotective role in the mitochondria of mammalian neurons against oxidative stress. PINK1 kd cells appeared to have lost the protective effect). Application of phorbol ester PMA (1 µg/ml), an activator of NADPH oxidase, induced an increase in ROS generation from astrocyte cultures measured using lucigenin luminescence fluorescence (C, D). The lucigenin response was reversed by the addition of superoxide dismutase to scavenge superoxide (A), demonstrating the specificity of the response, and was blocked by DPI (B).

FIG. 12B. The effects of rotenone on ROS production in mouse retina in vivo. ROS production visualized with DHE (dihydroethidium). DHE is a non-fluorescent agent, reacting with ROS intracellularly to produce a fluorescent oxidative product which can be detected. Rotenone (50 uM, 1 ul) was intravitreally injected into the one eye (C57) and the same volume of vehicle (saline) injected into the contralateral eye. DHE (1 ul) was then injected intravitreally and both eyes imaged to detect ROS production using a SLO machine. Whereas no signals can be detected in the baseline levels in the both eyes (A, C), administration of rotenone induced stronger fluorescent signals of ROS production in the retina (D) compared to vehicle control (B), which was significantly different (E, $p<0.0001$).

FIG. 12C. The effects of PMA in producing ROS in mouse retina in vivo. PMA (50 ug/ml, 1 ul) was injected intravitreally into the one eye and saline (1 ul) into the contralateral eye. DHE (1 ul) was simultaneously injected for detecting ROS production. Similar to rotenone, PMA resulted in significantly higher levels of ROS production (D, E) than vehicle control (B, E), and no signal was observed in the both eyes before PMA injection (A, B).

FIG. 12D. The effects of Aβ25-35 on ROS production in vivo. DHE was intravitreally injected into the both eyes of a mouse to detect ROS production. Administration of Aβ25-35 (5 nmol) in the contralateral eye resulted in strong ROS fluorescent signals in the retinal ganglion cell layer (RGCL, D), compared to control (B) and baseline (A and C). Changes in fluorescence as shown in E with quantification of data allowing statistic analysis, which showed that Aβ induced a significant increase of ROS production in the retina compared to control (E, $p<0.0001$).

FIG. 13 shows that changes in $Ca^{2+}$ homeostasis can identified in retinal cells. This can be used as a marker in the present invention.

FIG. 13A Confocal imaging of Ca2+ response to Aβ25-35 (Abramov A Y et al. J Neurosci 23:5088-95, 2003) In a hippocampal coculture loaded with fluo-4, confocal imaging during the exposure to Aβ shows that the change in [Ca2+]c can originate as a focal change that diffuses through the cell and may be restricted to the subplasmalemmal space a, Time series of confocal images taken during a single [Ca2+]c transient response in an astrocyte. Note that the response begins with a focal rise in [Ca2+]c (arrowhead) followed by the slower spread through the cell. This is illustrated further in b, which shows a plot of the signal with time at four different locations in the cell (indicated color-coded on the inset image). The rapid rate of rise at the point of influx contrasts with the much slower increase seen deep in the cytosol of the cell. B, Series of images taken from another astrocyte during a response to Aβ25-35, again showing that the [Ca2+]c signal may be restricted to the periphery of the cell and fail to propagate through the cell. The first image of the sequence shows the raw data, whereas the subsequent images show the ratio of the image sequence with respect to the first image of the sequence.

FIG. 13B. The effects of Aβ25-35 on calcium signals in vivo in a mouse eye. Intravitreal administration of Fura red, a fluorescent calcium indicator, resulted in a faint calcium signal in the retina (B) compared to baseline (A). Ten minutes after Aβ25-35 (5 nmol) application (as shown D) however, a stronger fluorescent signal was detected in the RGCL (C). Quantitative analysis revealed that Aβ induced a significant increase in calcium signals in the retina, compared to pre-treatment (D, $p<0.001$).

Figure 13C:
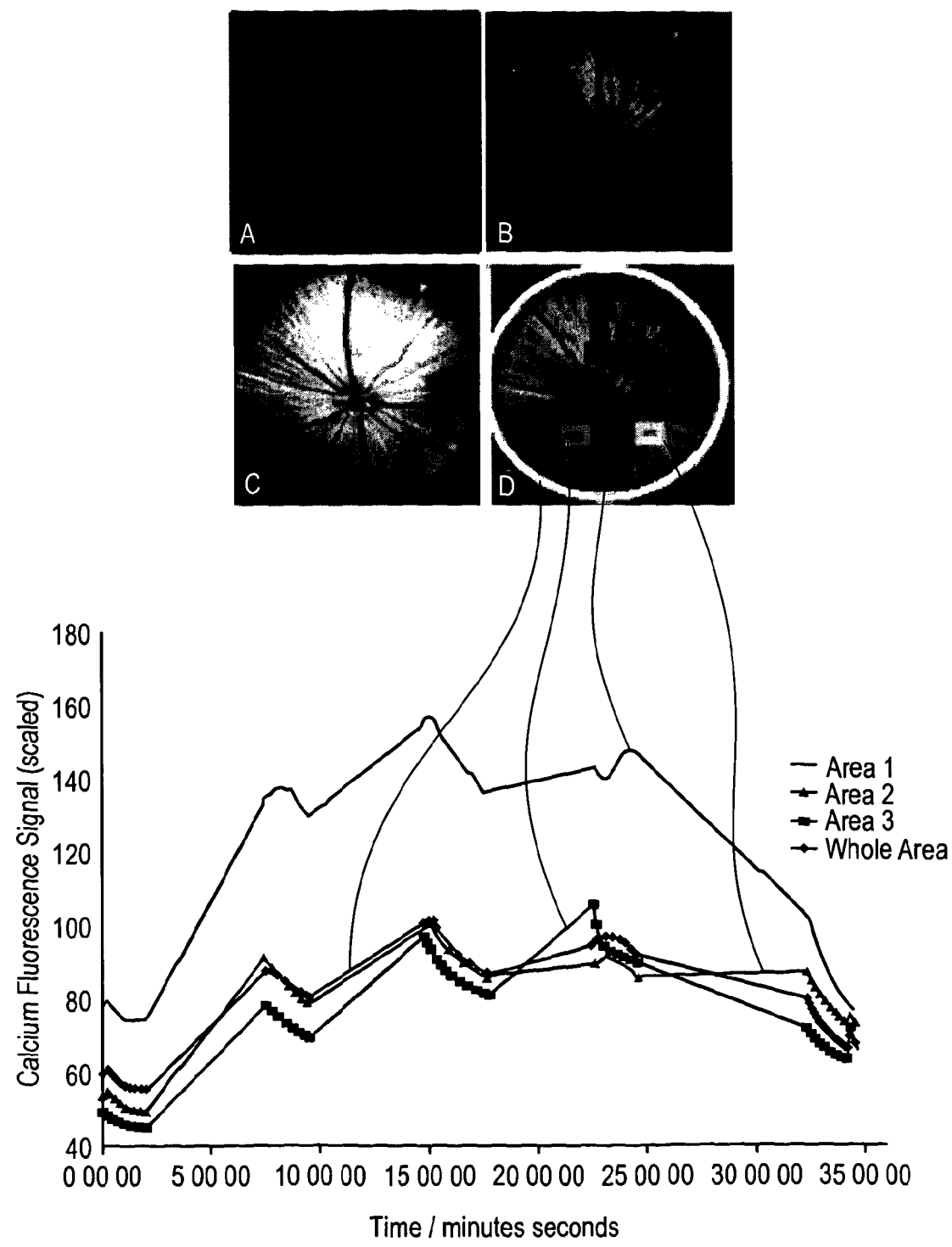

FIG. 13C Calcium transgenic mice with genetically-encoded fluorescent Ca2+ indicator proteins (FCIPs) were imaged in vivo. Aβ25-35-induced calcium transients in a calcium transgenic mouse eye. Compared to baseline (A), Aβ25-35 intravitreal administration induced an immediate fluorescent calcium signal in the retina (B) and the signal appeared to increase significantly minutes later (C). Analysis of the fluorescent signal after Aβ injection at t=o, is shown graphically with fluorescence seen in the areas Identified by coloured boxes in inset (D,E).

FIG. 14 shows that changes in $Ca^{2+}$ homeostasis can be used as a marker in the present invention to monitor response to treatment.

Figure 14A:
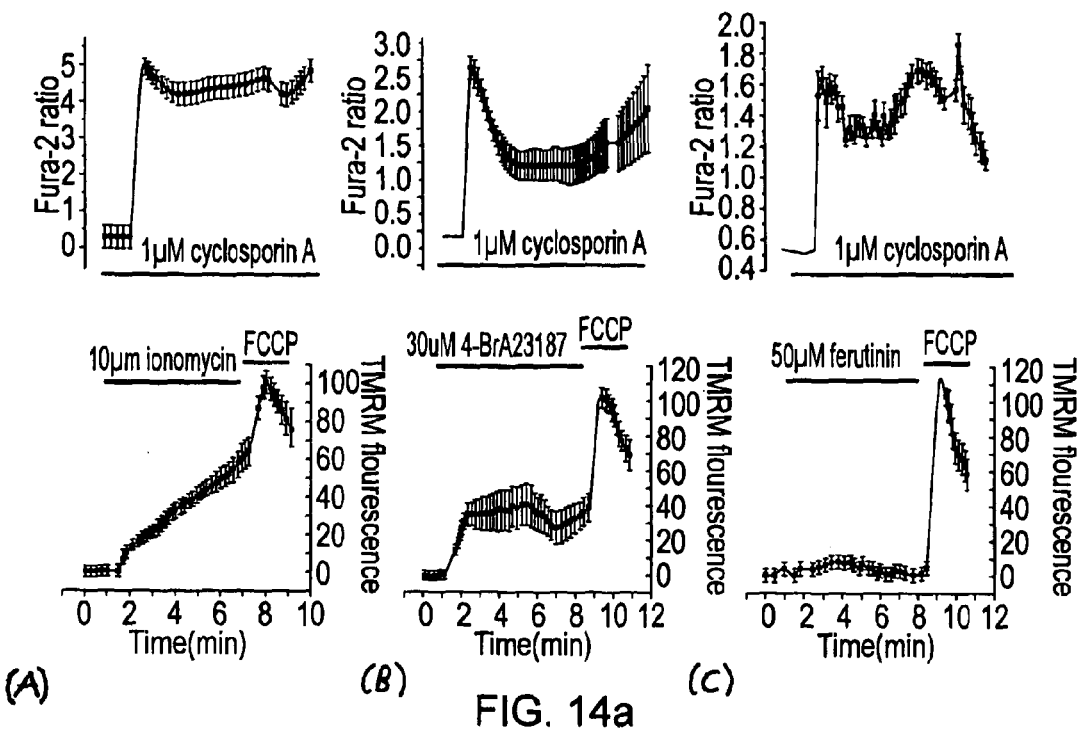

FIG. 14A Effect of cyclosporin on ionophore-induced mitochondrial depolarisation and [Ca2+]c. (Abramov A Y et al. Cell Calcium 33:101-12, 2003). Live cell imaging showing simultaneous measurement of [Ca2+]c. with Fura-2 and TMRM (a membrane permeable cationic fluorophore) in HepG2 cells pre-incubated with 1 um CsA for 30 min and during experiments. (A) 10 um ionomycin (B) 50 um 4-BrA23187 (a neutral ionophore), (C) 50 um ferutinin (an electrogenic naturally occurring ionophore, believed to induce MPTP opening)). CsA completely prevented mitochondrial depolarisation induced by ferritinin.

Figure 14B:
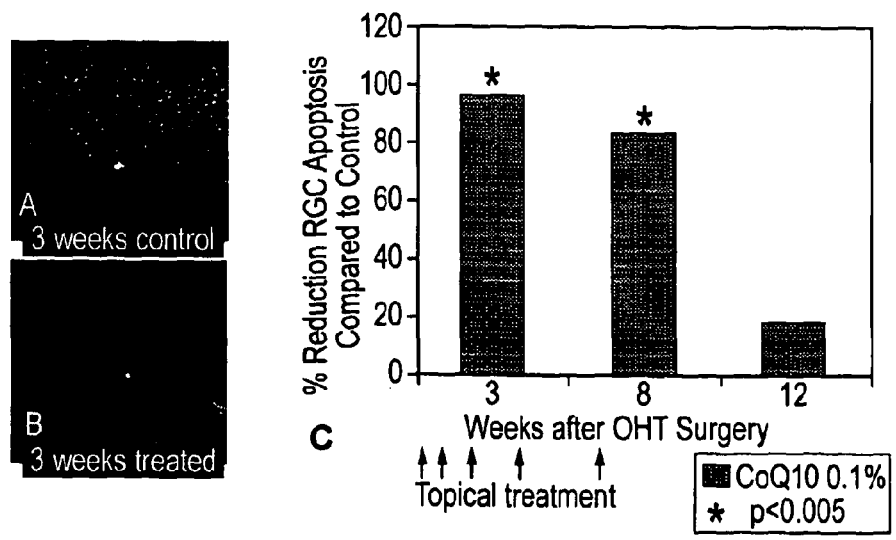

FIG. 14B DARC in vivo imaging of OHT rat eyes at 3 weeks after elevated intraocular pressure (IOP) showing increased RGC apoptosis (white spots) in Control (A) compared to CoQ10-treated (B) eyes. (C) shows the percentage reduction in RGC apoptosis in OHT model of experimental glaucoma with treatment with topical CoQ10 compared to control (orange arrows indicate topical treatment on Day 0, 1, 7, 21 & 42). CoQ10 significantly reduced RGC apoptosis at 3 & 6 weeks.

Figure 14C:

FIG. 14C Histological cross sections of retina stained for Cyclophilin D. Normal (A), OHT (B) and CoQ10-treated (C) rat eyes showing increased Cyophilin D (CyD, red, Vector red; blue, haematoxylin nuclear stain) in CoQ10-treated retina in RGC layer 3 weeks after induction of OHT, suggesting CoQ10 increases CyD.

Figure 14D:
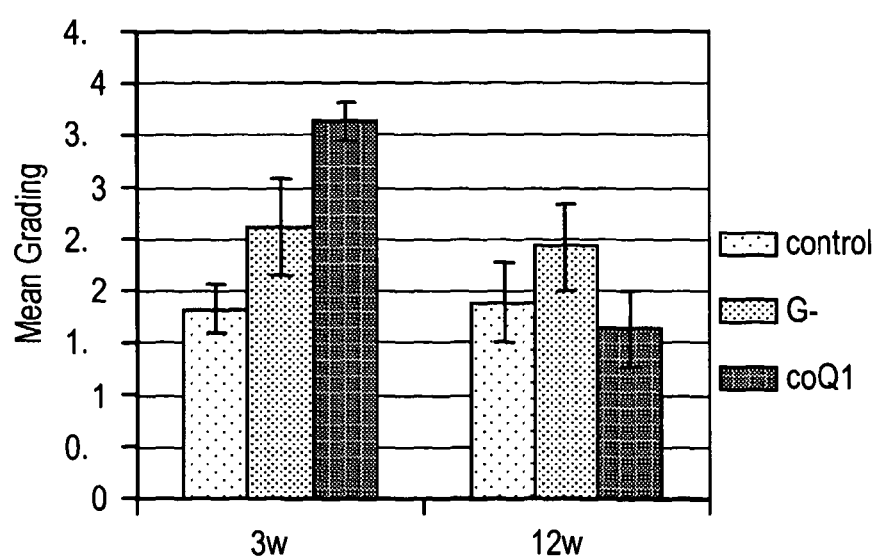

FIG. 14D Graphs showing mean histological grading score of retinas from control, OHT and CoQ10-treated OHT rat eyes at 3 and 12 weeks after elevated IOP, showing a significant increase in CyD in CoQ10 eyes at 3 but not at 12 weeks. This suggests that there is an association in the reduction of RGC apoptosis seen in CoQ10 eyes and the level of RGC apoptosis, FIGS. 15 *a* to *f* show image processing steps for cell-labelling.

DETAILED DESCRIPTION

Materials and Methods

Animal Models

For our investigations in rats, the inventors used established models of retinal neuronal apoptosis (Cordeiro et al., 2004). All procedures complied with local and national regulations and were performed under general anaesthesia. Adult Dark Agouti (DA) rats, 150-200 g, were used in all rat experiments.

For the experimental glaucoma studies, the inventors used an established model of ocular hypertension. 18 rats underwent surgery to elevate intraocular pressure (IOP) by injection of hypertonic saline solution (1.8 M) into two episcleral veins as previously described (Cordeiro et al., 2004). Contralateral, unoperated eyes acted as controls. Animals were imaged at 0, 3, 8, and 16 weeks, with at least 3 animals at each time point being killed for histology immediately after imaging. A subgroup of animals (n=4) was treated at the time of surgery with the NMDA antagonist MK801 (0.6 nmol; Tocris Cookson Ltd, Bristol UK). These animals were imaged at 3 weeks and then killed for histology.

For analysis of staurosporine-induced RGC apoptosis, 14 DA rats received 0.5 μg of intravitreal staurosporine (SSP) in 5 μl phosphate-buffered saline (PBS); both Sigma Aldrich UK, to induce RGC apoptosis as previously described (Cordeiro et al., 2004). Animals were imaged immediately for up to 6 hours, after which they were killed for histology.

For the analysis of Abeta, freshly made $A\beta_{25-35}$ (Sigma-Aldrich, 3.40 nmol) (Dahlgren et al., 2002) was intravitreally injected into C57 mice (n=10) (Maass et al., 2007). Animals were imaged at 72 hours. For AD 3× Tg-AD studies, 4 eyes (all female, 14 months) with 2 eyes from aged control mice (PS1KI; female, 18 months) were assessed. 3× Tg-AD and control PS1KI mice were obtained from a colony (maintained at CeSI) established after a generous gift of Frank Laferla. Intravitreal phorbol myristate acetate (1 μl of 10 μg/ml) was administered to left eyes of 3× Tg-AD animals, at the same time as annexin V and PI.

Fluorescent In Vivo Labeling

To identify RGC, retinas were retrogradely labelled using different agents in pilot studies by their application to both superior colliculi, as previously described (Cordeiro et al., 2004). Pilot studies identified DiI (1,1'-dioctadecyl-3,3,3',3'-tetramethylindocarbocyanine perchlorate, 10% solution; Molecular Probes, Cambridge Biosciences, UK) as being better than DiAsp (4-(4-(didecylamino)styryl)-N-methylpyridinium iodide (4-Di-10-Asp), Fluorogold or Rhodamine B. DiI was applied 10 days before all rat treatment procedures detailed above. DiI is a long-chain dialkylcarbocyanine lipophilic neuronal tracer, which does not affect cell viability, development or basic cellular physiological properties (Honig & Hume, 1989).

Using a method the inventors have recently described, rats were given 2.5 μg of intravitreal Alexa Fluor 488 labelled annexin V in 5 μl PBS for identification of RGC apoptosis, 2 hours before in vivo imaging (Cordeiro et al., 2004). For mice, the inventors used 1 μl of a 0.25 mg/ml solution of IR-labelled annexin (Annexin-IR) in intravitreal injections as previously described (Schmitz-Valckenberg et al., 2008).

In order to identify necrotic RGCs in rats (2 μl) and mice (1 μl), propidium iodide (PI; 0.4 mg/ml, 1% solution, Sigma-Aldrich, Dorset UK) was administered intravitreally at the same time as annexin, 2 hours before in vivo imaging. PI intercalates into nucleic acids, binding to double-stranded DNA, but only crosses the plasma membrane of non-viable cells. Cells that have lost membrane integrity are thus identified by fluorescent red PI staining throughout the nuclei.

Imaging

All rats had in vivo retinal imaging performed at regular and set intervals after experimental treatment, using a prototype Zeiss confocal scanning laser ophthalmoscope (cSLO), as previously described (Cordeiro et al., 2004; Maass et al., 2007). Imaging was performed under general anaesthesia with animals being held in a stereotaxic frame, with their pupils dilated. Different lasers and filters were used for the different fluorochromes: for excitation of Alexa Fluor 488 an Argon laser wavelength of 488 nm, and a solid state photodetector with a 521 nm cut-off filter and a 550 nm cut-on filter was employed; for DiI, a diode-pumped crystal green laser with a wavelength of 532 nm was used with 550 nm cut-off and 600 nm cut-on filters; the same laser was used for PI visualization but with a 650 nm cut-off. The cSLO used in this study is the same as described previously and with modifications complying with the established standards for safety and light exposure (Cordeiro et al., 2004; Schmitz-Valckenberg et al., 2008). The inventors have developed purpose-written software to allow optimal processing of low light fluorescent signals, which has greatly aided our live cell imaging (Cordeiro et al., 2004). Monochrome images from each area were acquired using the appropriate laser set-up and colourised. Three-color images were produced by combining each of the grayscale images from the cSLO into the red (PI), the green (annexin 488), and the blue channels (DiI) of an RGB color image. Images were processed in this way because red, green and blue (RGB) colour is universally accepted as the most informative method for displaying co-localization. The ImageJ Intensity Correlation Analysis Plugin was applied to generate colocalization scatter plots and colour thresholds (Li et al., 2004). Colour and raw scatter plots of annexin and PI fluorescence intensity were constructed, so data could be analysed in a similar manner to data derived by in vitro FACS analysis. Separation of the different phases of cell death according to whether they were as annexin V positive (early apoptosis), annexin V and PI double positive (late apoptosis) and PI positive (necrosis) was enabled by the adoption of thresholds set automatically by the plugin for each analysis. Fluorescence intensity counts derived from raw scatter plots were used to quantify each phase of cell death.

In mice, the inventors used instrumentation as previously described (Maass et al., 2007; Schmitz-Valckenberg et al., 2008), with a modified cSLO (Heidelberg Retina Angiograph 2, Heidelberg Engineering, Dossenheim, Germany) and a wide-field lens (55°). The fluorescein angiogram (488 nm argon laser) and indocyanine green (IR 790 nm diode laser) settings were used to detect PI and IR-labelled annexin respectively. The same software was used to analyse video sequenced images as described before with whole retinal monochrome images from each eye recorded and colourised. Dual-color images were produced by combining each of the grayscale images from the cSLO into the red (PI), and green (IR annexin) of an RGB color image.

Analysis

ImageJ software was used with specific plugins to create 3D surface plots, RGB projections, and analyse co-localization (JaCoP and Intensity Correlation Analysis). Graphical data for mean values were contrived with 95% confidence intervals, and comparisons across groups performed using ANOVA or student t-test for paired-eyes, with p<0.05 significance level.

EXAMPLES

The DARC Count

Figure 2:
FIG. 2 shows the DARC retinal image of FIG. 1 differentiating between "cells" and noise. Green spots with a threshold of area ≥10 indicate "cells"; red spots with areas <10 indicate noise.

The DARC retinal image an 'averaged' image is acquired from the original image using a software specifically developed for autofluorescence imaging (von Ruckmann et al., 1995; Wade & Fitzke, 1998) and a standard deviation of spots compared to background is created (FIG. 1). In order to eliminate background noise, spots with an area above a certain threshold, e.g. 10, are counted as "cells" and those with an area below the threshold indicate noise. The number of apoptosing cells obtained is known as the DARC count. In FIG. 2, there are 633 spots in total and 319 are identified as cells. Accordingly, the DARC count for this image is 319.

The DARC Pattern of Distribution

Figure 3:
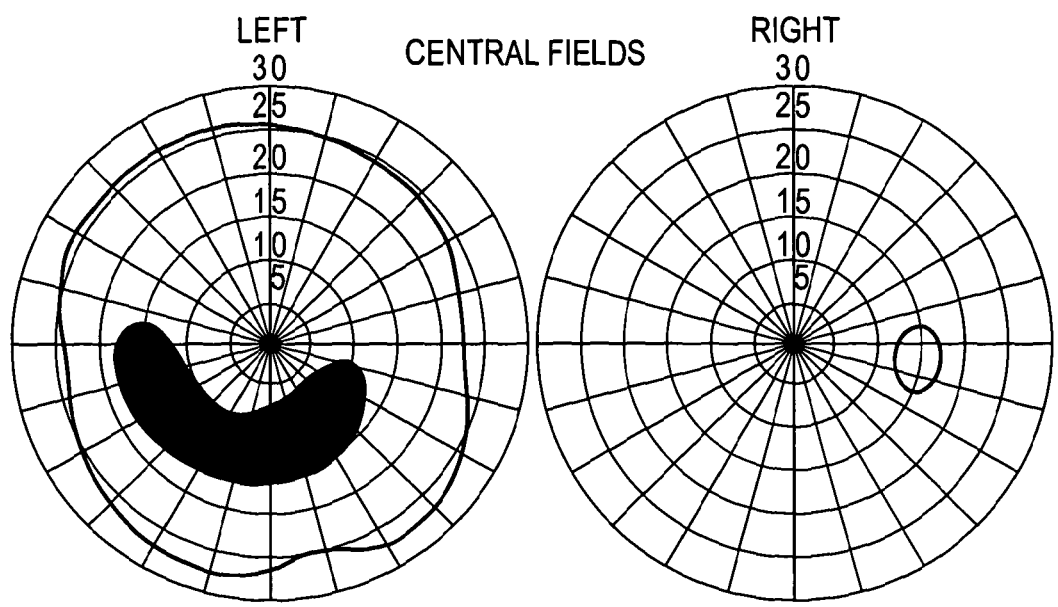
FIG. 3 shows an inferior arcuate scotoma (image taken from Clinical Methods The History, Physical and Laboratory Examinations, $3^{rd}$ Ed.)

A scotoma is an area of poor vision surrounded on all sides by relatively better vision. The arcuate fibers surround the papillomacular bundle, originating above, below, and temporal to it. Lesions of the arcuate bundle produce arcuate or cuneate-shaped scotomas and these are characteristic of glaucoma (FIG. 3).

In a similar manner, the distribution of apoptosing cells along the papillomacular bundle will enable the differentiation between different neurodegenerative diseases of the eye. For instance, glaucoma would have a focal pattern (typically arcute) of retinal nerve death following the papillomacular bundle, whereas diseases such as diabetic neurodegeneration would be diffuse.

Figure 4:
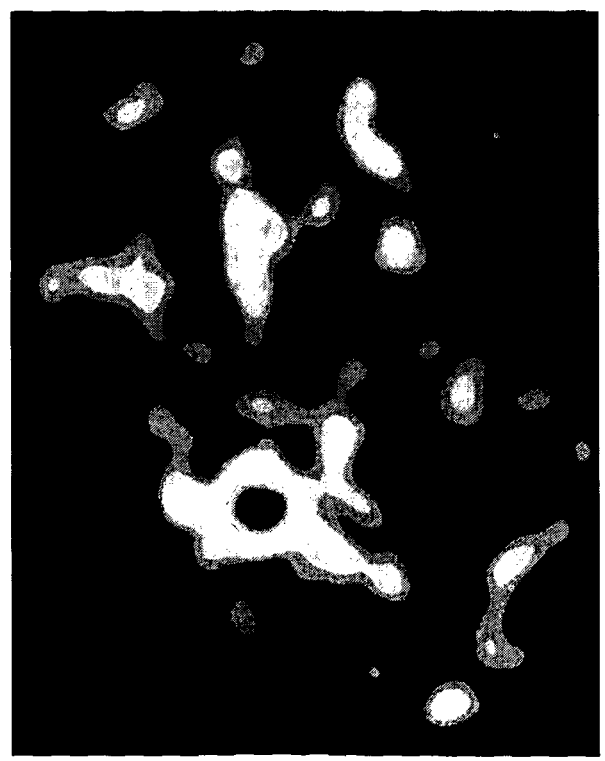
FIG. 4 shows a colour density map of a retinal image of FIGS. 1 and 2.

FIG. 4 shows a colour density map of the same image shown in FIGS. 1 and 2.

Customizing Imaging Equipment Enables Fluorescent Triple-Labelling Detection

To simultaneously detect three different fluorochromes the inventors first customized a prototype Zeiss confocal laser scanning ophthalmoscope (cSLO; Cordeiro et al., 2004) to enable detection of different emission wavelengths. The parameters used were based on well-established fluorescently tagged-cell markers selected to have distinct spectral properties and minimal overlap, and emitted light collection was optimised with appropriate filters (FIG. 5). Various cell death markers that are able to differentiate apoptosis and necrosis are well known to those skilled in the art. In vivo imaging of apoptosis is based on the targeting of marker molecules, such as initiator caspases (caspase-8 and -9), effector caspases (caspase-3 and -7), phosphatidylserine (PS), which is exposed on the outside of the cell membrane of apoptotic cells as a signal for phagocytosis, and phosphatidylethanolamine (PE), which is present on apoptotic cell surface and plays a regulatory role. Apoptotic markers include, but are not limited to, annexin V, C2A domain of synaptotagmin-I, duramycin, non-peptide based isatin sulfonamide analogs, such as WC-II-89, and ApoSense, such as NST-732, DDC and ML-10. In contrast, in vivo imaging of necrosis takes advantage of the loss of the cell membrane integrity allowing exchange of macromolecules between the intracellular and extracellular environment, which is not possible in viable cells. Necrotic markers include, but not limited to propidium iodide (PI), pyrophosphate, antimyosin, glucarate, hypericin and its derivatives, such as hypericin monocarboxylic acid and pamoic acid, such as bis-hydrazide-bis-DTPA pamoic acid. In the present study, for identification of apoptotic cells, the inventors used Alexa Fluor 488-labelled annexin V which has excitation/emission maxima of 495/519 nm, with an argon laser and a solid state photodetector with a 521 nm cut-off filter and a 550 nm cut-on filter (Cordeiro et al., 2004); to identify necrotic and late apoptotic RGCs the inventors used PI, with excitation and emission maxima of 532 nm and 649 nm respectively, with detection using a diode-pumped crystal green laser with a wavelength of 532 nm, and a 650 nm cut-off filter on the photodetector. After empirical assessment of several different compounds, including DiAsp (4-(4-(didecylamino)styryl)-N-methylpyridinium iodide (4-Di-10-Asp), Fluorogold and Rhodamine B, the inventors determined that DiI was the most suitable RGC marker in our rat models, with excitation and emission maxima of 550 nm and 570 nm respectively. The same laser used for PI was used for DiI visualization but with 550 nm cut-off and 600 nm cut-on filters.

This system permitted multi-wavelength imaging with high resolution and sensitivity, and minimal bleed-through (FIG. 5). The filters were specifically chosen for the fluorochromes used, but in principle a diverse number of fluorescent markers utilized in a wide-range of established cell biology protocols could be studied with appropriate modification to the cSLO system—highlighting the use of the retina as a model to study in vivo cellular processes.

In Vivo Imaging Allows Longitudinal Tracking of Changes in Cell Markers Over Time Having defined the functional parameters of the technology, the inventors next investigated its application in vivo using animal models of neurodegeneration. Staurosporine (SSP), a well-known non-selective protein kinase inhibitor, is routinely used as a potent inducer of neuronal apoptosis in in vitro assays (Belmokhtar et al., 2001). The inventors have previously established that SSP may be conveniently employed in vivo to induce a rapid and fairly synchronous wave of RGC apoptosis that is readily detected using annexin V (Cordeiro et al., 2004; Maass et al., 2007). The inventors therefore first studied the effects of SSP in rats in which RGCs had been retrogradely labelled with DiI, followed by intravitreal delivery of SSP, annexin V-488 and PI.

In this model, time-lapse video sequences (FIG. 6a-e and Supplementary Videos 1-2) of single retinal areas over 5 hours revealed a random distribution and appearance of apoptotic and necrotic cells, particularly highlighted by the 3D surface plot (Supplementary Video 2), and the average intensity projections of the time-lapse sequence shown in FIG. 6f-g (generated by ImageJ RGB Zprojector plugin). Graphical analysis of the image sequence histograms demonstrated that the average intensity profiles of annexin V and PI changed significantly over time (examples shown in FIG. 6h).

These results demonstrate proof of principle that this technique enables the tracking of changes in individual retinal cells in the same eye over time, with the ability to temporally and quantitatively analyse changes in fluorescence intensity. To our knowledge, this is the first demonstration of high-resolution multi-wavelength imaging used to visualise the death of single neurons in vivo.

Identifying Patterns of Tracked Single Cell Death Markers Over Time In Vivo

The inventors next assessed whether the multi-labelling of cells in vivo allowed the resolution of different patterns of apoptotic and necrotic cell death. Due to the rapid kinetics and predominantly apoptotic mode of cell death induced by SSP, the inventors again investigated simultaneous triple-labelling in rats. Although the precise kinetics of the onset of annexin V-positivity and the development of PI staining varied from cell to cell, single cell tracking allowed the natural history of the patterns of fluorescence to be delineated.

In this SSP model (Cordeiro et al., 2004) single cells were identified from stills, and a random sample (n=30) was selected according to whether they were DiI positive (i.e. white spots identifying single RGCs, FIG. 7a) and stained either with annexin V-488, PI or both. Video analysis of selected tracked individual cells fulfilling these criteria (artificially labelled as light blue spots in FIG. 7b) using ImageJ software and the Time Series Analyzer plugin allowed us to construct intensity profiles of annexin V and PI. From these profiles, it was found that typically three patterns of fluorescent labelling were observed, as illustrated in FIG. 7c which is a colour map showing the distribution of the cells and the staining patterns. Firstly, some cells were found to be labelled only with PI ("PI only", red spots, FIG. 7c); others were initially annexin V-positive and subsequently became PI-positive ("Annexin first", green spots, FIG. 7c), whilst others became positive for both dyes at approximately the same time ("Similar profiles", yellow spots, FIG. 7c). The patterns of fluorescent labelling appeared to be randomly distributed.

The tracking of annexin V-488 and PI staining in single cells is clearly shown in the magnified video stills illustrating representative cells displaying the specific patterns of fluorescent labelling (arrowed in FIG. 7 e-g "PI only"; i-k"Annexin first"; and m-o "Similar profiles") with corresponding graphs of signal intensity over time (FIG. 7 h,l,p). In each illustrative case, the intensity profiles of annexin V and PI changed significantly over time. The mean timings to peak intensity of this random sample (FIG. 7d) revealed that "PI only" cells tended to appear with significantly shorter kinetics than either the "Annexin first" or "Similar profiles" cells. In addition, cells that became annexin V-positive, invariably also became PI-positive, either within an hour or coincidentally.

These results provide evidence that neuronal cells in vivo display considerable heterogeneity with regard to the kinetics of necrotic and apoptotic cell death marker staining, and by inference also the relative timing of phosphatidylserine exposure (early phase apoptosis) and nuclear condensation (late phase apoptosis).

Assessing the Phases of Cell Death In Vivo

In vitro FACS analysis enables cells to be classified as being in early apoptosis (annexin V-positive only), necrosis (PI only) or late phase apoptosis (both annexin V- and PI-positive). To quantify the magnitude of late phase apoptosis in vivo, the inventors studied individual levels of annexin V, PI and their co-localisation using our recently developed Abeta model of RGC death (Guo et al., 2007). The advantages of this methodology are well-established in the field of cell biology, and provide a snapshot of the status of RGC death at any one time. The inventors also evaluated the effects of treatment with the NMDA channel blocker MK801, with the same analytical methods.

Using the Abeta model, the inventors assessed the effects of intravitreal Abeta ($A\beta_{25-35}$) which the inventors have recently demonstrated to induce RGC apoptosis in rodent eyes (Guo et al., 2007). Significant RGC death occurred 72 hours after intravitreal administration of 3.40 nmol $A\beta_{25-35}$ to the right eye, a time that from previous work the inventors had shown to yield peak levels of apoptosis (FIG. 8). The left eye of each animal was treated with intravitreal 0.40 nmol MK801 at the same time as Abeta. Wide-angle retinal images were recorded 2 hours following intravitreal annexin (green) and PI (red), as previously described (Guo at al., 2006). A typical image of an $A\beta_{25-35}$ treated right eye (FIG. 8a) compared to the left MK801-treated eye of the same mouse (FIG. 8b), demonstrates that MK801 treatment reduces the numbers of annexin V (green) and PI (red) positive cells.

To assess the relative levels of early apoptosis, late apoptosis and necrosis the inventors studied the co-localization of PI and annexin V using ImageJ software with the Intensity Correlation Analysis plugin (Li et al., 2004). Colour and raw scatter plots of annexin and PI fluorescence intensity were constructed from plugin-generated data for each animal. Corresponding scatter plots (blue) from the eyes shown in FIG. 8a-b are illustrated in FIG. 8c-d. The data were analysed in a similar manner to data derived by in vitro FACS analysis, with four quadrants (midlines shaded in colour overlay as red, green, blue and yellow) enabling separation of the different phases of cell death as annexin V positive (early apoptosis, green), annexin V and PI double positive (late apoptosis, yellow) and PI positive (necrosis, red). Thresholds were set automatically by the plugin for each analysis of each eye. The inventors then used fluorescence intensity counts from the raw scatter plots to quantify each phase of cell death. MK801 treatment clearly reduced the overall levels of cell death (Total), but more particularly the number of cells in late phase apoptosis and necrosis (FIG. 8e). Interestingly, there was a small increase in the number of early phase apoptotic cells (Anx+) in the MK801-treated eyes (FIG. 8e). Since these are destined to become Anx+/PI+, this suggests whilst the results generally support the neuroprotective role of NMDA antagonists in Abeta-induced neuronal cell death (Miguel-Hidalgo et al., 2002), it may be that the protective effects of MK801 appear transient due its single application in these experiments.

To further assess the analytical power of the technique, the inventors next investigated whether the level of oxidative stress in Abeta-treated eyes influenced the phase of cell death and whether this was possible to visualize in vivo. Live cell imaging of glial/neuronal cultures has suggested that Abeta increases neuronal oxidative stress by activating NADPH oxidase in microglia, an effect that is potentiated by phorbol myristate acetate (PMA) (Abramov et al., 2005). FIG. 8f-g are taken from the right untreated (F) and left PMA-treated (G) eye of an animal treated 72 hours previously with 3.40 nmol $A\beta_{25-35}$. PMA (0.016 nmol) or vehicle was administered at the same time as intravitreal annexin V and PI, with imaging performed 2 hours later. PMA increased the numbers of annexin V (green) positive cells (FIG. 8f,g), which was confirmed by the co-localization scatter plots (FIG. 8 h,i). Quantification of fluorescence in all animals revealed that PMA significantly ($p<0.05$) increased the overall levels of cell death in the Abeta model, but in particular the number of cells undergoing early phase apoptosis (FIG. 8j). These results support the hypothesis that PMA potentiates Abeta-induced ROS damage via predominantly apoptotic pathways (Abramov et al., 2005).

Using the same methodology, the inventors next compared the relative levels of cell death phases between the SSP and Abeta acute models of RGC death, at the time points where the inventors have previously shown peak RGC annexin V positivity to occur i.e. at 2 and 72 hours respectively (Cordeiro et al., 2004; Guo et al., 2007). Images were re-analysed for all treated animals using co-localization scatter plots and the same methodology as described above. FIG. 8k illustrates that both SSP and Abeta models exhibit similar patterns of cell death at the time of peak apoptosis. The cell death profiles in both models showed significantly more cells in the late phase of apoptosis ($p<0.05$) as opposed to necrosis or early apoptosis.

The Natural History of Cell Death in Chronic Glaucoma-Related Models

Having demonstrated the application of this technique in two acute models of RGC death, the inventors next investigated models of chronic retinal neurodegeneration, which more closely resemble human disease. Our group has previously characterized, using in vivo and histological profiling of RGC apoptosis, an experimental glaucoma rat model of chronically elevated intraocular pressure (OHT) (Cordeiro et al., 2004; Guo et al., 2006). RGCs were retrogradely labelled using previously described methods with DiI (Cordeiro et al., 2004; Guo et al., 2007) and animals imaged repeatedly following administration of intravitreal annexin V at different time points in order to generate time-lapse video sequences (FIG. 9 a-f and Supplementary Video 3). Assessment of intact labelled RGCs in the glaucoma model (identified by DiI, blue, FIG. 9a) revealed dramatic changes in single RGCs. As expected, when compared to the number of cells identified at baseline (FIG. 9b) and at 3 weeks (FIG. 9c), the number of labelled RGCs evident at 8 weeks was markedly reduced (FIG. 9d) after surgical-induction of elevated intraocular pressure (IOP). Analysis of apoptosis induction in these retinas revealed that those RGCs that were annexin V-positive at 3 weeks (FIG. 9e) had disappeared by 8 weeks (FIG. 9f), suggesting that a wave of apoptosis follows the initial IOP elevation insult, which is followed in turn by the clearance of dead cells.

We next analysed the time sequence of annexin V and DiI changes during this period. Using a similar method to that described earlier for FIG. 6, the inventors constructed a maximum intensity 3D projection of the time-lapse video sequences (supplementary video 3), using the Image J RGB Zprojector and JaCoP plugin. The projection enabled the quantitative assessment of maximal annexin V and DiI staining at each pixel in the same retinal area studied over time. Although there was a high overlap ratio of annexin V staining with DiI (0.63, confirming the presence of apoptosis at the level of the RGCs), there was a very low ratio (0.072) of DiI cells also positive for annexin V. This demonstrates that either only some RGCs were ever annexin V-positive and that apoptosis is not the only pathway responsible for cell death in this model, or that annexin V positivity is transient (as shown in FIG. 7).

The inventors then investigated the presence of apoptotic and necrotic cells using PI and annexin V. At 3 weeks in the OHT model only a small proportion of RGCs were identified in early apoptosis compared to late apoptosis, as seen in a typical image in FIG. 9g. Quantification of cell death phases was performed using co-localisation scatter plots described previously. There was a significant ($p<0.05$) increase in cells in late phase apoptosis compared to either necrosis or early phase apoptosis (FIG. 9I). Indeed, most labelled cells were in late phase apoptosis (Anx+/PI+), with relatively few cells exhibiting the diagnostic markers of necrosis (PI+) or early phase apoptosis (Anx+). This distribution of dying cells is broadly similar to that seen in both the SSP and Abeta models (FIG. 8k) at the time of peak apoptosis.

The inventors next assessed whether neuroprotective treatment altered the relative numbers of cells in each of the cell death phases, using the NMDA antagonist MK801, which the inventors have previously shown to be effective in this model (Guo et al., 2006). Treatment with MK801 at the time of IOP elevation significantly reduced the numbers of both annexin V and PI positive cells (FIG. 9h). Co-localization scatter plot analysis showed a significant reduction of total cell death markers ($p<0.05$), and specifically a significant reduction in both late phase apoptosis and necrosis, compared to untreated OHT eyes at 3 weeks after elevated IOP induction.

Assessing Phases of Cell Death in the Alzheimer Triple Transgenic Model

There is growing evidence of retinal involvement in AD, with the demonstration using histological techniques that RGC apoptosis occurs in double transgenic AD models (Ning et al., 2008; Shimazawa et al., 2008) In order to determine whether phasing of RGC death could be assessed in vivo in another model of chronic neurodegeneration, the inventors next applied our technique to a triple transgenic AD model (3× Tg-AD). This is an increasingly utilized model of AD, which over-expresses APPSwe, and tauP301L, as well as carrying a PS1M146V knock-in mutation, and is currently the only existing transgenic model with both Abeta and tau neuropathology (Sensi et al., 2008). An accumulation of intraneuronal Abeta occurs early, which decreases as extracellular plaques are deposited, similar to the development of disease and in brains of patients with Down syndrome (LaFerla et al., 2007).

Previous transgenic studies (Ning et al., 2008; Shimazawa et al., 2008) have demonstrated that in the double AD APP/PS1 mouse line, the level of RGC apoptosis increased with age, being more preponderant at 27 than 7.8 months. However, in these studies aged (27 month) wild type congeners were not assessed. FIG. 10a demonstrates the typical appearance of the eye of a 14-month 3× Tg-AD imaged at 2 hours after intravitreal PI and annexin-IR alongside the similarly imaged eye of an 18-month control (PS1KI transgenic mouse that shows no Abeta and tau neuropathology (Oddo et al., 2003)) (FIG. 10b). To quantify the levels of the different phases of cell death, the inventors again used data generated from co-localization scatter plot analysis, which showed significantly more RGCs in the phase of early apoptosis ($p<0.05$, green, Anx+) and less necrosis ($p<0.05$, red, PI+) in 3× Tg-AD compared to aged control (FIG. 10c). These data show that whilst a low level of apoptotic and necrotic cell death occurs as a correlate of normal healthy aging in mice, in AD mice there is a significant increase in the relative numbers of RGCs in early phase apoptosis.

The inventors next investigated whether oxidative stress in AD eyes influenced the phase of cell death and whether this could be visualized in vivo. As intraneuronal Aβ accumulation and extracellular Abeta plaques are characteristics of this model (LaFerla et al., 2007), the inventors hypothesised that the addition of PMA would reveal whether the level of Abeta in this transgenic mouse is sufficient to modulate the retinal response in vivo (Abramov et al., 2005). The inventors therefore compared the effects of PMA in 14-month 3× Tg-AD animals (FIG. 10d) and control aged animals (FIG. 10e). PMA appeared to increase the level of annexin staining in the treated eyes of both animals. However, quantification revealed that although PMA treatment significantly increased early phase apoptosis in both control and 3× Tg-AD eyes ($p<0.05$, FIG. 10f-g), the magnitude of the increase was far less in the control eyes compared to 3× Tg-AD (30.3% in aged control, 61.4% in 3× Tg-AD). PMA also decreased late apoptosis ($p<0.05$) in the 3× Tg-AD model and necrosis ($p<0.05$) in the control eyes.

These findings show that PMA stimulates a higher rate of early phase apoptosis (annexin V staining alone) in 3× Tg-AD animals, and are consistent with the data in FIG. 8 showing a similar effect of PMA in the model of acute RGC death mediated by Abeta.

Image Processing for Cell-Labelling

As mentioned above, it is advantageous to be able to overlay one image on another and to be able to identify and follow apoptosis in specific cells.

Stage 1. Pre-Processing

The luminance and/or contrast of the regions constituting "mosaic" images can be inhomogeneous and this is very problematic for image-processing that relies on filter+threshold techniques (as is typical in cell biology). To deal with this we employ a local-luminance & local-contrast "gain control" (novel element #1) that minimises coarse-scale luminance/contrast fluctuations while retaining fine detail. This process consists of computing the mean and standard deviation of the grey levels in the locale of a given pixel and converting the pixel luminance into an effective luminance "z-score". Specifically, the Gaussian-weighted mean luminance is a Gaussian blurred version of the original $$\mu = G_s \otimes I \qquad 1.$$

where I is the source image and $G_s$ is a two-dimensional Gaussian filter (standard deviation, s). The Gaussian-weighted standard deviation can be computed as follows:

$$\sigma = \sqrt{G_s \otimes I^2 - \mu^2} \qquad 2.$$

and the final pre-processed image is then:

$$P = \frac{G_s - \mu}{\sigma}. \qquad 3$$

Figures 15A, 15B, 15C, 15D:
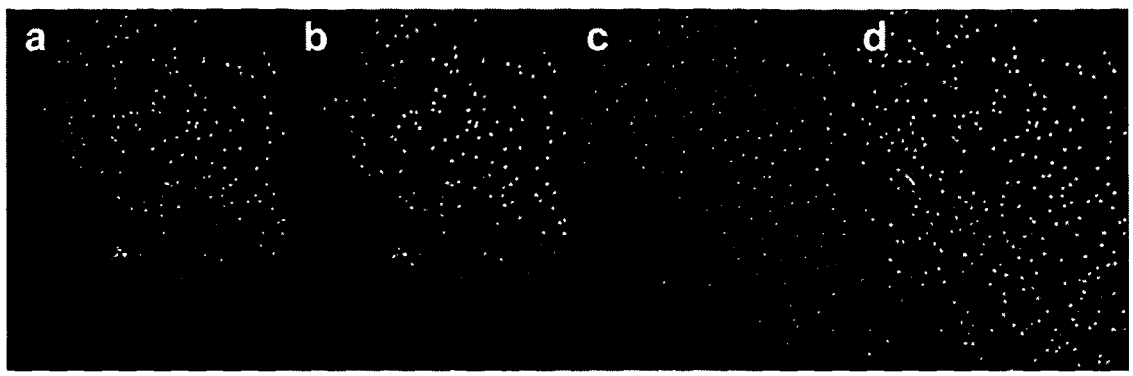
Figure 15E:
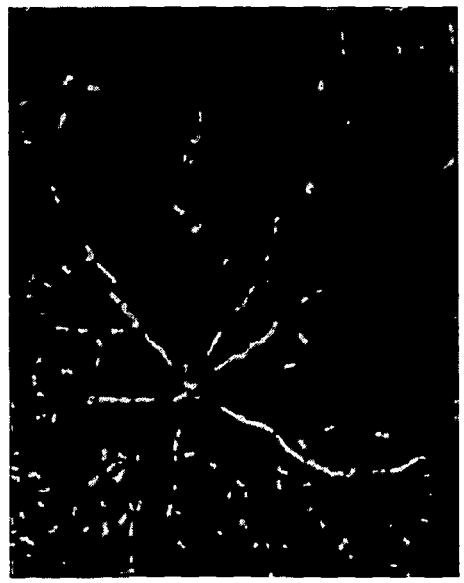

This image is then processed with a conventional Laplacian-of-Gaussian ($\Delta^2 G_1$) band-pass filter (with standard deviation, t) to highlight high-energy isotropic image-structure. The advantage of pre-processing is illustrated in FIG. 15. FIG. 15a is the original image and 15b the result of filtering it with the $\Delta^2 G_1$ filter. Note the weak (low-contrast) filter-responses in the lower left portion of the image. FIG. 15c shows the pre-processed version of FIG. 15a (generated with Eqs 1-3) and FIG. 15d a Laplacian filtered version of the pre-processed image. Note that the filter response is now much more spatially uniform than in 1b and that candidate vasculature and cell-structure across is now visible across the whole image, and will remain so after global thresholdig (used routinely, and below, to isolate discrete image structure).

Stage 2. Cell Identification

To label image structure as cells we first apply standard image-thresholding to the filtered images. We then employ "blob-analysis" on the isolated regions that result to compute their length along major ($L_{maj}$) and minor ($L_{min}$) axes length, their area (A) and their centroid ($[C_x, C_y]$). We then perform a novel categorisation of image structure based on these estimates. In the image in FIG. 15e we have categorised blobs as cells (red), vessels (green) or noise (blue), based on the following criteria: For noise: $A < A_{min}$, and for vessels: ($L_{maj}/L_{min}$)>$Aspect_{min}$. All other features are classed as cells. This exclusion of non-cell structure using combined size and aspect-ratio criteria is novel.

Stage 3. Cell Density Analysis

Figure 15F:
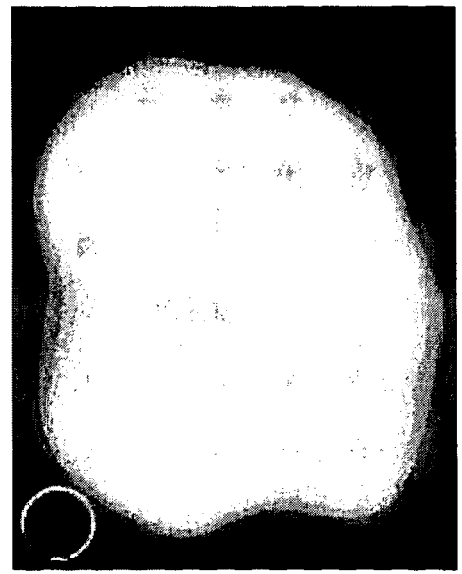

The final stage of processing uses estimates of each cell's location ($[C_x, C_y]$) to calculate cell-density maps. For any given point in an image we generate an estimate of the (Gaussian-weighted) mean number of cells falling within some locale surrounding the point. FIG. 15f is the density-map resulting from such analysis of the cell-image in the upper right. The radius of the ring (inset) indicates the size ($\pm 1\sigma$) of the Gaussian window used to weight density estimates.

Examples of Glaucoma Treatments

Glaucomatous RGC Apoptosis

In chronic glaucoma RGC apoptosis appears to be an early event (Kerrigan et al., 1997; Quigley, 2005; Quigley et al., 1995), with several mechanisms implicated in the pathogenesis of apoptotic RGC death in glaucoma, although a single causative mechanism has yet to be identified. Even though IOP may be viewed as a direct inducer of RGC stress and apoptosis (Guo et al., 2005; Kwon et al., 2009), damage to RGCs can occur in the presence of "normal" IOP (Sommer, 1989). Glaucoma appears to be of a multifactorial nature with complex genetic and environmental factors (Fingert et al., 1999; Libby et al., 2005; Mabuchi et al., 2007; Ray et al., 2003). In conditions of elevated IOP, mechanical stress on the lamina cribosa can lead to initial axonal degeneration, as suggested by Howell et al using the DBA/2J mouse model of glaucoma. This study also suggested that it is possible to protect RGCs against such damage using the Wallerian degeneration slow allele, which allowed functional protection from glaucoma in the D2.Wld mouse model (Howell et al., 2007).

Several other stress inducer factors have been identified such as tissue hypoxia (Kaur et al., 2008; Tezel et al., 2009), and glial cell activation (Lebrun-Julien et al., 2009). Mechanisms believed to initiate the apoptotic cascade in glaucoma and therefore potential targets for neuroprotection, are summarized in Table 1. These include: excitotoxicity (Dreyer et al., 1996; Guo et al., 2006; Osborne et al., 1999; Salt and Cordeiro, 2006), mitochondrial dysfunction (Mittag et al., 2000; Tatton et al., 2001; Tezel and Yang, 2004), protein misfolding (Guo et al., 2007; McKinnon et al., 2002a; Yoneda et al., 2005), oxidative stress (Ko et al., 2005; Tezel, 2006), inflammation (Tezel et al., 2001; Tezel et al., 2007) and neurotrophin deprivation (Cui and Harvey, 1995; Rudzinski et al., 2004). For a comprehensive review of mechanisms of RGC injury see (Qu et al., 2010).

The potential neuroprotective strategies included in this article, have been selected according to evidence in relation to glaucoma and/or other neurodegenerative conditions. Hence, only those therapies where a mechanism of action has been identified, and the agent used shown to modulate the mechanism have been included.

The various proposed mechanisms of RGC cell death have been investigated through the use of a variety of both in vitro and in vivo models, as shown in Table 1. The advantages, disadvantages and how closely these different models correlate to primary open angle glaucoma (POAG) in man, have recently been the focus of some comprehensive reviews (Johnson and Tomarev, 2010). It is important to recognize that there is still no perfect model of glaucoma, and translating results from preclinical to clinical studies is often problematical.

Neuroprotection and Excitotoxicity

Excitotoxicity is the pathological process by which RGCs and other neuronal cells die as a result of excessive extracellular glutamate (Choi, 1992; Doble, 1999; Olney, 1969). Glutamate released from the apoptotic cell can trigger necrotic death of surrounding cells that have been spared from the original insult, initiating a cascade of autodestruction, further cellular injury and death (Casson, 2006; Cheung et al., 2008; Osborne et al., 1999). Several studies have confirmed the neurotoxic effect of glutamate in the retina (Gross et al., 1999; Hyndman, 1984; Kawasaki et al., 2000; Luo et al., 2001), whilst others have suggested glutamate-mediated RGC injury and death in glaucoma (Brooks et al., 1997; Dreyer et al., 1996; Guo et al., 2006; McIlnay et al., 2004; Moreno et al., 2005; Salt and Cordeiro, 2006).

Modulation of the NMDA receptor has constituted a major area of research in glaucoma neuroprotection (Dong et al., 2008; Guo et al., 2006). In vivo and in vitro studies have suggested that blocking both the NMDA and the non-NMDA receptors simultaneously offers optimal protection against ischemic neurodegeneration (Leinders-Zufall at al., 1994; Mosinger et al., 1991). There are several anti-excitotoxic drugs that have been investigated in vivo and in vitro, that exert their neuroprotective actions by overcoming the glutamate-induced excitotoxicity as outlined in Table 1.

The most prominent of the NMDA receptor antagonists are MK801 and memantine. MK801, also known as (+)-5-methyl-10,11-dihydro-5H-dibenzo[a,d]cyclohepten-5,10-imine maleate, is a non-competitive antagonist of the NMDA receptor and has demonstrated neuroprotective potential in the CNS for many years (el-Asrar et al., 1992; Foster et al., 1988; Tamura et al., 1993).

MK-801 has also been found to protect RGCs both in vitro (Tsuda, 2004) and in vivo in the optic nerve injury model (Russelakis-Carneiro et al., 1996), the laser-induced retinal injury rat model (Solberg et al., 1997), and in hypertensive rat models (Chaudhary et al., 1998; Guo et al., 2006). Work on the experimental model of high IOP-induced retinal ischemia verified the neuroprotective effect of MK801 to be mediated through decreasing Bad expression (Russo et al., 2008). The effect of MK-801 in vivo on RGC apoptosis in a staurosporine-induced retinal toxicity model showed a reduction in the number of apoptotic RGCs in comparison to the controls (Guo et al., 2006). Unfortunately, MK801 is not used clinically because of its neurotoxic effect (Fix et al., 1993; Olney, 1969), which is believed to be due to high affinity to the NMDA receptors and its long dwell time in the channel (Lipton, 1993).

Memantine, also known as 1-amino-3,5-dimethyl-adamantane, is a three-ringed structural derivative of the anti-influenza drug, amantadine (Cheung et al., 2008). The additional amine (—NH2) and two methyl (—CH3) side groups are thought to be responsible for the increased residency with and affinity for NMDA receptors in relation to amantadine (Lipton, 2006). Memantine however exhibits strong voltage dependency with rapid blocking/unblocking kinetics, displaying weak potency during the normal synaptic transmission (Johnson and Kotermanski, 2006). Preliminary research into memantine as a neuroprotective agent in glaucoma demonstrated a reduction in NMDA-induced neuronal death in vitro (Pellegrini and Lipton, 1993). Subsequent in vivo results have shown decreased RGC loss in ischemic and hypertensive rat and mouse models (Kim et al., 2002; Lagreze et al., 1998; WoldeMussie et al., 2002), potentially via reduced cytochrome c release in the glaucomatous mouse retina (Ju et al., 2009). Treatment with memantine also resulted in a reduction in the shrinkage of neurons within the contra-lateral Lateral geniculate Body (LGB) relay (layers 1, 4, and 6), a major target for retinal ganglion cells (Yucel et al., 2006).

Memantine is Food and Drug Administration (FDA) approved for treating moderate to severe Alzheimer's disease (Reisberg et al., 2003) and is the only neuroprotective agent that has completed phase III clinical trial in patients with OAG. The trial showed that memantine was ineffective by the primary end point, with the variable mechanisms of retinal ganglion apoptosis being offered as an explanation (Osborne, 2008), although inadequate design of study and inappropriate end point could be additional reasons for this result.

DNQX is an AMPA receptor antagonist which has shown greater enhancement of RGC survival than MK-801 (Yoneda et al., 2003), whilst Riluzole has been shown to prevent or decrease pressure-induced apoptosis and enhance ERG wave recovery, highlighting the benefits of targeting multiple receptors in excitotoxic cell death.

Another potential neuroprotective pathway is through the mediation of acetylcholine (ACh) receptors, as shown by studies on the ACh esterase inhibitor, Galantamine, a drug clinically used in the treatment of AD. Galantamine potentially activates muscarine AchR, leading to RGC protection independent of IOP levels (Almasieh et al., 2010).

Mitochondrial Dysfunction and Therapy

Mitochondria are the main energy source inside cells and the primary site of ROS production, making it a major target for reducing oxidative stress. A decrease in mitochondrial membrane potential and an increase in membrane permeability have been implicated as a causative factor for RGC apoptosis in glaucoma (Mittag et al., 2000; Tatton et al., 2001; Tezel and Yang, 2004). Glaucoma-related stimuli such as hypoxia, TNF-α and oxidative stress can trigger the mitochondrial-mediated RGC death pathway. In glaucomatous stress, mitochondria buffer excess cytosolic $Ca^{2+}$ leading to intra-mitochondrial accumulation of $Ca^{2+}$, mitochondrial membrane depolarization and the production of ROS (Kristian and Siesjo, 1998). This has been shown to trigger release of apoptosis-inducing proteins, such as cytochrome c (Nickells, 1999), and CPP32 (caspase 3 activators) via opening of the mitochondrial permeability transition pore (PTP) (Hirsch et al., 1997; Marchetti et al., 1996).

Several compounds, outlined in Table 1, have been proposed to enhance the available energy within the cell and prevent mitochondrial depolarization.

$CoQ_{10}$, also known as Ubiquinone, plays an indispensible role in energy metabolism and displays the greatest potential as a neuroprotectant. It serves as a co-factor within the respiratory chain, carrying electrons and facilitating ATP production. It has been found to be highly effective as a neuroprotectant in animal models of neurodegenerative diseases such as Parkinson's disease, Huntington's disease and Friedreich's ataxia (Beal, 2003). Its neuroprotective effect, demonstrated on RGCs both in vivo and in vitro, is believed to be multifactorial (Nakajima et al., 2008; Nucci et al., 2007b), exerted not only through mediation of electron transport from complex I and II to complex III within the electron transport chain but also through its antioxidant properties, regulation of gene expression, and inhibition of the PTP (Cheung et al., 2008; Papucci et al., 2003).

Protein Misfolding Treatments

Amyloid deposits, consisting of aggregates of Aβ, are a characteristic feature of several neurodegenerative diseases such as Alzheimer's (Pepys, 2006), Parkinson's disease (Bayer et al., 2002) and mild cognitive impairment (Attems and Jellinger, 2006; Verwey et al., 2008; Villemagne et al., 2008). They have also been recently implicated in the pathogenesis of retinal damage (Shimazawa et al., 2008), age-related macular degeneration (AMD) (Johnson et al., 2002), and glaucoma (Goldblum et al., 2007; Guo et al., 2007; McKinnon et al., 2002a; Yoneda et al., 2005).

Drugs designated to target β-Amyloid (Aβ) include β-secretase inhibitors (BSI) such as N-benzyloxycarbonyl-Val-Leu-leucinal (Z-VLL-CHO) which has been found to reduce RGC apoptosis in vitro and in vivo (Guo et al., 2007; Yamamoto et al., 2004), as well as Congo red and Anti-Aβ antibodies (Guo et al., 2007; Lorenzo and Yankner, 1994). Triple therapy, targeting different stages of the Aβ pathway using BSI, Anti-Aβ antibodies and Congo red, showed a superior neuroprotective effect on RGC apoptosis in a rat ocular hypertension compared to singular treatments (Guo et al., 2007).

Also of interest with regards to protein misfolding are Heat shock proteins (HSPs), a group of specialized molecular chaperons that mediate various physiological functions inside cells. HSPs are up regulated in stressful conditions to restore normal structural integrity (Soti et al., 2005).

Several families of HSP have been implicated in neurodegenerative diseases (Pepys, 2006), and glaucomatous RGC apoptosis (Guo et al., 2007; McKinnon et al., 2002a), with increased levels of circulating autoantibodies to alpha-crystallins and HSP27 (Tezel et al., 1998), and increased immunostaining of HSP-60, HSP-27 in RGCs and the retinal blood vessels in glaucoma patients (Tezel et al., 2000). Systemic administration of Geranylgeranylacetone, an anti-ulcer agent, in the rat glaucoma model has been shown to increase the expression of HSP-72 with a marked reduction in RGC loss (Ishii et al., 2003), possibly through interactions with different protein kinases such as Akt kinase, and the inhibition of NF-KB (Neckers, 2007; Thomas et al., 1998). Drugs targeting protein misfolding in glaucoma are summarized in Table 1.

Therapy and Oxidative Stress

Oxidative stress is a pathological condition in which the rate of reactive oxygen species (ROS) production exceeds the body's anti-oxidative capacity. ROS are partially reduced highly reactive metabolites of molecular oxygen, containing an unpaired electron. ROS is generated primarily via the electron transport chain at relatively low levels during aerobic metabolism and plays an integral part in signal transduction. Ischemia, potentially by vascular dysregulation and reperfusion injury to cells are critical induces for oxidative stress (Flammer et al., 1999), leading to further ROS generation with ATP depletion and mitochondrial failure, triggering the caspase-dependent and caspase-independent mitochondrial cell death pathways (Murphy, 1999). The increased levels of ROS enhance lipid peroxidation, protein peroxidation (Siu and To, 2002) and single strand breaks in nucleic acids (Finkel, 1998; Finkel and Holbrook, 2000). ROS have also been found to induce Muller cell activation and dysfunction, generating further oxidative material (Neufeld and Liu, 2003; Tezel et al., 2003; Yuan and Neufeld, 2001).

The possible role of ROS in glaucoma has led to the investigation of multiple anti-oxidants as potential neuroprotective agents summarized in Table 1.

Melatonin, a potent naturally occurring antioxidant with free radical scavenging activity, displaying a critical role in aqueous humour circulation and shows potential as a neuroprotectant (Dubocovich et al., 1997; Sugden et al., 1997; Wiechmann et al., 1999; Wiechmann and Wirsig-Wiechmann, 1994). Its neuroprotective actions are believed to be mediated via multiple mechanisms including reducing single and double strand breaks in DNA (Sun et al., 2002), increasing Akt phosphorylation (Kilic et al., 2005a; Lee et al., 2006; Tajes Orduna et al., 2009), reducing NO-induced apoptosis (Siu et al., 2004) and inhibiting the mitochondrial transition pores and cytochrome c release (Andrabi et al., 2004; Jou et al., 2004; Kilic et al., 2004). Melatonin demonstrated neuroprotective effect on RGCs in vivo (Siu et al., 2004; Tang et al., 2006), it also protected rabbit retinal neurons in vitro (Cazevieille and Osborne, 1997). *Ginkgo Biloba* has been a part of traditional Chinese and Japanese medicine for many centuries (Evans, 2002; Samuelsson, 1999), for treating wide range of diseases including Alzheimer's disease (Kanowski et al., 1996; Kanowski and Hoerr, 2003; Yancheva et al., 2009), AMD (Rhone and Basu, 2008) and low-tension glaucoma (Quaranta et al., 2003). However, self-reported data from the 2002 National Health Interview study showed that there was no significant association between glaucoma patients and *Gingko biloba* use (Khoury et al., 2009). *Ginkgo biloba* extract (EGb761) contains two major compounds: 24% flavones glycoside and 6% terpenoids. Flavone glycoside is composed of quercetin, kaempferol and isorhamnetin glycosides (1-3) and the terpenoids are composed of A, B, C, D and J ginkgolides and bilobalide. The extract also contains organic acids such as kynurenic acid, 6-hydroxykynurenic Acid, vanillic acid, shikimic acid and glucuric acid (Hirooka et al., 2004). EGb 761 was found to be an excellent antioxidant, effectively inhibiting chemically induced apoptosis (Thiagarajan et al., 2002), as well as possessing both antiinflammatory and antiplatlet activating factor activities. EGb 761 also has a vasomodulatory effect on blood vessels, where it increases the ocular blood flow velocity (Chung et al., 1999). Furthermore, through inhibition of NO, platelet activating factor (PAF) and catechol-O-methyltransferase (COMT) it enhances the cerebral blood flow (Diamond et al., 2000). EGb 761 has demonstrated neuroprotectant effects on RGCs in a rat model of chronic glaucoma (Hirooka et al., 2004). Although the exact mechanism of the neuroprotective effect of EGb 761 is still unknown, mechanisms of reduced $Ca^{2+}$ dependant signal transduction, inhibition of the inducible pathological form of the NO synthase enzyme (iNOS) (Bastianetto et al., 2000b) and its possible affect on the Aβ pathway have all been proposed (Augustin et al., 2009; Bastianetto et al., 2000a).

Anti-Inflammatory and Immunological Strategies

Growing evidence in clinical and experimental studies strongly suggests the involvement of the immune system in glaucoma (Tezel et al., 2009). The sustained neuronal damage in glaucoma and other ischemic neurodegenerative conditions can trigger immune responses, leading to an excessive production of T-cells. Activated T cells subsequently attack antigens presented to its receptor by the major histocompatibility complex 9 (MHC 9). Up-regulation of the MHC class II molecules on rat glial cells and stimulation of T cell activation in cultured retinal and optic nerve tissue have been demonstrated (Tezel et al., 2007). In a rat model devoid of T cells due to thymectomy there was increased RGC death after optic nerve crush (Yoles et al., 2001). Furthermore, several research studies showed that, augmentation of immune system by passive transfer of T cells directed against myelin basic proteins or active immunization with the myelin derived peptide reduces RGCs loss after optic nerve injury (Schwartz, 2001). A similar finding has been reported in rats injected with activated anti-myelin basic protein T cells after partial optic nerve crush (Moalem et al., 1999; Moalem et al., 2000). The release of TNF-α, a potent proinflammatory cytokine, and its subsequent binding to the death receptor, TNF-α Receptor-1 (TNF-R1), triggers a caspase-dependant and a caspase-independent component of mitochondrial death promoting pathways. The TNF-α-R complex is able to recruit adaptor proteins that activate caspase 8, which in turn activates caspase 3 (Pastorino et al., 1996; Tezel et al., 2004).

TNF-α activities are mediated via interaction with two distinct receptors, the death domain-containing TNF-receptor 1 (TNF-R1) and the non-death domain-containing TNF-receptor 2 (TNF-R2) (Wajant and Scheurich, 2001). TNFR1 has been confirmed to mediate majority of TNF-α biological activity (Chen and Goeddel, 2002) and has been suggested to be involved in the neurodegenerative process of glaucoma (Tezel et al., 2001), neuronal cell loss and retinal ischemia (Fontaine et al., 2002), whereas TNF-R2 showed neuroprotective activity, reducing retinal ischemia (Fontaine et al., 2002).

Anti-inflammatory drugs, which target the TNF-α signaling pathway and displayed neuroprotective activity, have become an area of increasingly active investigation as outlined in Table 1.

The most promising anti-inflammatory drug is Copolymer-1 (Cop-1), also known as glatiramer acetate. It was approved by the FDA to treat the Multiple sclerosis (MS), Cop-1 is a low affinity synthetic non-encephalitogenic analogue to myelin basic protein, triggering a neuroprotective autoimmune response, by binding to MHC proteins and cross reacting with various T cell and CNS myelin. Cop-1 displayed neuroprotective activity on RGCs in vivo in the rat model of optic nerve crush (Kipnis et al., 2000), in animal models of high IOP (Bakalash et al., 2003; Ben Simon et al., 2006) and against glutamate-induced excitotoxicity (Schori et al., 2001). This neuroprotective effect is believed to be mediated by increasing the number of T-Lymphocyte in a rat model of glaucoma (Li et al., 2008).

Neurotrophin Deprivation

Neurotrophic factors, small molecular weight peptides, widely expressed in RGCs (Jelsma et al., 1993) have an indispensible role in growth, differentiation and survival. They include: nerve growth factor (NGF) (Kaplan et al., 1991), brain-derived neurotrophic factor (BDNF), Neurotrophins 4 and 5 (NT4 and NT5) (Barde et al., 1982; Berkemeier et al., 1991) and NT3 (Hohn et al., 1990; Rosenthal et al., 1990) which exert their effects through tropomyosin-related kinases (Trk). Several research studies demonstrated that the flow of the neurotrophic factors from the superior colliculus in the CNS to the RGCs is markedly reduced in the animal model of glaucoma, where both the retrograde and the antiretrograde axonal transport are compromised (Anderson and Hendrickson, 1974; Hayreh et al., 1979; Rudzinski et al., 2004). This leads to a reduction in neuronal trophic support, which in turn compromises neuronal survival and triggers apoptosis, as seen in RGCs following transection of the optic nerve (Berkelaar et al., 1994).

Various growth factors have successfully been investigated as neuroprotectants, as outlined in Table 1. NGF (nerve growth factor) has been identified in several studies as being neuroprotective in the Morrison's glaucoma model by reducing RGC apoptosis through topical application (Colafrancesco et al., 2010; Lambiase et al., 2009) as well as showing neuroprotective effects functionally in patient studies (Lambiase et al., 2009). Restoration of levels of the NGF receptor, TrkA have also been shown to be neuroprotective, providing additional evidence for a role for the NGF pathway in Glaucoma (Colafrancesco et al., 2010). The involvement of the pathway is further supported by evidence that a combination of NGF, TrkA agonists and $p75^{NTR}$ antagonists are neuroprotective (Lebrun-Julien et al., 2009).

However, sustainability remains a limitation. Following prolonged treatment with neurotrophins, RGCs exhibited a decrease in neurotrophin receptor expression reducing the effectiveness of the treatment. To overcome this problem a combination of neurotrophin treatment and gene therapy targeted to up regulating the receptors has been proposed (Cheng et al., 2002). Elevated IOP has been shown to result in transient up-regulation of TrkA, over-expression of truncated TrkC receptor and activation of the apoptotic P75 receptors (Rudzinski et al., 2004). Exogenous administration of neurotrophins enhances the phosphorylation of Trk receptors in the lamina cribrosa and optic nerve astrocytes (Lambert et al., 2004); whilst TrkB gene transfer protects RGCs in vivo in axotomy model (Cheng et al., 2002).

The field of gene therapy in neuroprotection is rapidly expanding (Liu et al., 2009; Wax and Patil, 1994). In glaucoma it is becoming a highly accessible approach (Harvey et al., 2006), because trabecular meshwork, ciliary epithelium, ciliary muscle, Müller cells and RGCs are all appropriate target structures for gene therapy, with various delivery systems having been tested (Borras et al., 2002).

A promising agent for glaucoma therapy is BIRC-4, also known as XIAP (IAP: inhibitors of apoptosis protein). Intravitreal injection of adeno-associated viral vector using chicken-β-actin (AAV-CBA) coding for human BIRC4 in the rat model of chronic glaucoma resulted in marked reduction in RGC apoptosis that was sustained for 12 weeks. This neuroprotective effect is believed to be mediated either via direct inhibition of caspase-3 and caspase-8, indirectly by maintaining the neurotrophin production from Muller cells and influencing aqueous humour circulation or a combination of both (McKinnon et al., 2002b).

Compounds with Multiple Mechanisms of Action: Brimonidine and Estrogens

Brimonidine tartrate 0.2% is known also as UK-14, 304, is a third generation $\alpha_2$ adrenergic agonist that draws the interest of many researchers in the field of neuroprotection. The neuroprotective effect of Brimonidine on RGCs has been demonstrated in vitro (Knels et al., 2008) and in vivo (Donello et al., 2001; Wheeler et al., 1999; WoldeMussie et al., 2001). The mode of action for Brimonidine however remains unclear with various proposed mechanisms. The positive effect of Brimonidine on RGC survival, that includes a reduction in their soma size in a rat model of ocular hypertension, is believed to be mediated through the attenuation of glutamate toxicity and or the up regulation of brain-derived neurotrophic factors (Hernandez et al., 2008). However, in a rat model of pressure-induced retinal ischemia, Brimonidine's neuroprotective effect was suggested to be mediated via the inhibition of the apoptotic cascade, possibly through the induction of anti-apoptotic genes such as bcl-2 and bcl-x, as well as extracellular-signal-regulated kinases (ERKs) and phosphatidylinositol-3' kinase/protein kinase Akt pathways (Lai et al., 2002). Whilst, Brimonidine's effect on RGCs in isolated rat retinas, as well as in vivo in rat and rabbit glaucoma models was shown to be mediated through the reduction of $\alpha_2$-adrenoceptor mediated reduction of intracellular cAMP (Dong et al., 2008).

A clinical trial assessing the non-IOP-related effects of Brimonidine, demonstrated reduced visual field deterioration in comparison to 360° laser trabeculoplasty (Gandolfi et al., 2004), whilst the results of Brimonidine treatment in the Low-Pressure Glaucoma Treatment Study are awaited (Krupin et al., 2005).

Estrogens, cholesterol derived steroid hormones, maintain the normal function of various organs, with estrogen receptors ERα and ERβ widely expressed in human and animal retinal tissues (Kobayashi et al., 1998; Ogueta et al., 1999). Estrogen has demonstrated neuroprotective effects in animal models of Alzheimer's (Simpkins et al., 2005) and other neurological diseases (Hoffman et al., 2006). The neuroprotective action of estrogen is believed to be mediated via multiple mechanisms; the binding with estrogen receptors ERα and ERβ (D'Astous et al., 2004; Dubal et al., 2001; Singer et al., 1996), activation of anti-apoptotic genes such as Bcl-2 and Bcl-x1 (Garcia-Segura et al., 1998), inhibition of mitochondrial oxidative stress (Razmara et al., 2007), inhibition of β-amyloid induced neuronal death, as well as stimulation of Akt/PI-3k pathway (Honda et al., 2000; Zhang et al., 2001). 17β-estradiol treatment of rat cortical neurons exposed to glutamate demonstrated increased neuronal integrity and function, mediated possibly by a reduction in the levels of caspase-3 and calpain (Sribnick et al., 2004). An estradiol analogue also demonstrated protective effects on the RPE (Dykens et al., 2004; Yu et al., 2005), and on the RGCs in vitro (Kumar et al., 2005) and in vivo (Nakazawa et al., 2006; Zhou et al., 2007).

Conclusion

Managing glaucoma patients can be clinically challenging to ophthalmologists due to the fact that most glaucoma patients are asymptomatic until substantial visual field loss occurs. During the last years however, progress has been made in understanding both the pathogenic and neuroprotective mechanisms involved in glaucoma and its treatment. Historically, however, translating preclinical and experimental drugs to patients has proven problematic due to the lack of good experimental models of disease; the narrow therapeutic index of the neuroprotective drugs due to undesirable side effects on the patients, as well as the lack of good clinical end points (Levin and Peeples, 2008). It is now believed that better clinical end points are necessary to access the new therapeutic agents. Unfortunately, the failure of the phase III clinical trial of memantine in glaucoma patients has reduced enthusiasm for neuroprotective trails (Osborne, 2008). However recent advances in imaging technology should provide clinicians and researchers with more reliable tools to access the efficacy neuroprotective agents (Cordeiro et al., 2004; Cordeiro et al., 2009). It is still not clear whether neuroprotection in glaucoma has a role in patients, and it is likely to remain unclear until there is a published, well-designed and successful glaucoma clinical trials showing evidence of a drug providing neuroprotection.

REFERENCES

Abramov & Duchen. The role of an astrocytic NADPH oxidase in the neurotoxicity of amyloid beta peptides. *Philos. Trans. R. Soc. Lond. B. Biol. Sci.* 360, 2309-2314 (2005).

Allen et al. Morphological and biochemical characterization and analysis of apoptosis *J. Pharm. Toxicol. Meth.*, 37(4), 215-228 (1997).

Belmokhtar et al. Staurosporine induces apoptosis through both caspase-dependent and caspase-independent mechanisms. *Oncogene* 20, 3354-3362. (2001).

Cordeiro et al. Real-time imaging of single nerve cell apoptosis in retinal neurodegeneration. *Proc. Natl. Acad. Sci. USA* 101, 13352-13356 (2004).

Dahlgren et al. Oligomeric and fibrillar species of amyloid-beta peptides differentially affect neuronal viability. *J. Biol. Chem.* 277, 32046-32053 (2002).

Guo et al. Alzheimer's disease and retinal neurodegeneration. *Curr. Alzh. Res.* 6 (2009).

Guo, L., et al. Targeting amyloid-beta in glaucoma treatment. *Proc. Nat.l Acad. Sci. USA* 104, 13444-13449 (2007).

Guo et al. Assessment of neuroprotective effects of glutamate modulation on glaucoma-related retinal ganglion cell apoptosis in vivo. *Invest. Ophthalmol. Vis. Sci.* 47, 626-633 (2006).

Honig & Hume. DiI and diO: versatile fluorescent dyes for neuronal labelling and pathway tracing. *Trends in neurosciences* 12, 333-335, 340-331. (1989).

Huerta et al. Screening and detection of apoptosis. *The Journal of surgical research* 139, 143-156 (2007).

LaFerla et al. Intracellular amyloid-beta in Alzheimer's disease. *Nat. Rev. Neurosci.* 8, 499-509 (2007).

Li et al. A syntaxin I, Galpha(o), and N-type calcium channel complex at a presynaptic nerve terminal: analysis by quantitative immunocolocalization. *J. Neurosci.* 24, 4070-4081 (2004).

Maass et al. Assessment of Rat and Mouse RGC Apoptosis Imaging in Vivo with Different Scanning Laser Ophthalmoscopes. *Current eye research* 32, 851-861 (2007).

Miguel-Hidalgo et al. Neuroprotection by memantine against neurodegeneration induced by beta-amyloid (1-40). *Brain Res.* 958, 210-221. (2002).

Ning et al. Amyloid Beta Deposits Lead to Retinal Degeneration in a Mouse Model of Alzheimer Disease. *Inves.t Ophthalmol. Vis. Sci.* 49, 5136-5143 (2008).

Oddo et al. Triple-transgenic model of Alzheimer's disease with plaques and tangles: intracellular Abeta and synaptic dysfunction. *Neuron* 39, 409-421 (2003).

Schmitz-Valckenberg et al. Real-time in-vivo imaging of retinal cell apoptosis after laser exposure. *Invest. Ophthalmol. Vis. Sci.* (2008).

Sensi et al. Altered oxidant-mediated intraneuronal zinc mobilization in a triple transgenic mouse model of Alzheimer's disease. *Exp. Gerontol.* 43, 488-492 (2008).

Shimazawa et al. Reduced retinal function in amyloid precursor protein-over-expressing transgenic mice via attenuating glutamate-N-methyl-d-aspartate receptor signaling. *J. Neurochem.* 107, 279-290 (2008).

von Ruckmann & Fitzke, Distribution of fundus autofluorescence with a scanning laser ophthalmoscope. *Br. J. Ophthalmol.* 79, 407-12. (1995).

Wade & Fitzke, A fast, robust pattern recognition system for low light level image registration and its application to retinal imaging. *Optics Express* 3, 190-197 (1998).

Abe, Y., Hashimoto, S., and Horie, T. (1999). Curcumin inhibition of inflammatory cytokine production by human peripheral blood monocytes and alveolar macrophages. Pharmacol Res 39, 41-47.

Almasieh, M., Zhou, Y., Kelly, M. E., Casanova, C., and Di Polo, A. (2010). Structural and functional neuroprotection in glaucoma: role of galantamine-mediated activation of muscarinic acetylcholine receptors. Cell Death Dis 1.

Anderson, D. R., and Hendrickson, A. (1974). Effect of intraocular pressure on rapid axoplasmic transport in monkey optic nerve. Investigative ophthalmology 13, 771-783.

Andrabi, S. A., Sayeed, I., Siemen, D., Wolf, G., and Horn, T. F. (2004). Direct inhibition of the mitochondrial permeability transition pore: a possible mechanism responsible for anti-apoptotic effects of melatonin. Faseb J 18, 869-871.

Aoun, P., Simpkins, J. W., and Agarwal, N. (2003). Role of PPAR-gamma ligands in neuroprotection against glutamate-induced cytotoxicity in retinal ganglion cells. Invest Ophthalmol Vis Sci 44, 2999-3004.

Attems, J., and Jellinger, K. A. (2006). Olfactory tau pathology in Alzheimer disease and mild cognitive impairment. Clinical neuropathology 25, 265-271.

Augustin, S., Rimbach, G., Augustin, K., Schliebs, R., Wolfram, S., and Cermak, R. (2009). Effect of a short- and long-term treatment with *Ginkgo biloba* extract on amyloid precursor protein levels in a transgenic mouse model relevant to Alzheimer's disease. Archives of biochemistry and biophysics 481, 177-182.

Aydemir, O., Naziroglu, M., Celebi, S., Yilmaz, T., and Kukner, A. S. (2004). Antioxidant effects of alpha-, gamma- and succinate-tocopherols in guinea pig retina during ischemia-reperfusion injury. Pathophysiology 11, 167-171.

Bakalash, S., Kessler, A., Mizrahi, T., Nussenblatt, R., and Schwartz, M. (2003). Antigenic specificity of immunoprotective therapeutic vaccination for glaucoma. Invest Ophthalmol Vis Sci 44, 3374-3381.

Barde, Y. A., Edgar, D., and Thoenen, H. (1982). Purification of a new neurotrophic factor from mammalian brain. The EMBO journal 1, 549-553.

Bastianetto, S., Ramassamy, C., Dore, S., Christen, Y., Poirier, J., and Quirion, R. (2000a). The *Ginkgo biloba* extract (EGb 761) protects hippocampal neurons against cell death induced by beta-amyloid. The European journal of neuroscience 12, 1882-1890.

Bastianetto, S., Zheng, W. H., and Quirion, R. (2000b). The *Ginkgo biloba* extract (EGb 761) protects and rescues hippocampal cells against nitric oxide-induced toxicity: involvement of its flavonoid constituents and protein kinase C. Journal of neurochemistry 74, 2268-2277.

Bayer, A. U., Keller, O. N., Ferrari, F., and Maag, K. P. (2002). Association of glaucoma with neurodegenerative diseases with apoptotic cell death: Alzheimer's disease and Parkinson's disease. American journal of ophthalmology 133, 135-137.

Beal, M. F. (2003). Bioenergetic approaches for neuroprotection in Parkinson's disease. Annals of neurology 53 Suppl 3, S39-47; discussion S47-38.

Behrens, M. M., Strasser, U., Heidinger, V., Lobner, D., Yu, S. P., McDonald, J. W., Won, M., and Choi, D. W. (1999). Selective activation of group II mGluRs with LY354740 does not prevent neuronal excitotoxicity. Neuropharmacology 38, 1621-1630.

Ben Simon, G. J., Bakalash, S., Aloni, E., and Rosner, M. (2006). A rat model for acute rise in intraocular pressure: immune modulation as a therapeutic strategy. American journal of ophthalmology 141, 1105-1111.

Bensimon, G., Lacomblez, L., and Meininger, V. (1994). A controlled trial of riluzole in amyotrophic lateral sclerosis. ALS/Riluzole Study Group. The New England journal of medicine 330, 585-591.

Berkelaar, M., Clarke, D. B., Wang, Y. C., Bray, G. M., and Aguayo, A. J. (1994). Axotomy results in delayed death and apoptosis of retinal ganglion cells in adult rats. J Neurosci 14, 4368-4374.

Berkemeier, L. R., Winslow, J. W., Kaplan, D. R., Nikolics, K., Goeddel, D. V., and Rosenthal, A. (1991). Neurotrophin-5: a novel neurotrophic factor that activates trk and trkB. Neuron 7, 857-866.

Borras, T., Brandt, C. R., Nickells, R., and Ritch, R. (2002). Gene therapy for glaucoma: treating a multifaceted, chronic disease. Invest Ophthalmol Vis Sci 43, 2513-2518.

Brooks, D. E., Garcia, G. A., Dreyer, E. B., Zurakowski, D., and Franco-Bourland, R. E. (1997). Vitreous body glutamate concentration in dogs with glaucoma. American journal of veterinary research 58, 864-867.

Calzada, J. I., Jones, B. E., Netland, P. A., and Johnson, D. A. (2002). Glutamate-induced excitotoxicity in retina: neuroprotection with receptor antagonist, dextromethorphan, but not with calcium channel blockers. Neurochemical research 27, 79-88.

Casson, R. J. (2006). Possible role of excitotoxicity in the pathogenesis of glaucoma. Clinical & experimental ophthalmology 34, 54-63.

Cazevieille, C., and Osborne, N. N. (1997). Retinal neurones containing kainate receptors are influenced by exogenous kainate and ischaemia while neurones lacking these receptors are not—melatonin counteracts the effects of ischaemia and kainate. Brain Res 755, 91-100.

Cazevieille, C., Safa, R., and Osborne, N. N. (1997). Melatonin protects primary cultures of rat cortical neurones from NMDA excitotoxicity and hypoxia/reoxygenation. Brain research 768, 120-124.

Chaudhary, P., Ahmed, F., and Sharma, S. C. (1998). MK801-a neuroprotectant in rat hypertensive eyes. Brain Res 792, 154-158.

Chen, G., and Goeddel, D. V. (2002). TNF-R1 signaling: a beautiful pathway. Science (New York, N.Y. 296, 1634-1635.

Cheng, L., Sapieha, P., Kittlerova, P., Hauswirth, W. W., and Di Polo, A. (2002). TrkB gene transfer protects retinal ganglion cells from axotomy-induced death in vivo. J Neurosci 22, 3977-3986.

Cheung, W., Guo, L., and Cordeiro, M. F. (2008). Neuroprotection in glaucoma: drug-based approaches. Optom Vis Sci 85, 406-416.

Chidlow, G., Schmidt, K. G., Wood, J. P., Melena, J., and Osborne, N. N. (2002). Alpha-lipoic acid protects the retina against ischemia-reperfusion. Neuropharmacology 43, 1015-1025.

Chidlow, G., Wood, J. P., and Casson, R. J. (2007). Pharmacological neuroprotection for glaucoma. Drugs 67, 725-759.

Choi, D. W. (1992). Excitotoxic cell death. Journal of neurobiology 23, 1261-1276.

Chung, H. S., Harris, A., Kristinsson, J. K., Ciulla, T. A., Kagemann, C., and Ritch, R. (1999). *Ginkgo biloba* extract increases ocular blood flow velocity. J Ocul Pharmacol Ther 15, 233-240.

Colafrancesco, V., Parisi, V., Sposato, V., Rossi, S., Russo, M. A., Coassin, M., Lambiase, A., and Aloe, L. (2010). Ocular Application of Nerve Growth Factor Protects Degenerating Retinal Ganglion Cells in a Rat Model of Glaucoma. J. Glaucoma.

Cordeiro, M. F., Guo, L., Luong, V., Harding, G., Wang, W., Jones, H. E., Moss, S. E., Sillito, A. M., and Fitzke, F. W. (2004). Real-time imaging of single nerve cell apoptosis in retinal neurodegeneration. Proceedings of the National Academy of Sciences of the United States of America 101, 13352-13356.

Cordeiro, M. F., Nickells, R., Drexler, W., Borras, T., and Ritch, R. (2009). High-resolution ocular imaging: combining advanced optics and microtechnology. Ophthalmic Surg Lasers Imaging 40, 480-488.

Cui, Q., and Harvey, A. R. (1995). At least two mechanisms are involved in the death of retinal ganglion cells following target ablation in neonatal rats. J Neurosci 15, 8143-8155.

Cunha, R. A., Ribeiro, J. A., and Malva, J. O. (2004). Presynaptic kainate receptors modulating glutamatergic transmission in the rat hippocampus are inhibited by arachidonic acid. Neurochemistry international 44, 371-379.

D'Astous, M., Morissette, M., and Di Paolo, T. (2004). Effect of estrogen receptor agonists treatment in MPTP mice: evidence of neuroprotection by an ER alpha agonist. Neuropharmacology 47, 1180-1188.

Diamond, B. J., Shiflett, S. C., Feiwel, N., Matheis, R. J., Noskin, O., Richards, J. A., and Schoenberger, N. E. (2000). *Ginkgo biloba* extract: mechanisms and clinical indications. Archives of physical medicine and rehabilitation 81, 668-678.

Digicaylioglu, M., and Lipton, S. A. (2001). Erythropoietin-mediated neuroprotection involves cross-talk between Jak2 and NF-kappaB signalling cascades. Nature 412, 641-647.

Doble, A. (1999). The role of excitotoxicity in neurodegenerative disease: implications for therapy. Pharmacology & therapeutics 81, 163-221.

Donello, J. E., Padillo, E. U., Webster, M. L., Wheeler, L. A., and Gil, D. W. (2001). alpha(2)-Adrenoceptor agonists inhibit vitreal glutamate and aspartate accumulation and preserve retinal function after transient ischemia. J Pharmacol Exp Ther 296, 216-223.

Dong, C. J., Guo, Y., Agey, P., Wheeler, L., and Hare, W. A. (2008). Alpha2 adrenergic modulation of NMDA receptor function as a major mechanism of RGC protection in experimental glaucoma and retinal excitotoxicity. Invest Ophthalmol Vis Sci 49, 4515-4522.

Dreyer, E. B., Zurakowski, D., Schumer, R. A., Podos, S. M., and Lipton, S. A. (1996). Elevated glutamate levels in the vitreous body of humans and monkeys with glaucoma. Archives of ophthalmology 114, 299-305.

Dubai, D. B., Zhu, H., Yu, J., Rau, S. W., Shughrue, P. J., Merchenthaler, I., Kindy, M. S., and Wise, P. M. (2001). Estrogen receptor alpha, not beta, is a critical link in estradiol-mediated protection against brain injury. Proceedings of the National Academy of Sciences of the United States of America 98, 1952-1957.

Dubocovich, M. L., Masana, M. I., Iacob, S., and Sauri, D. M. (1997). Melatonin receptor antagonists that differentiate between the human Mella and Mellb recombinant subtypes are used to assess the pharmacological profile of the rabbit retina ML1 presynaptic heteroreceptor. Naunyn-Schmiedeberg's archives of pharmacology 355, 365-375.

Duhaime, A. C., Gennarelli, L. M., and Boardman, C. (1996). Neuroprotection by dextromethorphan in acute experimental subdural hematoma in the rat. Journal of neurotrauma 13, 79-84.

Dykens, J. A., Carroll, A. K., Wiley, S., Covey, D. F., Cai, Z. Y., Zhao, L., and Wen, R. (2004). Photoreceptor preservation in the S334ter model of retinitis pigmentosa by a novel estradiol analog. Biochemical pharmacology 68, 1971-1984.

el-Asrar, A. M., Morse, P. H., Maimone, D., Torczynski, E., and Reder, A. T. (1992). MK-801 protects retinal neurons from hypoxia and the toxicity of glutamate and aspartate. Invest Ophthalmol Vis Sci 33, 3463-3468.

El-Remessy, A. B., Khalil, I. E., Matragoon, S., Abou-Mohamed, G., Tsai, N. J., Roon, P., Caldwell, R. B., Caldwell, R. W., Green, K., and Liou, G. I. (2003). Neuroprotective effect of (−)Delta9-tetrahydrocannabinol and cannabidiol in N-methyl-D-aspartate-induced retinal neurotoxicity: involvement of peroxynitrite. The American journal of pathology 163, 1997-2008.

Eschweiler, G. W., and Bahr, M. (1993). Flunarizine enhances rat retinal ganglion cell survival after axotomy. Journal of the neurological sciences 116, 34-40.

Ettaiche, M., Fillacier, K., Widmann, C., Heurteaux, C., and Lazdunski, M. (1999). Riluzole improves functional recovery after ischemia in the rat retina. Invest Ophthalmol Vis Sci 40, 729-736.

Evans (2002). Pharmacognosy, 17th edn (Philadelphia: W.B. Saunders).

Fingert, J. H., Heon, E., Liebmann, J. M., Yamamoto, T., Craig, J. E., Rait, J., Kawase, K., Hoh, S. T., Buys, Y. M., Dickinson, J., et al. (1999). Analysis of myocilin mutations in 1703 glaucoma patients from five different populations. Human molecular genetics 8, 899-905.

Finkel, T. (1998). Oxygen radicals and signaling. Current opinion in cell biology 10, 248-253.

Finkel, T., and Holbrook, N. J. (2000). Oxidants, oxidative stress and the biology of ageing. Nature 408, 239-247.

Fix, A. S., Horn, J. W., Wightman, K. A., Johnson, C. A., Long, G. G., Storts, R. W., Farber, N., Wozniak, D. F., and Olney, J. W. (1993). Neuronal vacuolization and necrosis induced by the noncompetitive N-methyl-D-aspartate (NMDA) antagonist MK(+)801 (dizocilpine maleate): a light and electron microscopic evaluation of the rat retrosplenial cortex. Experimental neurology 123, 204-215.

Flammer, J., Haefliger, I. O., Orgul, S., and Resink, T. (1999). Vascular dysregulation: a principal risk factor for glaucomatous damage? Journal of glaucoma 8, 212-219.

Fontaine, V., Mohand-Said, S., Hanoteau, N., Fuchs, C., Pfizenmaier, K., and Eisel, U. (2002). Neurodegenerative and neuroprotective effects of tumor Necrosis factor (TNF) in retinal ischemia: opposite roles of TNF receptor 1 and TNF receptor 2. J Neurosci 22, RC216.

Foster, A. C., Gill, R., and Woodruff, G. N. (1988). Neuroprotective effects of MK-801 in vivo: selectivity and evidence for delayed degeneration mediated by NMDA receptor activation. J Neurosci 8, 4745-4754.

Garcia-Segura, L. M., Cardona-Gomez, P., Naftolin, F., and Chowen, J. A. (1998). Estradiol upregulates Bcl-2 expression in adult brain neurons. Neuroreport 9, 593-597.

Gibbs, J. W., 3rd, Sombati, S., DeLorenzo, R. J., and Coulter, D. A. (2000). Cellular actions of topiramate: blockade of kainate-evoked inward currents in cultured hippocampal neurons. Epilepsia 41 Suppl 1, S10-16.

Goldberg, M. P., Pham, P. C., and Choi, D. W. (1987). Dextrorphan and dextromethorphan attenuate hypoxic injury in neuronal culture. Neuroscience letters 80, 11-15.

Goldblum, D., Kipfer-Kauer, A., Sarra, G. M., Wolf, S., and Frueh, B. E. (2007). Distribution of amyloid precursor protein and amyloid-beta immunoreactivity in DBA/2J glaucomatous mouse retinas. Invest Ophthalmol Vis Sci 48, 5085-5090.

Gross, R. L., Hensley, S. H., Gao, F., and Wu, S. M. (1999). Retinal ganglion cell dysfunction induced by hypoxia and glutamate: potential neuroprotective effects of beta-blockers. Surv Ophthalmol 43 Suppl 1, S162-170.

Guo, L., Moss, S. E., Alexander, R. A., Ali, R. R., Fitzke, F. W., and Cordeiro, M. F. (2005). Retinal ganglion cell apoptosis in glaucoma is related to intraocular pressure and IOP-induced effects on extracellular matrix. Invest Ophthalmol Vis Sci 46, 175-182.

Guo, L., Salt, T. E., Luong, V., Wood, N., Cheung, W., Maass, A., Ferrari, G., Russo-Marie, F., Sillito, A. M., Cheetham, M. E., et al. (2007). Targeting amyloid-beta in glaucoma treatment. Proceedings of the National Academy of Sciences of the United States of America 104, 13444-13449.

Guo, L., Salt, T. E., Maass, A., Luong, V., Moss, S. E., Fitzke, F. W., and Cordeiro, M. F. (2006). Assessment of neuroprotective effects of glutamate modulation on glaucoma-related retinal ganglion cell apoptosis in vivo. Invest Ophthalmol Vis Sci 47, 626-633.

Gupta, N., Ang, L. C., Noel de Tilly, L., Bidaisee, L., and Yucel, Y. H. (2006). Human glaucoma and neural degeneration in intracranial optic nerve, lateral geniculate nucleus, and visual cortex. Br J Ophthalmol 90, 674-678.

Hagen, T. M., Ingersoll, R. T., Lykkesfeldt, J., Liu, J., Wehr, C. M., Vinarsky, V., Bartholomew, J. C., and Ames, A. B. (1999). (R)-alpha-lipoic acid-supplemented old rats have improved mitochondrial function, decreased oxidative damage, and increased metabolic rate. Faseb J 13, 411-418.

Hains, B. C., and Waxman, S. G. (2005). Neuroprotection by sodium channel blockade with phenyloin in an experimental model of glaucoma. Invest Ophthalmol Vis Sci 46, 4164-4169.

Harvey, A. R., Hu, Y., Leaver, S. G., Mellough, C. B., Park, K., Verhaagen, J., Plant, G. W., and Cui, Q. (2006). Gene therapy and transplantation in CNS repair: the visual system. Prog Retin Eye Res 25, 449-489.

Hayreh, S. S., March, W., and Anderson, D. R. (1979). Pathogenesis of block of rapid orthograde axonal transport by elevated intraocular pressure. Exp Eye Res 28, 515-523.

Hernandez, M., Urcola, J. H., and Vecino, E. (2008). Retinal ganglion cell neuroprotection in a rat model of glaucoma following brimonidine, latanoprost or combined treatments. Exp Eye Res 86, 798-806.

Hirooka, K., Tokuda, M., Miyamoto, O., Itano, T., Baba, T., and Shiraga, F. (2004). The *Ginkgo biloba* extract (EGb 761) provides a neuroprotective effect on retinal ganglion cells in a rat model of chronic glaucoma. Curr Eye Res 28, 153-157.

Hirsch, T., Marchetti, P., Susin, S. A., Dallaporta, B., Zamzami, N., Marzo, I., Geuskens, M., and Kroemer, G. (1997). The apoptosis-necrosis paradox. Apoptogenic proteases activated after mitochondrial permeability transition determine the mode of cell death. Oncogene 15, 1573-1581.

Hoffman, G. E., Merchenthaler, I., and Zup, S. L. (2006). Neuroprotection by ovarian hormones in animal models of neurological disease. Endocrine 29, 217-231.

Hohn, A., Leibrock, J., Bailey, K., and Barde, Y. A. (1990). Identification and characterization of a novel member of the nerve growth factor/brain-derived neurotrophic factor family. Nature 344, 339-341.

Honda, K., Sawada, H., Kihara, T., Urushitani, M., Nakamizo, T., Akaike, A., and Shimohama, S. (2000). Phosphatidylinositol 3-kinase mediates neuroprotection by estrogen in cultured cortical neurons. J Neurosci Res 60, 321-327.

Hong, S., Kim, C. Y., Lee, J. E., and Seong, G. J. (2009). Agmatine protects cultured retinal ganglion cells from tumor necrosis factor-alpha-induced apoptosis. Life Sci 84, 28-32.

Hong, S., Park, K., Kim, C. Y., and Seong, G. J. (2008). Agmatine inhibits hypoxia-induced TNF-alpha release from cultured retinal ganglion cells. Biocell 32, 201-205.

Howell, G. R., Libby, R. T., Jakobs, T. C., Smith, R. S., Phalan, F. C., Barter, J. W., Barbay, J. M., Marchant, J. K., Mahesh, N., Porciatti, V., et al. (2007). Axons of retinal ganglion cells are insulted in the optic nerve early in DBA/2J glaucoma. J Cell Biol 179, 1523-1537.

Huang, W., Fileta, J. B., Dobberfuhl, A., Filippopolous, T., Guo, Y., Kwon, G., and Grosskreutz, C. L. (2005). Calcineurin cleavage is triggered by elevated intraocular pressure, and calcineurin inhibition blocks retinal ganglion cell death in experimental glaucoma. Proceedings of the National Academy of Sciences of the United States of America 102, 12242-12247.

Hyndman, A. G. (1984). The effects of glutamate and kainate on cell proliferation in retinal cultures. Invest Ophthalmol Vis Sci 25, 558-563.

Inokuchi, Y., Shimazawa, M., Nakajima, Y., Suemori, S., Mishima, S., and Hara, H. (2006). Brazilian green propolis protects against retinal damage in vitro and in vivo. Evid Based Complement Alternat Med 3, 71-77.

Ishii, Y., Kwong, J. M., and Caprioli, J. (2003). Retinal ganglion cell protection with geranylgeranylacetone, a heat shock protein inducer, in a rat glaucoma model. Invest Ophthalmol Vis Sci 44, 1982-1992.

Jelsma, T. N., Friedman, H. H., Berkelaar, M., Bray, G. M., and Aguayo, A. J. (1993). Different forms of the neurotrophin receptor trkB mRNA predominate in rat retina and optic nerve. J Neurobiol 24, 1207-1214.

Ji, J. Z., Elyaman, W., Yip, H. K., Lee, V. W., Yick, L. W., Hugon, J., and So, K. F. (2004). CNTF promotes survival of retinal ganglion cells after induction of ocular hypertension in rats: the possible involvement of STAT3 pathway. Eur J Neurosci 19, 265-272.

Jiang, C., Moore, M. J., Zhang, X., Klassen, H., Langer, R., and Young, M. (2007). Intravitreal injections of GDNF-loaded biodegradable microspheres are neuroprotective in a rat model of glaucoma. Mol Vis 13, 1783-1792.

Jing, S., Wen, D., Yu, Y., Hoist, P. L., Luo, Y., Fang, M., Tamir, R., Antonio, L., Hu, Z., Cupples, R., et al. (1996). GDNF-induced activation of the ret protein tyrosine kinase is mediated by GDNFR-alpha, a novel receptor for GDNF. Cell 85, 1113-1124.

Johnson, J. E., Barde, Y. A., Schwab, M., and Thoenen, H. (1986). Brain-derived neurotrophic factor supports the survival of cultured rat retinal ganglion cells. J Neurosci 6, 3031-3038.

Johnson, J. W., and Kotermanski, S. E. (2006). Mechanism of action of memantine. Curr Opin Pharmacol 6, 61-67.

Johnson, L. V., Leitner, W. P., Rivest, A. J., Staples, M. K., Radeke, M. J., and Anderson, D. H. (2002). The Alzheimer's A beta-peptide is deposited at sites of complement activation in pathologic deposits associated with aging and age-related macular degeneration. Proceedings of the National Academy of Sciences of the United States of America 99, 11830-11835.

Johnson, T. V., and Tomarev, S. I. (2010). Rodent models of glaucoma. Brain research bulletin 81, 349-358.

Jou, M. J., Peng, T. I., Reiter, R. J., Jou, S. B., Wu, H. Y., and Wen, S. T. (2004). Visualization of the antioxidative effects of melatonin at the mitochondrial level during oxidative stress-induced apoptosis of rat brain astrocytes. J Pineal Res 37, 55-70.

Ju, W. K., Kim, K. Y., Angert, M., Duong-Polk, K. X., Lindsey, J. D., Ellisman, M. H., and Weinreb, R. N. (2009). Memantine blocks mitochondrial OPA1 and cytochrome c release and subsequent apoptotic cell death in glaucomatous retina. Invest Ophthalmol Vis Sci 50, 707-716.

Junk, A. K., Mammis, A., Savitz, S. I., Singh, M., Roth, S., Malhotra, S., Rosenbaum, P. S., Cerami, A., Brines, M., and Rosenbaum, D. M. (2002). Erythropoietin administration protects retinal neurons from acute ischemia-reperfusion injury. Proceedings of the National Academy of Sciences of the United States of America 99, 10659-10664.

Juravleva, E., Barbakadze, T., Mikeladze, D., and Kekelidze, T. (2005). Creatine enhances survival of glutamate-treated neuronal/glial cells, modulates Ras/NF-kappaB signaling, and increases the generation of reactive oxygen species. J Neurosci Res 79, 224-230.

Kanowski, S., Herrmann, W. M., Stephan, K., Wierich, W., and Horr, R. (1996). Proof of efficacy of the *ginkgo biloba* special extract EGb 761 in outpatients suffering from mild to moderate primary degenerative dementia of the Alzheimer type or multi-infarct dementia. Pharmacopsychiatry 29, 47-56.

Kanowski, S., and Hoerr, R. (2003). *Ginkgo biloba* extract EGb 761 in dementia: intent-to-treat analyses of a 24-week, multi-center, double-blind, placebo-controlled, randomized trial. Pharmacopsychiatry 36, 297-303.

Kapin, M. A., Doshi, R., Scatton, B., DeSantis, L. M., and Chandler, M. L. (1999). Neuroprotective effects of eliprodil in retinal excitotoxicity and ischemia. Invest Ophthalmol Vis Sci 40, 1177-1182.

Kaplan, D. R., Hempstead, B. L., Martin-Zanca, D., Chao, M. V., and Parada, L. F. (1991). The trk proto-oncogene product: a signal transducing receptor for nerve growth factor. Science 252, 554-558.

Katsuki, H., Yamamoto, R., Nakata, D., Kume, T., and Akaike, A. (2004). Neuronal nitric oxide synthase is crucial for ganglion cell death in rat retinal explant cultures. J Pharmacol Sci 94, 77-80.

Kaur, C., Foulds, W. S., and Ling, E. A. (2008). Hypoxia-ischemia and retinal ganglion cell damage. Clin Ophthalmol 2, 879-889.

Kawasaki, A., Han, M. H., Wei, J. Y., Hirata, K., Otori, Y., and Barnstable, C. J. (2002). Protective effect of arachidonic acid on glutamate neurotoxicity in rat retinal ganglion cells. Invest Ophthalmol Vis Sci 43, 1835-1842.

Kawasaki, A., Otori, Y., and Barnstable, C. J. (2000). Muller cell protection of rat retinal ganglion cells from glutamate and nitric oxide neurotoxicity. Invest Ophthalmol Vis Sci 41, 3444-3450.

Kerrigan, L. A., Zack, D. J., Quigley, H. A., Smith, S. D., and Pease, M. E. (1997). TUNEL-positive ganglion cells in human primary open-angle glaucoma. Archives of ophthalmology 115, 1031-1035.

Khoury, R., Cross, J. M., Girkin, C. A., Owsley, C., and McGwin, G. (2009). The Association Between Self-reported Glaucoma and *Ginkgo Biloba* Use. Journal of Glaucoma 18, 543-545.

Kikuchi, M., Tenneti, L., and Lipton, S. A. (2000). Role of p38 mitogen-activated protein kinase in axotomy-induced apoptosis of rat retinal ganglion cells. J Neurosci 20, 5037-5044.

Kilic, E., Kilic, U., Yulug, B., Hermann, D. M., and Reiter, R. J. (2004). Melatonin reduces disseminate neuronal death after mild focal ischemia in mice via inhibition of caspase-3 and is suitable as an add-on treatment to tissue-plasminogen activator. J Pineal Res 36, 171-176.

Kilic, U., Kilic, E., Reiter, R, J., Bassetti, C. L., and Hermann, D. M. (2005a). Signal transduction pathways involved in melatonin-induced neuroprotection after focal cerebral ischemia in mice. J Pineal Res 38, 67-71.

Kilic, U., Kilic, E., Soliz, J., Bassetti, C. I., Gassmann, M., and Hermann, D. M. (2005b). Erythropoietin protects from axotomy-induced degeneration of retinal ganglion cells by activating ERK-1/-2. Faseb J 19, 249-251.

Kim, T. W., Kim, D. M., Park, K. H., and Kim, H. (2002). Neuroprotective effect of memantine in a rabbit model of optic nerve ischemia. Korean J Ophthalmol 16, 1-7.

Kipnis, J., Yoles, E., Porat, Z., Cohen, A., Mor, F., Sela, M., Cohen, I. R., and Schwartz, M. (2000). T cell immunity to copolymer I confers neuroprotection on the damaged optic nerve: possible therapy for optic neuropathies. Proceedings of the National Academy of Sciences of the United States of America 97, 7446-7451.

Klivenyi, P., Ferrante, R. J., Matthews, R. T., Bogdanov, M. B., Klein, A. M., Andreassen, O. A., Mueller, G., Wermer, M., Kaddurah-Daouk, R., and Beal, M. F. (1999). Neuroprotective effects of creatine in a transgenic animal model of amyotrophic lateral sclerosis. Nature medicine 5, 347-350.

Knels, L., Worm, M., Wendel, M., Roehlecke, C., Kniep, E., and Funk, R. H. (2008). Effects of advanced glycation end products-inductor glyoxal and hydrogen peroxide as oxidative stress factors on rat retinal organ cultures and neuroprotection by UK-14,304. J Neurochem 106, 1876-1887.

Ko, M. L., Peng, P. H., Ma, M. C., Ritch, R., and Chen, C. F. (2005). Dynamic changes in reactive oxygen species and antioxidant levels in retinas in experimental glaucoma. Free Radic Biol Med 39, 365-373.

Kobayashi, K., Kobayashi, H., Ueda, M., and Honda, Y. (1998). Estrogen receptor expression in bovine and rat retinas. Invest Ophthalmol Vis Sci 39, 2105-2110.

Kristian, T., and Siesjo, B. K. (1998). Calcium in ischemic cell death, Stroke 29, 705-718.

Krupin, T., Liebmann, J. M., Greenfield, D. S., Rosenberg, L. F., Ritch, R., and Yang, J. W. (2005). The Low-pressure Glaucoma Treatment Study (LoGTS) study design and baseline characteristics of enrolled patients. Ophthalmology 112, 376-385.

Kumar, D. M., Perez, E., Cai, Z. Y., Aoun, P., Brun-Zinkernagel, A. M., Covey, D. F., Simpkins, J. W., and Agarwal, N. (2005). Role of nonfeminizing estrogen analogues in neuroprotection of rat retinal ganglion cells against glutamate-induced cytotoxicity. Free Radic Biol Med 38, 1152-1163.

Kwon, Y. H., Fingert, J. H., Kuehn, M. H., and Alward, W. L. (2009). Primary open-angle glaucoma. N Engl J Med 360, 1113-1124.

Lacomblez, L., Bensimon, G., Leigh, P. N., Guillet, P., Powe, L., Durrleman, S., Delumeau, J. C., and Meininger, V. (1996). A confirmatory dose-ranging study of riluzole in ALS. ALS/Riluzole Study Group-II. Neurology 47, S242-250.

Laengle, U. W., Markstein, R., Pralet, D., Seewald, W., and Roman, D. (2006a). Effect of GLC756, a novel mixed dopamine D1 receptor antagonist and dopamine D2 receptor agonist, on TNF-alpha release in vitro from activated rat mast cells. Exp Eye Res 83, 1335-1339.

Laengle, U. W., Trendelenburg, A. U., Markstein, R., Nogues, V., Provencher-Bollinger, A., and Roman, D. (2006b). GLC756 decreases TNF-alpha via an alpha2 and beta2 adrenoceptor related mechanism. Exp Eye Res 83, 1246-1251.

Lagreze, W. A., Knorle, R., Bach, M., and Feuerstein, T. J. (1998). Memantine is neuroprotective in a rat model of pressure-induced retinal ischemia. Invest Ophthalmol Vis Sci 39, 1063-1066.

Lai, R. K., Chun, T., Hasson, D., Lee, S., Mehrbod, F., and Wheeler, L. (2002). Alpha-2 adrenoceptor agonist protects retinal function after acute retinal ischemic injury in the rat. Vis Neurosci 19, 175-185.

Lambert, W. S., Clark, A. F., and Wordinger, R. J. (2004). Effect of exogenous neurotrophins on Trk receptor phosphorylation, cell proliferation, and neurotrophin secretion by cells isolated from the human lamina cribrosa. Mol Vis 10, 289-296.

Lambiase, A., Aloe, L., Centofanti, M., Parisi, V., Mantelli, F., Colafrancesco, V., Manni, G. L., Bucci, M. G., Bonini, S., and Levi-Montalcini, R. (2009). Experimental and clinical evidence of neuroprotection by nerve growth factor eye drops: Implications for glaucoma. Proc Natl Acad Sci USA.

Lebrun-Julien, F., Duplan, L., Pernet, V., Osswald, I., Sapieha, P., Bourgeois, P., Dickson, K., Bowie, D., Barker, P. A., and Di Polo, A, (2009). Excitotoxic death of retinal neurons in vivo occurs via a non-cell-autonomous mechanism. J Neurosci 29, 5536-5545.

Lee, S. H., Chun, W., Kong, P. J., Han, J. A., Cho, B. P., Kwon, O. Y., Lee, H. J., and Kim, S. S. (2006). Sustained activation of Akt by melatonin contributes to the protection against kainic acid-induced neuronal death in hippocampus. J Pineal Res 40, 79-85.

Leinders-Zufall, T., Rand, M. N., Waxman, S. G., and Kocsis, J. D. (1994). Differential role of two Ca(2+)-permeable non-NMDA glutamate channels in rat retinal ganglion cells: kainate-induced cytoplasmic and nuclear Ca2+ signals. J Neurophysiol 72, 2503-2516.

Levin, L. A., and Peeples, P. (2008), History of neuroprotection and rationale as a therapy for glaucoma. Am. J Manag Care 14, S11-14.

Li, S. Y., Fu, Z. J., Ma, H., Jang, W. C., So, K. F., Wong, D., and Lo, A. C. (2009). Effect of lutein on retinal neurons and oxidative stress in a model of acute retinal ischemia/reperfusion. Invest Ophthalmol Vis Sci 50, 836-843.

Li, X., Qian, S. H., and Sun, X. H. (2008). [Protection of autoimmunity induced by copolymer-I on optic nerve: experiment with rat glaucoma models]. Zhonghua Yi Xue Za Zhi 88, 2152-2154.

Libby, R. T., Gould, D. B., Anderson, M. G., and John, S. W. (2005). Complex genetics of glaucoma susceptibility. Annu Rev Genomics Hum Genet. 6, 15-44.

Lim, G. P., Chu, T., Yang, F., Beech, W., Frautschy, S. A., and Cole, G. M. (2001). The curry spice curcumin reduces oxidative damage and amyloid pathology in an Alzheimer transgenic mouse. J Neurosci 21, 8370-8377.

Lipton, S. A. (1993). Prospects for clinically tolerated NMDA antagonists: open-channel blockers and alternative redox states of nitric oxide. Trends Neurosci 16, 527-532.

Lipton, S. A. (2006). Paradigm shift in neuroprotection by NMDA receptor blockade: memantine and beyond. Nat Rev Drug Discov 5, 160-170.

Liu, J., Head, E., Gharib, A. M., Yuan, W., Ingersoll, R. T., Hagen, T. M., Cotman, C. W., and Ames, B. N. (2002). Memory loss in old rats is associated with brain mitochondrial decay and RNA/DNA oxidation: partial reversal by feeding acetyl-L-carnitine and/or R-alpha-lipoic acid. Proceedings of the National Academy of Sciences of the United States of America 99, 2356-2361.

Liu, X., Rasmussen, C. A., Gabelt, B. T., Brandt, C. R., and Kaufman, P. L. (2009). Gene therapy targeting glaucoma: where are we? Surv Ophthalmol 54, 472-486.

Lorenzo, A., and Yankner, B. A. (1994). Beta-amyloid neurotoxicity requires fibril formation and is inhibited by congo red. Proceedings of the National Academy of Sciences of the United States of America 91, 12243-12247.

Luo, X., Heidinger, V., Picaud, S., Lambrou, G., Dreyfus, H., Sahel, J., and Hicks, D. (2001). Selective excitotoxic degeneration of adult pig retinal ganglion cells in vitro. Invest Ophthalmol Vis Sci 42, 1096-1106.

Mabuchi, F., Tang, S., Kashiwagi, K., Yamagata, Z., Iijima, H., and Tsukahara, S. (2007). The OPA 1 gene polymorphism is associated with normal tension and high tension glaucoma. Am J Ophthalmol 143, 125-130.

Mandal, M. N., Patlolla, J. M., Zheng, L., Agbaga, M. P., Tran, J. T., Wicker, L., Kasus-Jacobi, A., Elliott, M. H., Rao, C. V., and Anderson, R. E. (2009). Curcumin protects retinal cells from light- and oxidant stress-induced cell death. Free Radic Biol Med 46, 672-679.

Mansour-Robaey, S., Clarke, D. B., Wang, Y. C., Bray, G. M., and Aguayo, A. J. (1994). Effects of ocular injury and administration of brain-derived neurotrophic factor on survival and regrowth of axotomized retinal ganglion cells. Proceedings of the National Academy of Sciences of the United States of America 91, 1632-1636.

Marchetti, P., Castedo, M., Susin, S. A., Zamzami, N., Hirsch, T., Macho, A., Haeffner, A., Hirsch, F., Geuskens, M., and Kroemer, G. (1996). Mitochondrial permeability transition is a central coordinating event of apoptosis. J Exp Med 184, 1155-1160.

Matteucci, A., Frank, C., Domenici, M. R., Balduzzi, M., Paradisi, S., Camovale-Scalzo, G., Scorcia, G., and Malchiodi-Albedi, F. (2005). Curcumin treatment protects rat retinal neurons against excitotoxicity: effect on N-methyl-D:-aspartate-induced intracellular Ca(2+) increase. Exp Brain Res 167, 641-648.

Matthews, R. T., Ferrante, R. J., Klivenyi, P., Yang, L., Klein, A. M., Mueller, G., Kaddurah-Daouk, R., and Beal, M. F. (1999). Creatine and cyclocreatine attenuate MPTP neurotoxicity. Exp Neurol 157, 142-149.

Matthews, R. T., Yang, L., Jenkins, B. G., Ferrante, R. J., Rosen, B. R., Kaddurah-Daouk, R., and Beal, M. F. (1998), Neuroprotective effects of creatine and cyclocreatine in animal models of Huntington's disease. J Neurosci 18, 156-163.

McIlnay, T. R., Gionfriddo, J. R., Dubielzig, R. R., Powell, C. C., and Madl, J. E. (2004). Evaluation of glutamate loss from damaged retinal cells of dogs with primary glaucoma. Am J Vet Res 65, 776-786.

McKinnon, S. J., Lehman, D. M., Kerrigan-Baumrind, L. A., Merges, C. A., Pease, M. E., Kerrigan, D. F., Ransom, N. L., Tahzib, N. G., Reitsamer, H. A., Levkovitch-Verbin, H., et al. (2002a). Caspase activation and amyloid precursor protein cleavage in rat ocular hypertension. Invest Ophthalmol Vis Sci 43, 1077-1087.

McKinnon, S. J., Lehman, D. M., Tahzib, N. G., Ransom, N. L., Reitsamer, H. A., Liston, P., LaCasse, E., Li, Q., Korneluk, R. G., and Hauswirth, W. W. (2002b). Baculoviral IAP repeat-containing-4 protects optic nerve axons in a rat glaucoma model. Mol Ther 5, 780-787.

Mittag, T. W., Danias, J., Pohorenec, G., Yuan, H. M., Burakgazi, E., Chalmers-Redman, R., Podos, S. M., and Tatton, W. G. (2000). Retinal damage after 3 to 4 months of elevated intraocular pressure in a rat glaucoma model. Invest Ophthalmol Vis Sci 41, 3451-3459.

Moalem, G., Leibowitz-Amit, R., Yoles, E., Mor, F., Cohen, I. R., and Schwartz, M. (1999). Autoimmune T cells protect neurons from secondary degeneration after central nervous system axotomy. Nature medicine 5, 49-55.

Moalem, G., Yoles, E., Leibowitz-Amit, R., Muller-Gilor, S., Mor, F., Cohen, I. R., and Schwartz, M. (2000). Autoimmune T cells retard the loss of function in injured rat optic nerves. J Neuroimmunol 106, 189-197.

Moreno, M. C., Sande, P., Marcos, H. A., de Zavalia, N., Keller Sarmiento, M. I., and Rosenstein, R. E. (2005). Effect of glaucoma on the retinal glutamate/glutamine cycle activity. Faseb J 19, 1161-1162.

Mosinger, J. L., Price, M. T., Bai, H. Y., Xiao, H., Wozniak, D. F., and Olney, J. W. (1991). Blockade of both NMDA and non-NMDA receptors is required for optimal protection against ischemic neuronal degeneration in the in vivo adult mammalian retina. Exp Neurol 113, 10-17.

Murphy, M. P. (1999). Nitric oxide and cell death. Biochim Biophys Acta 1411, 401-414.

Nakajima, Y., Inokuchi, Y., Nishi, M., Shimazawa, M., Otsubo, K., and Hara, H. (2008). Coenzyme Q10 protects retinal cells against oxidative stress in vitro and in vivo. Brain Res 1226, 226-233.

Nakajima, Y., Shimazawa, M., Mishima, S., and Hara, H. (2009a). Neuroprotective effects of Brazilian green propolis and its main constituents against oxygen-glucose deprivation stress, with a gene-expression analysis. Phytother Res 23, 1431-1438.

Nakajima, Y., Shimazawa, M., Otsubo, K., Ishibashi, T., and Hara, H. (2009b). Zeaxanthin, a retinal carotenoid, protects retinal cells against oxidative stress. Curr Eye Res 34, 311-318.

Nakazawa, T., Takahashi, H., Nishijima, K., Shimura, M., Fuse, N., Tamai, M., Hafezi-Moghadam, A., and Nishida, K. (2007). Pitavastatin prevents NMDA-induced retinal ganglion cell death by suppressing leukocyte recruitment. J Neurochem 100, 1018-1031.

Nakazawa, T., Takahashi, H., and Shimura, M. (2006). Estrogen has a neuroprotective effect on axotomized RGCs through ERK signal transduction pathway. Brain Res 1093, 141-149.

Nash, M. S., Wood, J. P., Melena, J., and Osborne, N. N. (2000). Flupirtine ameliorates ischaemic-like death of rat retinal ganglion cells by preventing calcium influx. Brain Res 856, 236-239.

Naskar, R., Quinto, K., Romann, I., Schuettauf, F., and Zurakowski, D. (2002). Phenytoin blocks retinal ganglion cell death after partial optic nerve crush. Exp Eye Res 74, 747-752.

Naskar, R., Vorwerk, C. K., and Dreyer, E. B. (2000). Concurrent downregulation of a glutamate transporter and receptor in glaucoma. Invest Ophthalmol Vis Sci 41, 1940-1944.

Neacsu, A., Oprean, C., Curea, M., Tuchila, G., and Trifu, M. (2003). [Neuroprotection with carotenoids in glaucoma]. Oftalmologia 59, 70-75.

Neckers, L. (2007). Heat shock protein 90: the cancer chaperone. J Biosci 32, 517-530.

Negishi, H., Xu, J. W., Ikeda, K., Njelekela, M., Nara, Y., and Yamori, Y. (2004). Black and green tea polyphenols attenuate blood pressure increases in stroke-prone spontaneously hypertensive rats. J Nutr 134, 38-42.

Neufeld, A. H. (2004). Pharmacologic neuroprotection with an inhibitor of nitric oxide synthase for the treatment of glaucoma. Brain Res Bull 62, 455-459.

Neufeld, A. H., and Liu, B. (2003). Glaucomatous optic neuropathy: when glia misbehave. Neuroscientist 9, 485-495.

Neufeld, A. H., Sawada, A., and Becker, B. (1999). Inhibition of nitric-oxide synthase 2 by aminoguanidine provides neuroprotection of retinal ganglion cells in a rat model of chronic glaucoma. Proceedings of the National Academy of Sciences of the United States of America 96, 9944-9948.

Nickells, R. W. (1999). Apoptosis of retinal ganglion cells in glaucoma: an update of the molecular pathways involved in cell death. Surv Ophthalmol 43 Suppl 1, S151-161.

Nucci, C., Gasperi, V., Tartaglione, R., Cerulli, A., Terrinoni, A., Bari, M., De Simone, C., Agro, A. F., Morrone, L. A., Corasaniti, M. T., et al. (2007a). Involvement of the endocannabinoid system in retinal damage after high intraocular pressure-induced ischemia in rats. Invest Ophthalmol Vis Sci 48, 2997-3004.

Nucci, C., Tartaglione, R., Cerulli, A., Mancino, R., Spano, A., Cavaliere, F., Rombola, L., Bagetta, G., Corasaniti, M. T., and Morrone, L. A. (2007b). Retinal damage caused by high intraocular pressure-induced transient ischemia is prevented by coenzyme Q10 in rat. Int Rev Neurobiol 82, 397-406.

Ogueta, S. B., Schwartz, S. D., Yamashita, C. K., and Farber, D. B. (1999). Estrogen receptor in the human eye: influence of gender and age on gene expression. Invest Ophthalmol Vis Sci 40, 1906-1911.

Olney, J. W. (1969), Brain lesions, obesity, and other disturbances in mice treated with monosodium glutamate. Science 164, 719-721.

Opere, C. A., Zheng, W. D., Zhao, M., Lee, J. S., Kulkarni, K. H., and Ohia, S. E. (2006). Inhibition of potassium- and ischemia-evoked [3H] D-aspartate release from isolated bovine retina by cannabinoids. Curr Eye Res 31, 645-653.

Osborne, N. N. (2008). Pathogenesis of ganglion "cell death" in glaucoma and neuroprotection: focus on ganglion cell axonal mitochondria. Progress in brain research 173, 339-352.

Osborne, N. N., Ugarte, M., Chao, M., Chidlow, G., Bae, J. H., Wood, J. P., and Nash, M. S. (1999). Neuroprotection in relation to retinal ischemia and relevance to glaucoma. Surv Ophthalmol 43 Suppl 1, S102-128.

Osborne, N. N., Wood, J. P., Cupido, A., Melena, J., and Chidlow, G. (2002). Topical flunarizine reduces IOP and protects the retina against ischemia-excitotoxicity. Invest Ophthalmol Vis Sci 43, 1456-1464.

Otori, Y., Wei, J. Y., and Barnstable, C. J. (1998). Neurotoxic effects of low doses of glutamate on purified rat retinal ganglion cells. Invest Ophthalmol Vis Sci 39, 972-981.

Pang, I. H., Wexler, E. M., Nawy, S., DeSantis, L., and Kapin, M. A. (1999). Protection by eliprodil against excitotoxicity in cultured rat retinal ganglion cells. Invest Ophthalmol Vis Sci 40, 1170-1176.

Papucci, L., Schiavone, N., Witort, E., Donnini, M., Lapucci, A., Tempestini, A., Formigli, L., Zecchi-Orlandini, S., Orlandini, G., Carella, G., et al. (2003). Coenzyme q10 prevents apoptosis by inhibiting mitochondrial depolarization independently of its free radical scavenging property. J Biol Chem 278, 28220-28228.

Pastorino, J. G., Simbula, G., Yamamoto, K., Glascott, P. A., Jr., Rothman, R. J., and Farber, J. L. (1996). The cytotoxicity of tumor necrosis factor depends on induction of the mitochondrial permeability transition. J Biol Chem 271, 29792-29798.

Pease, M. E., Zack, D. J., Berlinicke, C., Bloom, K., Cone, F., Wang, Y., Klein, R. L., Hauswirth, W. W., and Quigley, H. A. (2009). Effect of CNTF on retinal ganglion cell survival in experimental glaucoma. Invest Ophthalmol Vis Sci 50, 2194-2200.

Pellegrini, J. W., and Lipton, S. A. (1993). Delayed administration of memantine prevents N-methyl-D-aspartate receptor-mediated neurotoxicity. Ann Neurol 33, 403-407.

Pepys, M. B. (2006). Amyloidosis. Annual review of medicine 57, 223-241.

Qu, J., Wang, D., and Grosskreutz, C. L. (2010). Mechanisms of retinal ganglion cell injury and defense in glaucoma. Exp Eye Res.

Quaranta, L., Bettelli, S., Uva, M. G., Semeraro, F., Turano, R., and Gandolfo, E. (2003). Effect of Ginkgo biloba extract on preexisting visual field damage in normal tension glaucoma. Ophthalmology 110, 359-362; discussion 362-354.

Quigley, H. A. (2005). Glaucoma: macrocosm to microcosm the Friedenwald lecture. Invest Ophthalmol Vis Sci 46, 2662-2670.

Quigley, H. A., and Broman, A. T. (2006). The number of people with glaucoma worldwide in 2010 and 2020. Br J Ophthalmol 90, 262-267.

Quigley, H. A., Nickells, R. W., Kerrigan, L. A., Pease, M. E., Thibault, D. J., and Zack, D. J. (1995). Retinal ganglion cell death in experimental glaucoma and after axotomy occurs by apoptosis. Invest Ophthalmol Vis Sci 36, 774-786.

Ray, K., Mukhopadhyay, A., and Acharya, M. (2003). Recent advances in molecular genetics of glaucoma. Mol Cell Biochem 253, 223-231.

Razmara, A., Duckles, S. P., Krause, D. N., and Procaccio, V. (2007). Estrogen suppresses brain mitochondrial oxidative stress in female and male rats. Brain Res 1176, 71-81.

Reisberg, B., Doody, R., Stoffler, A., Schmitt, F., Ferris, S., and Mobius, H. J. (2003). Memantine in moderate-to-severe Alzheimer's disease. N Engl J Med 348, 1333-1341.

Rhone, M., and Basu, A. (2008). Phytochemicals and age-related eye diseases. Nutrition reviews 66, 465-472.

Rodriguez-Tebar, A., Jeffrey, P. L., Thoenen, H., and Barde, Y. A. (1989). The survival of chick retinal ganglion cells in response to brain-derived neurotrophic factor depends on their embryonic age. Dev Biol 136, 296-303.

Rosenthal, A., Goeddel, D. V., Nguyen, T., Lewis, M., Shih, A., Laramee, G. R., Nikolics, K., and Winslow, J. W. (1990). Primary structure and biological activity of a novel human neurotrophic factor. Neuron 4, 767-773.

Rudzinski, M., Wong, T. P., and Saragovi, H. U. (2004). Changes in retinal expression of neurotrophins and neurotrophin receptors induced by ocular hypertension. J Neurobiol 58, 341-354.

Russelakis-Carneiro, M., Silveira, L. C., and Perry, V. H. (1996). Factors affecting the survival of cat retinal ganglion cells after optic nerve injury. J Neurocytol 25, 393-402.

Russo, R., Cavaliere, F., Berliocchi, L., Nucci, C., Gliozzi, M., Mazzei, C., Tassorelli, C., Corasaniti, M. T., Rotiroti, D., Bagetta, G., and Morrone, L. A. (2008). Modulation of pro-survival and death-associated pathways under retinal ischemia/reperfusion: effects of NMDA receptor blockade. J Neurochem 107, 1347-1357.

Salt, T. E., and Cordeiro, M. F. (2006). Glutamate excitotoxicity in glaucoma: throwing the baby out with the bathwater? Eye (London, England) 20, 730-731; author reply 731-732.

Samuelsson, G. (1999). Drugs of Natural Origin, 4th edn (Stokholm: Swedish Pharmaceutical Society).

Sappington, R. M., Sidorova, T., Long, D. J., and Calkins, D. J. (2009). TRPV1: Contribution to Retinal Ganglion Cell Apoptosis and Increased Intracellular Ca2+ with Exposure to Hydrostatic Pressure. Invest Ophth Vis Sci 50, 717-728.

Sattler, M. B., Merkler, D., Maier, K., Stadelmann, C., Ehrenreich, H., Bahr, M., and Diem, R. (2004). Neuroprotective effects and intracellular signaling pathways of erythropoietin in a rat model of multiple sclerosis. Cell Death Differ 11 Suppl 2, S181-192.

Schnebelen, C., Pasquis, B., Salinas-Navarro, M., Joffre, C., Creuzot-Garcher, C. P., Vidal-Sanz, M., Bron, A. M., Bretillon, L., and Acar, N. (2009). A dietary combination of omega-3 and omega-6 polyunsaturated fatty acids is more efficient than single supplementations in the prevention of retinal damage induced by elevation of intraocular pressure in rats. Graefes Arch Clin Exp Ophthalmol.

Schori, H., Kipnis, J., Voles, E., WoldeMussie, E., Ruiz, G., Wheeler, L. A., and Schwartz, M. (2001). Vaccination for protection of retinal ganglion cells against death from glutamate cytotoxicity and ocular hypertension: implications for glaucoma. Proceedings of the National Academy of Sciences of the United States of America 98, 3398-3403.

Schuettauf, F., Naskar, R., Vorwerk, C. K., Zurakowski, D., and Dreyer, E. B. (2000). Ganglion cell loss after optic nerve crush mediated through AMPA-kainate and NMDA receptors. Invest Ophthalmol Vis Sci 41, 4313-4316.

Schuettauf, F., Zurakowski, D., Quinto, K., Varde, M. A., Besch, D., Laties, A., Anderson, R., and Wen, R. (2005). Neuroprotective effects of cardiotrophin-like cytokine on retinal ganglion cells. Graefes Arch Clin Exp Ophthalmol 243, 1036-1042.

Schwartz, M. (2001). Physiological approaches to neuroprotection. boosting of protective autoimmunity. Surv Ophthalmol 45 Suppl 3, S256-260; discussion S273-256.

Senaldi, G., Varnum, B. C., Sarmiento, U., Starnes, C., Lile, J., Scully, S., Guo, J., Elliott, G., McNinch, J., Shaklee, C. L., et al. (1999). Novel neurotrophin-1/B cell-stimulating factor-3: a cytokine of the IL-6 family. Proceedings of the National Academy of Sciences of the United States of America 96, 11458-11463.

Shimazawa, M., Inokuchi, Y., Okuno, T., Nakajima, Y., Sakaguchi, G., Kato, A., Oku, H., Sugiyama, T., Kudo, T., Ikeda, T., et al. (2008). Reduced retinal function in amyloid precursor protein-over-expressing transgenic mice via attenuating glutamate-N-methyl-d-aspartate receptor signaling. J Neurochem 107, 279-290.

Shimazawa, M., Nakajima, Y., Mashima, Y., and Hara, H. (2009). Docosahexaenoic acid (DHA) has neuroprotective effects against oxidative stress in retinal ganglion cells. Brain Res 1251, 269-275.

Simpkins, J. W., Wen, Y., Perez, E., Yang, S., and Wang, X. (2005). Role of nonfeminizing estrogens in brain protection from cerebral ischemia: an animal model of Alzheimer's disease neuropathology. Ann N Y Acad Sci 1052, 233-242.

Singer, C. A., Rogers, K. L., Strickland, T. M., and Dorsa, D. M. (1996). Estrogen protects primary cortical neurons from glutamate toxicity. Neurosci Lett 212, 13-16.

Siu, A. W., Ortiz, G. G., Benitez-King, G., To, C. H:, and Reiter, R. J. (2004). Effects of melatonin on the nitric oxide treated retina. Br J Ophthalmol 88, 1078-1081.

Siu, A. W., and To, C. H. (2002). Nitric oxide and hydroxyl radical-induced retinal lipid peroxidation in vitro. Clin Exp Optom 85, 378-382.

Skradski, S., and White, H. S. (2000). Topiramate blocks kainate-evoked cobalt influx into cultured neurons. Epilepsia 41 Suppl 1, S45-47.

Solberg, Y., Rosner, M., Turetz, J., and Belkin, M. (1997). MK-801 has neuroprotective and antiproliferative effects in retinal laser injury. Invest Ophthalmol Vis Sci 38, 1380-1389.

Sommer, A. (1989). Intraocular pressure and glaucoma. Am J Ophthalmol 107, 186-188.

Soti, C., Nagy, E., Giricz, Z., Vigh, L., Csermely, P., and Ferdinandy, P. (2005). Heat shock proteins as emerging therapeutic targets. British journal of pharmacology 146, 769-780.

Sribnick, E. A., Ray, S. K., Nowak, M. W., Li, L., and Banik, N. L. (2004). 17beta-estradiol attenuates glutamate-induced apoptosis and preserves electrophysiologic function in primary cortical neurons. J Neurosci Res 76, 688-696.

Sugden, D., Pickering, H., Teh, M. T., and Garratt, P. J. (1997). Melatonin receptor pharmacology: toward subtype specificity. Biol Cell 89, 531-537.

Sun, F. Y., Lin, X., Mao, L. Z., Ge, W. H., Zhang, L. M., Huang, Y. L., and Gu, J. (2002). Neuroprotection by melatonin against ischemic neuronal injury associated with modulation of DNA damage and repair in the rat following a transient cerebral ischemia. J Pineal Res 33, 48-56.

Tajes Orduna, M., Pelegri Gabalda, C., Vilaplana Hortensi, J., Pallas Lliberia, M., and Camins Espuny, A. (2009). An evaluation of the neuroprotective effects of melatonin in an in vitro experimental model of age-induced neuronal apoptosis. J Pineal Res 46, 262-267.

Tamura, Y., Sato, Y., Yokota, T., Akaike, A., Sasa, M., and Takaori, S. (1993). Ifenprodil prevents glutamate cytotoxicity via polyamine modulatory sites of N-methyl-D-aspartate receptors in cultured cortical neurons. J Pharmacol Exp Ther 265, 1017-1025.

Tang, Q., Hu, Y., and Cao, Y. (2006). Neuroprotective effect of melatonin on retinal ganglion cells in rats, J Huazhong Univ Sci Technolog Med Sci 26, 235-237, 253.

Tatton, W. G., Chalmers-Redman, R. M., Sud, A., Podos, S. M., and Mittag, T. W. (2001). Maintaining mitochondrial membrane impermeability an opportunity for new therapy in glaucoma? Surv Ophthalmol 45 Suppl 3, S277-283; discussuin S295-276.

Teiten, M. H., Reuter, S., Schmucker, S., Dicato, M., and Diederich, M. (2009). Induction of heat shock response by curcumin in human leukemia cells. Cancer Lett 279, 145-154.

Tezel, G. (2006). Oxidative stress in glaucomatous neurodegeneration: mechanisms and consequences, Prog Retin Eye Res 25, 490-513.

Tezel, G., Chauhan, B. C., LeBlanc, R. P., and Wax, M. B. (2003). Immunohistochemical assessment of the glial mitogen-activated protein kinase activation in glaucoma. Invest Ophthalmol Vis Sci 44, 3025-3033.

Tezel, G., Hernandez, R., and Wax, M. B. (2000). Immunostaining of heat shock proteins in the retina and optic nerve head of normal and glaucomatous eyes. Archives of ophthalmology 118, 511-518.

Tezel, G., Li, L. Y., Patil, R. V., and Wax, M. B. (2001). TNF-alpha and TNF-alpha receptor-1 in the retina of normal and glaucomatous eyes. Invest Ophthalmol Vis Sci 42, 1787-1794.

Tezel, G., Seigel, G. M., and Wax, M. B. (1998). Autoantibodies to small heat shock proteins in glaucoma. Invest Ophthalmol Vis Sci 39, 2277-2287.

Tezel, G., and Yang, X. (2004). Caspase-independent component of retinal ganglion cell death, in vitro. Invest Ophthalmol Vis Sci 45, 4049-4059.

Tezel, G., Yang, X., Luo, C., Cai, J., Kain, A. D., Powell, D. W., Kuehn, M. H., and Pierce, W. M. (2009). Hemoglobin expression and regulation in glaucoma: insights into retinal ganglion cell oxygenation. Invest Ophthalmol Vis Sci 51, 907-919.

Tezel, G., Yang, X., Luo, C., Peng, Y., Sun, S. L., and Sun, D. (2007). Mechanisms of immune system activation in glaucoma: oxidative stress-stimulated antigen presentation by the retina and optic nerve head glia. Invest Ophthalmol Vis Sci 48, 705-714.

Tezel, G., Yang, X., Yang, J., and Wax, M. B. (2004). Role of tumor necrosis factor receptor-1 in the death of retinal ganglion cells following optic nerve crush injury in mice. Brain Res 996, 202-212.

Thiagarajan, G., Chandani, S., Harinarayana Rao, S., Samuni, A. M., Chandrasekaran, K., and Balasubramanian, D. (2002). Molecular and cellular assessment of *ginkgo biloba* extract as a possible ophthalmic drug. Exp Eye Res 75, 421-430.

Thomas, S. C., Ryan, M. A., Shanley, T. P., and Wong, H. R. (1998). Induction of the stress response with prostaglandin A1 increases I-kappaBalpha gene expression. Faseb J 12, 1371-1378.

Tsuda, K. (2004). Neuroprotective effects of MK-801 and catecholamine release in the central nervous system. Stroke 35, e96.

Vallazza-Deschamps, G., Fuchs, C., Cia, D., Tessier, L. H., Sahel, J. A., Dreyfus, H., and Picaud, S. (2005). Diltiazem-induced neuroprotection in glutamate excitotoxicity and ischemic insult of retinal neurons. Doc Ophthalmol 110, 25-35.

Verwey, N. A., Schuitemaker, A., van der Flier, W. M., Mulder, S. D., Mulder, C., Hack, C. E., Scheltens, P., Blankenstein, M. A., and Veerhuis, R. (2008). Serum amyloid p component as a biomarker in mild cognitive impairment and Alzheimer's disease. Dement Geriatr Cogn Disord 26, 522-527.

Villemagne, V. L., Pike, K. E., Darby, D., Maruff, P., Savage, G., Ng, S., Ackermann, U., Cowie, T. F., Currie, J., Chan, S. G., et al. (2008). Abeta deposits in older non-demented individuals with cognitive decline are indicative of preclinical Alzheimer's disease. Neuropsychologia 46, 1688-1697.

Wajant, H., and Scheurich, P. (2001). Tumor necrosis factor receptor-associated factor (TRAF) 2 and its role in TNF signaling. Int J Biochem Cell Biol 33, 19-32.

Wang, W. P., Iyo, A. H., Miguel-Hidalgo, J., Regunathan, S., and Zhu, M. Y. (2006). Agmatine protects against cell damage induced by NMDA and glutamate in cultured hippocampal neurons. Brain Res 1084, 210-216.

Ward, M. S., Khoobehi, A., Lavik, E. B., Langer, R., and Young, M. J. (2007). Neuroprotection of retinal ganglion cells in DBA/2J mice with GDNF-loaded biodegradable microspheres. Journal of pharmaceutical sciences 96, 558-568.

Wax, M., and Patil, R. (1994). A rationale for gene targeting in glaucoma therapy. J Ocul Pharmacol 10, 403-410.

Weber, A. J., Chen, H., Hubbard, W. C., and Kaufman, P. L. (2000). Experimental glaucoma and cell size, density, and number in the primate lateral geniculate nucleus. Invest Ophthalmol Vis Sci 41, 1370-1379.

Wheeler, L. A., Lai, R., and Woldemussie, E. (1999). From the lab to the clinic: activation of an alpha-2 agonist pathway is neuroprotective in models of retinal and optic nerve injury. Eur J Ophthalmol 9 Suppl 1, S17-21.

Wiechmann, A. F., Campbell, L. D., and Defoe, D. M. (1999). Melatonin receptor RNA expression in *Xenopus retina*. Brain Res Mol Brain Res 63, 297-303.

Wiechmann, A. F., and Wirsig-Wiechmann, C. R. (1994). Melatonin receptor distribution in the brain and retina of a lizard, Anolis carolinensis. Brain Behav Evol 43, 26-33.

WoldeMussie, E., Ruiz, G., Wijono, M., and Wheeler, L. A. (2001). Neuroprotection of retinal ganglion cells by brimonidine in rats with laser-induced chronic ocular hypertension. Invest Ophthalmol Vis Sci 42, 2849-2855.

WoldeMussie, E., Voles, E., Schwartz, M., Ruiz, G., and Wheeler, L. A. (2002). Neuroprotective effect of memantine in different retinal injury models in rats. J Glaucoma 11, 474-480.

Yamamoto, R., Yoneda, S., and Hara, H. (2004). Neuroprotective effects of beta-secretase inhibitors against rat retinal ganglion cell death. Neurosci Lett 370, 61-64.

Yancheva, S., Ihl, R., Nikolova, G., Panayotov, P., Schlaefke, S., and Hoerr, R. (2009). *Ginkgo biloba* extract EGb 761 (R), donepezil or both combined in the treatment of Alzheimer's disease with neuropsychiatric features: a randomised, double-blind, exploratory trial. Aging Ment Health 13, 183-190.

Yang, S. W., Lee, B. R., and Koh, J. W. (2007). Protective effects of epigallocatechin gallate after UV irradiation in cultured human retinal pigment epithelial cells. Korean J Ophthalmol 21, 232-237.

Yoles, E., Hauben, E., Palgi, O., Agranov, E., Gothilf, A., Cohen, A., Kuchroo, V., Cohen, I. R., Weiner, H., and Schwartz, M. (2001). Protective autoimmunity is a physiological response to CNS trauma. J Neurosci 21, 3740-3748.

Yoneda, S., Hara, H., Hirata, A., Fukushima, M., Inomata, Y., and Tanihara, H. (2005). Vitreous fluid levels of beta-amyloid ((1-42)) and tau in patients with retinal diseases. Jpn J Ophthalmol 49, 106-108.

Yoneda, S., Tanaka, E., Goto, W., Ota, T., and Hara, H. (2003). Topiramate reduces excitotoxic and ischemic injury in the rat retina. Brain Res 967, 257-266.

Yu, X., Tang, Y., Li, F., Frank, M. B., Huang, H., Dozmorov, I., Zhu, Y., Centola, M., and Cao, W. (2005). Protection against hydrogen peroxide-induced cell death in cultured human retinal pigment epithelial cells by 17beta-estradiol: a differential gene expression profile. Mech Ageing Dev 126, 1135-1145.

Yuan, L., and Neufeld, A. H. (2001). Activated microglia in the human glaucomatous optic nerve head, J Neurosci Res 64, 523-532.

Yucel, Y. H., Gupta, N., Zhang, Q., Mizisin, A. P., Kalichman, M. W., and Weinreb, R. N. (2006). Memantine protects neurons from shrinkage in the lateral geniculate nucleus in experimental glaucoma. Archives of ophthalmology 124, 217-225.

Zhang, B., Rusciano, D., and Osborne, N. N. (2008). Orally administered epigallocatechin gallate attenuates retinal neuronal death in vivo and light-induced apoptosis in vitro. Brain Res 1198, 141-152.

Zhang, B., Safa, R., Rusciano, D., and Osborne, N. N. (2007). Epigallocatechin gallate, an active ingredient from green tea, attenuates damaging influences to the retina caused by ischemia/reperfusion. Brain Res 1159, 40-53.

Zhang, L., Rubinow, D. R., Xaing, G., Li, B. S., Chang, Y. H., Maric, D., Barker, J. L., and Ma, W. (2001). Estrogen protects against beta-amyloid-induced neurotoxicity in rat hippocampal neurons by activation of Akt. Neuroreport 12, 1919-1923.

Zhou, X., Li, F., Ge, J., Sarkisian, S. R., Jr., Tomita, H., Zaharia, A., Chodosh, J., and Cao, W. (2007). Retinal ganglion cell protection by 17-beta-estradiol in a mouse model of inherited glaucoma. Dev Neurobiol 67, 603-616.

| Mechanism | Target | Compound | Model | References |
| --- | --- | --- | --- | --- |
| Excitotoxicity | NMDA-R | Memantine | in vitro (NMDA) in vivo (OHT, Optic Nerve Crush, UEG, DBA/2J, Ischemia) | (Ju et al., 2009; Kim et al., 2002; Lagreze et al., 1998; Pellegrini and Lipton, 1993; WoldeMussie et al., 2002; Yucel et al., 2006) |

-continued

| Mechanism | Target | Compound | Model | References |
|---|---|---|---|---|
| | | MK801 | in vitro (Hypoxia, Glutamate) in vivo (NMDA, Quinolinate, Laser, OHT, MCAO, SSP, Axotomy) | (Chaudhary et al., 1998; el-Asrar et al., 1992; Foster et al., 1988; Guo et al., 2006; Russelakis-Carneiro et al., 1996; Solberg et al., 1997; Tamura et al., 1993; Tsuda, 2004) |
| | | Flupritine | in vivo (NMDA, Ischemia) | (Nash et al., 2000) |
| | | DXM | in vitro (Hypoxia) in vivo (Laser, OHT, SSP, Subdural Hematoma) | (Calzada et al., 2002; Duhaime et al., 1996; Goldberg et al., 1987; Guo et al., 2006) |
| | | Eliprodil | in vitro (Glutamate) in vivo (NMDA, Ischemia) | (Kapin et al., 1999; Pang et al., 1999) |
| | | Ifenprodil | in vitro (Glutamate) in vivo (OHT, SSP) | (Guo et al., 2006; Tamura et al., 1993) |
| | | p38 inhibitor | in vivo (Axotomy) | (Kikuchi et al., 2000) |
| | AMPA/Kainate-R | Topiramate | in vitro (Kainate) | (Gibbs et al., 2000; Skradski and White, 2000) |
| | | DNQX | in vitro (Glutamate) in vivo (Optic Nerve Crush) | (Otori et al., 1998; Schuettauf et al., 2000) |
| | | Arachidonic Acid | in vitro (Glutamate) in vivo (Kainate) | (Cunha et al., 2004; Kawasaki et al., 2002) |
| | $mGluR_2/mGluR_3$ | LY354740 | in vitro (NMDA, Glucose/Oxygen Starvation) in vivo (Ischemia, OHT, SSP) | (Behrens et al., 1999; Guo et al., 2006) |
| | $Ca^{2+}$ Channels | Flunarizine | in vivo (Axotomy, Ischemia, NMDA) | (Eschweiler and Bahr, 1993; Osborne et al., 2002) |
| | | Diltiazem | in vitro (Glutamate) in vivo (Ischemia) | (Vallazza-Deschamps et al., 2005) |
| | | Riluzole | in vivo (Axotomy) | (Ettaiche et al., 1999) |
| | | TRPV1 agonist | in vitro (hydrostatic pressure) in vivo (DBA/2 mouse) | (Sappington et al., 2009) |
| | $Na^+$ Channels | Phenytoin | in vivo (Optic Nerve Crush, OHT) | (Hains and Waxman, 2005; Naskar et al., 2002) |
| | ACh receptors | Galantamine | in vivo (OHT, optic nerve axotomy) | (Almasieh et al., 2010) |
| Mitochondrial Dysfunction | ROS | Lipoic Acid | in vivo (Aged, Ischemia) | (Chidlow et al., 2002; Hagen et al., 1999; Liu et al., 2002) |
| | | FK506 | in vivo (Optic Nerve Crush) | (Huang et al., 2005) |
| | ROS, NF-κB | Creatine | in vitro (Glutamate) in vivo (Animal Model, MPTP) | (Juravleva et al., 2005; Klivenyi et al., 1999; Matthews et al., 1999; Matthews et al., 1998) |
| | PI3-Akt, NF-κB | Erythropoietin | in vivo (Ischemia, Optic Neuritis, Axotomy, Cytokines, DBA/2J) | (Digicaylioglu and Lipton, 2001; Junk et al., 2002; Kilic et al., 2005b; Sattler et al., 2004) |
| | Mitochondria | EGCG | in vivo (DBA/2J) | (Negishi et al., 2004; Yang et al., 2007; Zhang et al., 2008; Zhang et al., 2007) |
| | PTP | $CoQ_{10}$ | in vitro (SS, Antimycin A, Ceramide, UVC, $H_2O_2$) in vivo (Ischemia, NMDA) | (Nakajima et al., 2008; Nucci et al., 2007b; Papucci et al., 2003; Russo et al., 2008) |
| | Unknown | Nicotinamide | in vivo (Animal Model) | (Beal, 2003) |
| Protein Misfolding | β-amyloid | Congo Red | in vivo (OHT, β-amyloid) | (Guo et al., 2007) |
| | | Anti-β-amyloid | in vivo (OHT, β-amyloid) | (Guo et al., 2007) |
| | β-secretase | Z-VLL-CHO | in vivo (OHT, β-amyloid) | (Guo et al., 2007) |
| | HSPs | GGA | in vivo (OHT) | (Ishii et al., 2003) |

-continued

| Mechanism | Target | Compound | Model | References |
|---|---|---|---|---|
| Oxidative Stress | NOS | Aminoguanidine | in vitro (Explants) in vivo (OHT) | (Katsuki et al., 2004; Neufeld, 2004; Neufeld et al., 1999) |
| | | Ginko Biloba | in vitro (Alloxan, Dexamethsone, Glutamate) in vivo (OHT) | (Hirooka et al., 2004; Thiagarajan et al., 2002) |
| | ROS | Brazilia Green Propolis | in vitro ($H_2O_2$, SSP, Oxygen-Glucose Deprivation/Reoxygenation) in vivo (NMDA) | (Inokuchi et al., 2006; Nakajima et al., 2009a) |
| | | Carotenoids | in vitro ($H_2O_2$, SS) in vivo (OHT, Ischemia) | (Li et al., 2009; Nakajima et al., 2009b; Neacsu et al., 2003; Schnebelen et al., 2009; Shimazawa et al., 2009) |
| | | Melatonin | in vivo (Ischemia, Kainate) | (Cazevieille et al., 1997; Tang et al., 2006) |
| | | Tocopherol | in vitro ($H_2O_2$) in vivo (Ischemia) | (Aydemir et al., 2004; Nakajima et al., 2008) |
| | | PPAR-γ agonists | in vitro (Glutamate) | (Aoun et al., 2003) |
| Inflammation and Immunological Strategies | Multiple | Curcumin | in vitro (IS, NMDA, $H_2O_2$) in vivo (Animal Model) | (Abe et al., 1999; Lim et al., 2001; Mandal et al., 2009; Matteucci et al., 2005; Teiten et al., 2009) |
| | ROS | Pitavastatin | in vivo (NMDA) | (Nakazawa et al., 2007) |
| | TNFα | GLC756 | in vitro (IS) in vivo (IS) | (Laengle et al., 2006a; Laengle et al., 2006b) |
| | Myelin Basic Protein | Cop-1 | in vivo (OHT, Optic Nerve Crush, Glutamate) | (Bakalash et al., 2003; Ben Simon et al., 2006; Kipnis et al., 2000; Li et al., 2008; Schori et al., 2001) |
| | Unknown | Agmatine | in vitro (Hypoxia, NMDA, TNFα | (Hong et al., 2009; Hong et al., 2008; Wang et al., 2006) |
| Neurotrophic Withdrawal | TrkB, p75 | BDNF | in vitro (BDNF Withdrawal) in vivo (Axotomy, Superior Colliculus Removal, OHT) | (Cui and Harvey, 1995; Harvey et al., 2006; Johnson et al., 1986; Mansour-Robaey et al., 1994; Rodriguez-Tebar et al., 1989) |
| | | NT-1 | in vivo (Optic Nerve Crush, NMDA) | (Schuettauf et al., 2005; Scnaldi et al., 1999) |
| | TrkB | NT-4/5 | in vivo (Superior Colliculus removal) | (Cui and Harvey, 1995) |
| | CNTF receptor | CNTF | in vivo (OHT) | (Ji et al., 2004; Pease et al., 2009) |
| | GFRA-1, GFRA-2 | GDNF | in vivo (OHT) | (Jiang et al., 2007; Jing et al., 1996; Naskar et al., 2000; Ward et al., 2007) |
| | TrkA | NGF TrkA agonist | In vivo (OHT) in vivo (axotomy) | (Colafrancesco et al., 2010; Lambiase et al., 2009; Lebrun-Julien et al., 2009) |
| Gene Therapy | TrkB, BIRC-4, GDNF | Viral Vectors | in vivo (Axotomy, OHT) | (Cheng et al., 2002; McKinnon et al., 2002b; Pease et al., 2009) |
| Multiple Mechanisms | Multiple | Estrogen | in vitro (Glutamate) in vivo (Ovariectomy, DBA/2J) | (Kumar et al., 2005; Nakazawa et al., 2006; Sribnick et al., 2004) |
| | | Brimonidine | in vitro (NMDA, Glyoxal, $H_2O_2$) in vivo (Ischemia, Optic Nerve Crush, OHT) | (Donello et al., 2001; Dong et al., 2008; Hernandez et al., 2008; Knels et al., 2008; Lai et al., 2002; Wheeler et al., 1999; WoldeMussie et al., 2001) |
| | | Cannabinoids | in vitro (Potassium Chloride, Ischemia) in vivo (NMDA, Ischemia) | (El-Remessy et al., 2003; Nucci et al., 2007a; Opere et al., 2006) |

The invention claimed is:

1. A method of determining the stage of a disease or diagnosing a disease, comprising:

generating an in vivo image of apoptosing cells in a subject's eye, wherein the subject has been administered a labeled apoptotic marker, and counting the number of apoptosing cells or analyzing a pattern of distribution of apoptosing cells in the image, the method further comprising comparing the number of apoptosing cells or pattern of distribution of apoptosing cells with a previously generated in vivo image of apoptosing cells in the subject's eye.

2. The method of claim 1, wherein the disease is a neurodegenerative disease.

3. The method of claim 1, wherein the disease is an ocular neurodegenerative disease.

4. The method of claim 1, wherein the marker is an annexin.

5. The method of claim 1, wherein the label is a wavelength-optimized label.

6. The method of claim 1, comprising overlaying the image generated onto an image of the subject's eye, such that specific cells may be compared.

7. The method of claim 1, further comprising administering an appropriate course of treatment for the disease or stage of disease identified.

8. A method of staging disease, comprising:
   generating an in vivo image of cell activity or cell death in a subject's eye, wherein a first labeled marker and a second labeled marker have been administered to the subject,
   wherein the first and second markers are markers of different phases of apoptosis, or markers of two selected from cell activity, apoptosis, and necrosis, and
   wherein the labels are different, and
   assessing the stage of disease by studying co-localisation of the markers in the image, the method further comprising comparing the image with a previously generated in vivo image of cell activity or cell death in the subject's eye.

9. The method of claim 8, wherein one of the markers is an apoptosis marker.

10. The method of claim 9, wherein one of the markers is a necrosis marker.

11. The method of claim 9, wherein one of the markers is a cell activity marker.

12. The method of claim 8, wherein both of the markers are apoptosis markers.

13. The method of claim 8, wherein the disease is a neurodegenerative disease.

14. The method of claim 8, wherein the disease is an ocular neurodegenerative disease.

15. The method of claim 8, wherein one of the markers is an annexin.

16. The method of claim 8, wherein the label is a wavelength-optimized label.

17. The method of claim 8, comprising overlaying the image generated onto an image of the subject's eye, such that specific cells may be compared.

18. The method of claim 8, further comprising administering an appropriate course of treatment for the disease or stage of disease identified.

* * * * *